(12) United States Patent
Ozaki et al.

(10) Patent No.: US 10,549,268 B2
(45) Date of Patent: Feb. 4, 2020

(54) FILTER ELEMENT FOR DECOMPOSING CONTAMINANTS, SYSTEM FOR DECOMPOSING CONTAMINANTS AND METHOD USING THE SYSTEM

(71) Applicant: NITTO DENKO CORPORATION, Osaka (JP)

(72) Inventors: Takashi Ozaki, Osaka (JP); Takuya Fukumura, Osaka (JP); Keita Mine, Osaka (JP); Guang Pan, Oceanside, CA (US); Ekambaram Sambandan, Oceanside, CA (US); Rajesh Mukherjee, Oceanside, CA (US)

(73) Assignee: Nitto Denko Corporation, Osaka (JP)

( * ) Notice: Subject to any disclaimer, the term of this patent is extended or adjusted under 35 U.S.C. 154(b) by 171 days.

(21) Appl. No.: 14/903,025

(22) PCT Filed: Jul. 4, 2014

(86) PCT No.: PCT/JP2014/068520
§ 371 (c)(1),
(2) Date: Jan. 21, 2016

(87) PCT Pub. No.: WO2015/002324
PCT Pub. Date: Jan. 8, 2015

(65) Prior Publication Data
US 2016/0129432 A1     May 12, 2016

Related U.S. Application Data

(60) Provisional application No. 61/843,264, filed on Jul. 5, 2013, provisional application No. 61/843,267, filed
(Continued)

(30) Foreign Application Priority Data

May 30, 2014   (JP) ................................ 2014-113001

(51) Int. Cl.
*B01J 35/00* (2006.01)
*B01J 23/888* (2006.01)
(Continued)

(52) U.S. Cl.
CPC ............. *B01J 35/004* (2013.01); *A61L 9/205* (2013.01); *B01D 53/8668* (2013.01);
(Continued)

(58) Field of Classification Search
CPC ................ B01J 2523/00; B01J 2523/69; B01J 2523/3712; B01J 2523/13; B01J 2523/43;
(Continued)

(56) References Cited

U.S. PATENT DOCUMENTS 4,917,820 A   4/1990   Matsumoto et al.
4,955,208 A   9/1990   Kawashima et al.
(Continued)

FOREIGN PATENT DOCUMENTS

CN   1805780 A   7/2006
CN   1826144 A   8/2006
(Continued)

OTHER PUBLICATIONS

Westrich et al, "High-Temperature Photocatalytic Ethylene Oxidation over TiO2", J. Phys. Chem. C 2011, 115, pp. 16537-16543 (Year: 2011).*
(Continued)

*Primary Examiner* — Ngoc-Yen Nguyen
(74) *Attorney, Agent, or Firm* — K&L Gates LLP; Louis C. Cullman; Hal Gibson

(57) ABSTRACT

Embodiments of the present invention include a filter element for decomposing contaminants including a substrate, and a photocatalytic composition comprising at least a photocatalyst. The embodiments of the present invention also includes a system for decomposing contaminants
(Continued)

including a substrate, and a photocatalytic composition comprising at least a photocatalyst; and a method using the system.

23 Claims, 28 Drawing Sheets

Related U.S. Application Data on Jul. 5, 2013, provisional application No. 61/899,799, filed on Nov. 4, 2013, provisional application No. 61/899,804, filed on Nov. 4, 2013, provisional application No. 61/944,879, filed on Feb. 26, 2014.

(51) Int. Cl.
| | | |
|---|---|---|
| *A61L 9/20* | (2006.01) | |
| *B01J 23/72* | (2006.01) | |
| *B01J 23/14* | (2006.01) | |
| *B01J 23/30* | (2006.01) | |
| *B01J 23/34* | (2006.01) | |
| *B01D 53/86* | (2006.01) | |

(52) U.S. Cl.
CPC .............. *B01J 23/14* (2013.01); *B01J 23/30* (2013.01); *B01J 23/34* (2013.01); *B01J 23/72* (2013.01); *B01J 23/888* (2013.01); *B01D 2255/2061* (2013.01); *B01D 2255/2065* (2013.01); *B01D 2255/2073* (2013.01); *B01D 2255/2094* (2013.01); *B01D 2255/20707* (2013.01); *B01D 2255/20761* (2013.01); *B01D 2255/20769* (2013.01); *B01D 2255/20776* (2013.01); *B01D 2255/802* (2013.01); *B01D 2257/7022* (2013.01); *B01D 2257/90* (2013.01)

(58) Field of Classification Search
CPC ............... B01J 2523/31; B01J 2523/47; B01J 2523/56; B01J 2523/57; B01J 23/14; B01J 23/30; B01J 23/34; B01J 23/72; B01J 23/835; B01J 23/888; B01J 27/24; B01J 35/004
See application file for complete search history.

(56) References Cited

U.S. PATENT DOCUMENTS

| | | | |
|---|---|---|---|
| 5,015,282 A | | 5/1991 | Takahashi et al. |
| 5,190,668 A | * | 3/1993 | Chuang .............. B01D 53/8668 210/750 |
| 5,253,488 A | | 10/1993 | Kim et al. |
| 5,416,060 A | | 5/1995 | Yamamoto et al. |
| 5,835,840 A | | 11/1998 | Goswami |
| 5,933,702 A | | 8/1999 | Goswami |
| 5,972,831 A | * | 10/1999 | Poncelet ................ B01J 35/002 423/115 |
| 6,121,191 A | | 9/2000 | Komatsu |
| 6,265,341 B1 | | 7/2001 | Komatsu |
| 6,365,545 B1 | | 4/2002 | Komatsu |
| 6,627,579 B1 | | 9/2003 | Sakatani |
| 7,296,422 B2 | | 11/2007 | Strohm et al. |
| 7,947,318 B2 | | 5/2011 | Tracy |
| 8,293,171 B2 | | 10/2012 | Haven |
| 8,628,726 B2 | | 1/2014 | Pham-Huu et al. |
| 8,791,044 B2 | | 7/2014 | Varma et al. |
| 2003/0092567 A1 | * | 5/2003 | Tanaka ................... B01D 53/94 502/302 |
| 2003/0144140 A1 | | 7/2003 | Matsuo |
| 2004/0258581 A1 | | 12/2004 | Wei et al. |
| 2005/0129589 A1 | | 6/2005 | Wei et al. |
| 2006/0124442 A1 | | 6/2006 | Valpey, III |
| 2006/0152695 A1 | * | 7/2006 | Nagahara ............. B01D 53/185 355/30 |
| 2006/0153749 A1 | | 7/2006 | Schroder |
| 2007/0248831 A1 | | 10/2007 | Nishihara |
| 2008/0251081 A1 | | 10/2008 | Claussen et al. |
| 2011/0123694 A1 | | 5/2011 | Ryska |
| 2011/0203584 A1 | | 8/2011 | Cozean |
| 2011/0262312 A1 | | 10/2011 | Pham-Huu et al. |
| 2011/0266136 A1 | | 11/2011 | Varma et al. |
| 2012/0019917 A1 | * | 1/2012 | Riebel ................ B01D 53/8668 359/599 |
| 2012/0070334 A1 | | 3/2012 | Ehrhorn |
| 2012/0198862 A1 | | 8/2012 | Arrigo |
| 2013/0052112 A1 | | 2/2013 | Cozean |
| 2014/0116444 A1 | | 5/2014 | Cozean et al. |
| 2014/0123688 A1 | * | 5/2014 | Ehrhorn .................. A23B 7/152 62/78 |

FOREIGN PATENT DOCUMENTS

| | | |
|---|---|---|
| EP | 0261422 A | 3/1988 |
| EP | 0911078 A | 4/1999 |
| EP | 0931581 | 7/1999 |
| EP | 0960644 A1 | 12/1999 |
| EP | 1491218 A1 | 12/2004 |
| EP | 2525173 | 11/2012 |
| EP | 2559744 | 2/2013 |
| EP | 1966229 B1 | 10/2015 |
| JP | 10146531 A | 6/1998 |
| JP | 2001072419 A | 3/2001 |
| JP | 2001126539 A | 5/2001 |
| JP | 2001-226516 A | 8/2001 |
| JP | 2002-028412 | 1/2002 |
| JP | 2002-333266 A | 11/2002 |
| JP | 2002333266 A | 11/2002 |
| JP | 2003-053194 | 2/2003 |
| JP | 2003117407 A | 4/2003 |
| JP | 2005-160494 | 6/2005 |
| JP | 2006-223939 | 8/2006 |
| JP | 2006-305563 | 11/2006 |
| JP | 2007291307 A | 8/2007 |
| JP | 2007-291307 A | 11/2007 |
| JP | 2009-81235 A | 4/2009 |
| JP | 2009081235 A | 4/2009 |
| JP | 2009-280479 A | 12/2009 |
| JP | 2009280479 A | 12/2009 |
| JP | 2010-36135 A | 2/2010 |
| JP | 2011-212613 | 10/2011 |
| WO | 1990002572 | 3/1990 |
| WO | 1991009823 | 7/1991 |
| WO | 1998/31451 A1 | 7/1998 |
| WO | 1998-031451 A1 | 7/1998 |
| WO | 0156620 | 10/2002 |
| WO | 2005/102521 A1 | 3/2005 |
| WO | 2005-102521 A1 | 11/2005 |
| WO | 2007/026387 A2 | 3/2007 |
| WO | 2007147743 | 3/2009 |
| WO | 20071447744 | 3/2009 |
| WO | 2012/023612 A1 | 2/2012 |
| WO | 2012155907 | 11/2012 |
| WO | 2013/106776 A2 | 7/2013 |

OTHER PUBLICATIONS

Extended European Search Report dated Feb. 17, 2017 in European Patent Application No. 14819611.6.
International Search Report of PCT/JP2014/068520 filed Jul. 4, 2014, dated Oct. 28, 2014.
Chen, Liang, et al. "CeO2-WO3 Mixed Oxides for the Selective Catalytic Reduction of Nox by Nh3 Over a Wide temperature Range". Catal Lett 141:1859-1864 (2011).
JP-OA 2016-523091 drafted on Jan. 12, 2018 and issued on Jan. 16, 2018.
Natile et al., WO3/CeO2 Nanocomposite Powders: Synthesis, Characterization, and Reactivity. Chem. Mater., 18 (14), pp. 3270-3280 (2006).

(56) References Cited

OTHER PUBLICATIONS

Taiwanese Office Action dated Sep. 30, 2017 for Taiwanese Application No. 103123267 (Original Office Action and translation enclosed).

Office Action for European Patent Application No. 14819611.6 dated Sep. 19, 2019.

* cited by examiner

Ethylene removal

| B-LED | 10 ppi filter | 30 ppi filter |
|---|---|---|
| 5mW/cm2 | 81.19% | 88.43% |
| 10mW/cm2 | 90.57% | 93.74% |
| 20mW/cm2 | 96.74% | 96.54% |

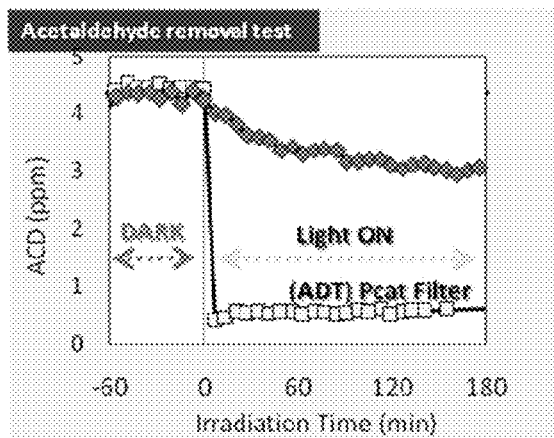
FIG.17A
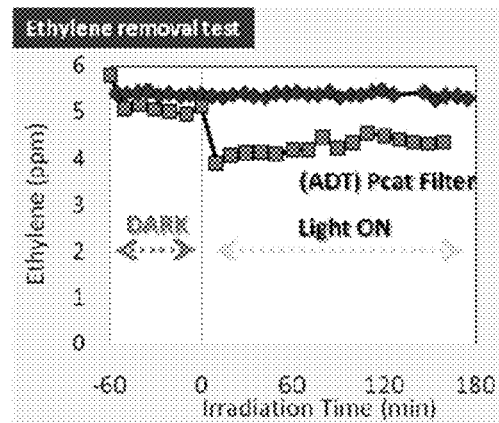
FIG.17B
| | UV Pcat Filter | (ADT) |
|---|---|---|
| Acetaldehyde | 33% | 85% |
| Ethylene | 0% | 13% |
FIG.18

| Subst. | Size (mm) | Gas | Light | RA (%) | QA (umol/H) |
|---|---|---|---|---|---|
| ADT-ANN x1 | 50x100x5 | Ethylene | BLED 20mW/cm$^2$ | 14.91 | 2.09 |
| | | | BLED 30mW/cm$^2$ | 17.47 | 2.45 |
| ADT-ANN x2 | 50x100x10 | Ethylene | BLED 20mW/cm$^2$ | 13.86 | 2.11 |
| | | | BLED 30mW/cm$^2$ | 17.02 | 2.59 |
| Commercial | 50x100x13 | Ethylene | BLED 20mW/cm$^2$ | 2.68 | 0.41 |
| | | | BLED 30mW/cm$^2$ | 6.32 | 0.96 |
| ADT-ANN x1 | 50x100x5 | Acetaldehyde | BLED 5mW/cm$^2$ | 81.19 | 9.60 |
| | | | BLED 10mW/cm$^2$ | 90.57 | 10.70 |
| | | | BLED 20mW/cm$^2$ | 96.74 | 11.43 |
| Commercial | 50x100x13 | Acetaldehyde | BLED 5mW/cm$^2$ | 93.38 | 10.66 |
| | | | BLED 10mW/cm$^2$ | 96.61 | 11.02 |
| | | | BLED 20mW/cm$^2$ | 97.02 | 11.06 |

FIG. 19

FILTER ELEMENT FOR DECOMPOSING CONTAMINANTS, SYSTEM FOR DECOMPOSING CONTAMINANTS AND METHOD USING THE SYSTEM

CROSS REFERENCE TO RELATED APPLICATIONS

This application is a national phase of PCT/jp2014/068520 filed on Jul. 4, 2014, which claims the benefit under 35 U.S.C. § 119(e) to U S. Provisional Application Ser. No. 61/843,264 filed Jul. 5, 2013, U.S. Provisional Application Ser. No. 61/843,265 filed Jul. 5, 2013, U.S. Provisional Application Ser. No. 61/899,799 filed Nov. 4, 2013, U.S. Provisional Application Ser. No. 61/899,804 filed Nov. 4, 2013, U.S. Provisional Application Ser. No. 61/944,879 filed Feb. 26, 2014, and foreign priority Japanese Application No. 2014-113001 filed on May 30, 2014 the entire contents of all of which are hereby incorporated by reference in their entirety.

TECHNICAL FIELD

The present embodiments generally relate to reduction of contaminants in air. More particularly, the present embodiments pertain to a photocatalytic element for removing microbes and malodorous gases from the air using a photocatalytic composition, reducing the concentration of ethylene in air using a photocatalytic composition, and a method of using the element to purify air in buildings, airplanes, and enclosures, and a method of using the element to extend the stock life of harvested plants including fruit, vegetables, and flowers.

BACKGROUND ART

Photocatalysts are known as an effective way to reduce the concentration of gases such as ethylene, and other contaminants in the air, including malodorous gases and microbes. This is desirable because ethylene gas is known to contribute to the aging and senescence of plants. Additionally, having cleaner and better-smelling air is desirable. Various ways of controlling concentrations of ethylene and purifying air have been employed in the past, including filters, oxidizers, and photocatalysts.

Various types of air filter units incorporated with an air filter element have been used for filtering and removing various kinds of powder dust such as pollens, mites, and dust. While such filter units with conventional filter elements can remove powder dust at the intended design efficiency, conventional filter units are incapable of removing materials that exist in a gas phase, including, for example, harmful gases such as volatile organic compounds (VOCs), and malodorant components that produce a bad odor.

Herein, it has been known that such harmful gases and malodorant components can be adsorbed and removed with the use of activated carbon. However, because the adsorption capability of activated carbon is limited, the activated carbon needs to be replaced every time the adsorption reaches saturation. If left unreplaced in the saturated state, the activated carbon would no longer be able to sufficiently adsorb and remove harmful gases and malodorant components, and these materials will respread through the filter unit.

Oxidizers in the prior art suffer from a similar drawback to filters in that they are consumable; they are used up as they work and must be replaced from time to time to maintain their efficacy.

Photocatalysts in the prior art are largely effective in the UV spectrum, although visible spectrum photocatalysts are being synthesized. The increase in indoor lighting that is UV-free leads to a growing need for photocatalysts that are effective in the visible spectrum.

The discussed shortcomings of the technologies currently in use show there is a need for a more effective visible-spectrum photocatalyst.

SUMMARY OF INVENTION

In accordance with the purposes of the present invention, as embodied and broadly described herein, embodiments of the present invention includes a photocatalytic element for decomposing contaminants, including, but not limited volatile organic compounds and/or gases, inorganic compounds and or gases, and a method of purifying the air by decomposing contaminants in the air, and a method of extending the stock life of ethylene-sensitive plants by reducing the concentration of ethylene gas using said photocatalytic element. Herein, the photocatalytic element refers to an element that comprises at least a photocatalytic composition.

The embodiments include a filter element for decomposing contaminants comprising a substrate and a photocatalytic composition comprising at least a photocatalyst, which may be used to effectively reduce contaminants in the air by decomposing and/or oxidizing a contaminant when the photocatalytic element is illuminated by light and in contact with a contaminant. The embodiments can be more effective at reducing volatile organic compounds and/or gases, inorganic compounds and or gases levels, e.g., ethylene, than the filters and compositions used in the prior art. In some embodiments, the photocatalytic composition may be disposed over a substrate. In some embodiments, the substrate is a gas permeable support. In some embodiments, the photocatalyst shows visible light responsiveness. In some embodiments, said photocatalyst comprises $WO_3$, $TiO_2$, or $Ti(O,C,N)_2$:Sn. In some embodiments, the photocatalytic composition further comprising a co-catalyst. In some embodiments, said co-catalyst comprises anatase $TiO_2$, $SrTiO_3$, $KTaO_3$, or $KNbO_3$. In some embodiments, said co-catalyst comprises $In_2O_5$, $Ta_2O_5$, anatase $TiO_2$, rutile $TiO_2$, a combination of anatase and rutile $TiO_2$, or $CeO_2$. In some embodiments, the photocatalyst contains $WO_3$, and the co-catalyst contains $CeO_2$. In some embodiments, the photocatalyst contains $TiO_2$ or $SnO_2$, the co-catalyst contains $Cu_2O$ and/or $CuO$, and the co-catalyst is supported on the photocatalyst. In some embodiments, the filter element further comprises a fluororesin porous layer laminated on at least one surface of the substrate, and the photocatalytic composition is disposed on the fluororesin porous layer. In some embodiments, a fluororesin constituting the fluororesin porous layer contains polytetrafluoroethylene. In some embodiments, the photocatalytic composition is formed on the fluororesin porous layer through an aerosol deposition method.

The embodiments include a system for decomposing contaminants comprising a substrate and a photocatalytic composition comprising at least a photocatalyst. In some embodiments, said substrate defines a volume. In some embodiments, the system further comprises an enclosing element, wherein said substrate is disposed within said enclosing element. In some embodiments, the system further comprises a source of electromagnetic radiation that is in optical communication with said photocatalytic composition. In some embodiments, the system further comprises an airflow element for creating an airflow, said airflow element being disposed within said enclosing element. In some embodiments, the photocatalyst shows visible light responsiveness. In some embodiments, said photocatalyst comprises $WO_3$, $TiO_2$, or $Ti(O,C,N)_2$:Sn. In some embodiments, the photocatalytic composition further comprises a co-catalyst. In some embodiments, said co-catalyst comprises anatase $TiO_2$, $SrTiO_3$, $KTaO_3$, or $KNbO_3$. In some embodiments, said co-catalyst comprises $In_2O_5$, $Ta_2O_5$, anatase $TiO_2$, rutile $TiO_2$, a combination of anatase and rutile $TiO_2$, or $CeO_2$. In some embodiments, the photocatalyst contains $WO_3$, and the co-catalyst contains $CeO_2$. In some embodiments, the photocatalyst contains $TiO_2$ or $SnO_2$, the co-catalyst contains $Cu_2O$ and/or $CuO$, and the co-catalyst is supported on the photocatalyst. In some embodiments, the system may further comprise at least one additional filtering element. In some embodiments, the at least one additional filtering element can comprise a pre-filter element. In some embodiments, the at least one additional filtering element can comprise a HEPA/ULPA filter. In some embodiments, the at least one additional filtering element can comprise activated carbon.

The embodiments include a method comprising the steps of placing the above-mentioned system in atmospheric communication with an ethylene-sensitive plant; and reducing the amount of ethylene to a concentration below a threshold by contacting ethylene with the photocatalytic composition while said photocatalytic composition is illuminated by electromagnetic radiation comprising a wavelength sufficient to activate the photocatalytic composition. In an embodiment, the method further comprises the step of maintaining the concentration of ethylene below said threshold.

The embodiments comprise a method of placing the system in atmospheric communication with ethylene-sensitive plants and illuminating the photocatalytic element with light such that the photocatalytic element decomposes and/or oxidizes ambient ethylene, reducing ethylene levels in the air.

The embodiments comprise a method of reducing contaminant levels in the air comprising directing an airflow such that the air contacts the photocatalytic element while the photocatalytic element is illuminated with light sufficient to activate the photocatalytic element and decompose and/or oxidize contaminants in the air.

BRIEF DESCRIPTION OF DRAWINGS

FIG. 17A is a graph of the removal of acetaldehyde by the Comparative Example 48 filter and a photocatalytic filter embodiment of Example 47.

FIG. 17B is a graph of the removal of ethylene by the Comparative Example 48 filter and a photocatalytic filter embodiment of Example 47.

FIG. 18 is a table of the results of acetaldehyde and ethylene decomposition test of Examples 47 and Comparative Example 48.

FIG. 19 is a table of the results of varying filter thickness and light intensity test results of Example 49.

DESCRIPTION OF EMBODIMENTS

Figure 1:
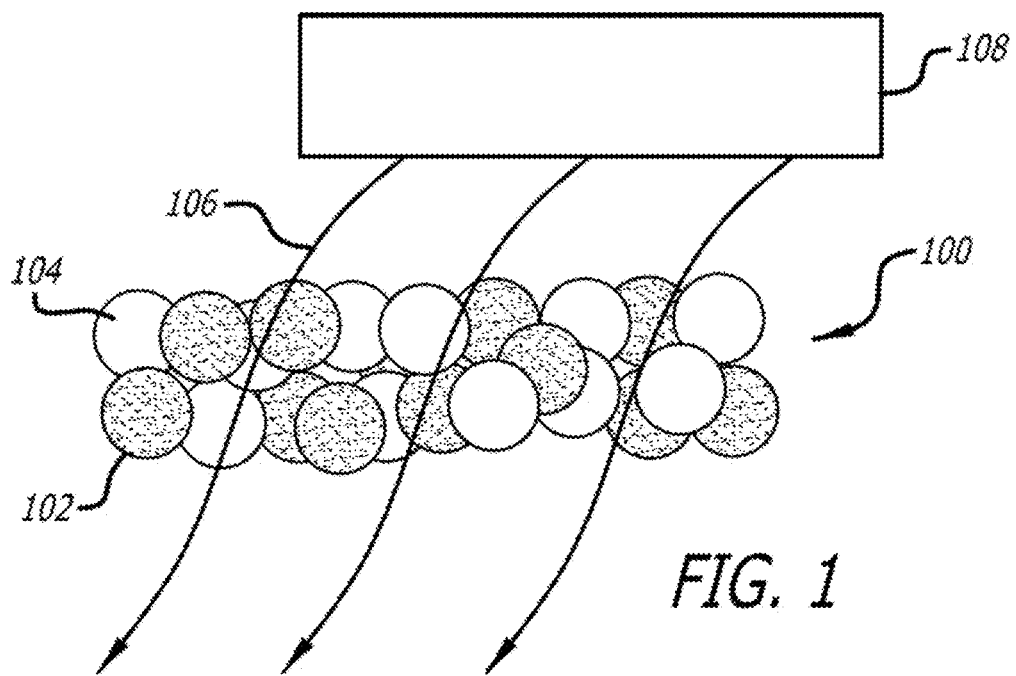
FIG. 1 is a schematic depiction of an embodiment of a photocatalytic coating.

Some embodiments of the filter element for decomposing contaminants in air decompose contaminants, including VOCs. In some embodiments, the decomposed contaminants can be ethylene, acetaldehyde, propanal, toluene and/or any combinations thereof. Herein, in the present specification, the term "filter element" has a concept including, for example, "filter medium". Some embodiments of the filter element for decomposing contaminants comprise a substrate and a photocatalytic composition. In some embodiments, the photocatalytic composition can comprise at least a photocatalyst. In some embodiments, the photocatalytic composition can comprise at least a first photocatalyst, a second photocatalyst and a co-catalyst. In some embodiments, the photocatalytic composition comprises at least a photocatalyst and a co-catalyst. In some embodiments, the photocatalytic composition can be anti-microbial. In some embodiments, the photocatalytic composition can decompose VOCs. In some embodiments, the photocatalytic composition can decompose VOCs and be antimicrobial. In some embodiments, the substrate may be gas impermeable, may be gas permeable, or may have porosity sufficient to allow air to flow through the element. In some embodiments, the photocatalytic composition is disposed upon, contacted with, and/or interposed between the substrate and the VOC carried material.

In some embodiments, the element comprising at least a photocatalyst can decompose, oxidize, neutralize and/or remove volatile organic compounds, inorganic compounds and/or gases and/or microbes from the air. In some embodiments the volatile organic compounds, inorganic compounds and/or gases, and/or microbes can be selected from ethylene, butyric acid, Geosmin, dimethyl sulfide or octenol, acids (NOx, SOx, HCl, HF, $H_2SO_4$), bases (amines, methylamine, triethylamine, $NH_3$, NMP), condensables (toluol, 2-propanol, silicones, xylene, heptanes, benzene, siloxanes, BHT), dopants ($AsH_3$ [arsine], $B_2H_6$ [diborane], $BF_3$ [boron trifluoride], organophosphates, e.g., triethyl phosphate [TEP], tris(2-chloroethyl)phosphate [TCEP], phosphoric acid, phosphonic acid, phosphinic acid, and/or phosphine oxide), hydrogen peroxide [$H_2O_2$], acetone, ozone [$O_3$], isopropyl alcohol [IPA], hydrogen sulfide [$H_2S$]). In some embodiments, the inorganic compounds or gases can be hydrogen peroxide ($H_2O_2$), organophosphates, acids, sulfides, and microbes in the air.

A photocatalyst includes any material that can activate or change the rate of a chemical reaction as a result of exposure to light, such as ultraviolet or visible light. In some embodiments, the photocatalyst can activate or change the rate of a chemical reaction as a result of exposure to visible light. A co-catalyst includes a material that enhances the photocatalytic properties of a photocatalyst. Co-catalysts may also be generically referred to as T-Binders throughout this document. Additionally, T-binders are described in U.S. patent application Ser. No. 13/738,243, filed Jan. 10, 2013 (United States Patent Publication US 2013/0180932, published Jul. 18, 2013) which is hereby incorporated in its entirety by reference.

In some embodiments, a photocatalytic element is described, comprising a substrate and a photocatalytic composition. Some embodiments describe a system for removing or decomposing a VOC that includes a substrate and a photocatalytic composition. In some embodiments, the system can be for plant preservation. In some embodiments, the photocatalytic composition comprises at least a photocatalyst. In some embodiment, the photocatalytic composition comprises at least a photocatalyst and a co-catalyst. In some embodiments, the substrate defines a volume. In some embodiments, the system further comprises an enclosing element, wherein the substrate is disposed within the enclosing element.

In some embodiments, the system further comprises a source of electromagnetic radiation that is in optical communication with said photocatalytic composition. In some embodiments, the system further comprises an airflow element for creating an airflow, said airflow element being disposed in fluid communication with said enclosing element. In some embodiments, the airflow element can be disposed within said enclosing element, or fixedly attached thereto. In some embodiments, the system can further comprise at least one additional filter element. In some embodiments, the at least one additional filter element can be a prefilter, a HEPA/ULPA, a substrate sans the photocatalytic composition and/or an activated carbon filter, and/or combinations of the aforedescribed filter elements.

In some embodiments, the photocatalytic composition can be disposed on any combination of elements to the system. In some embodiments the photocatalytic composition can be disposed on and/or within the surface of the pre-filter, on the filter, on the enclosing element, on the surfaces of the airflow element, e.g., on the blades of a fan, and/or on any other surface of the system in optical communication with the electromagnetic radiation source.

In some embodiments, the system for decomposing contaminants comprises an enclosing element having a first end and a second end, the second end opposite from said first end. Between the first end and the second end, in some embodiments the system may comprise an airflow element for generating an airflow. In some embodiments, the system may comprise a source of electromagnetic radiation that emits electromagnetic radiation at least in a wavelength capable of activating the photocatalytic composition of the element for decomposing contaminants. In some embodiments, the system may comprise an element for decomposing contaminants.

Photocatalysts are a substance that shows photocatalytic activity upon being irradiated with light of specific wavelengths (excitation light having a higher energy than the band gap between the valence and the conduction band of the photocatalyst). Since photocatalysts shows photocatalytic activity, they can exhibit a wide range of effects, including air refreshment and deodorizing effect, decomposition of harmful substances such as volatile organic compounds (VOCs), and antimicrobial effect.

In some embodiments the photocatalyst material may be an inorganic solid, such as a solid Inorganic semiconductor, that absorbs ultraviolet or visible light. For some materials, photocatalysis may be due to reactive species (able to perform reduction and oxidation) being formed on the surface of the photocatalyst from the electron-hole pairs generated in the bulk of the photocatalyst by said absorption of electromagnetic radiation. In some embodiments, the photocatalyst has a conduction band with an energy of about 1 eV to about 0 eV, about 0 eV to about −1 eV, or about −1 eV to about −2 eV, as compared to the normal hydrogen electrode. Some photocatalyst may have a valence band with energy of about 3 eV to about 3.5 eV, about 2.5 eV to about 3 eV, or about 2 eV to about 3.5 eV, or about 3.5 eV to about 5.0 eV as compared to the normal hydrogen electrode. In some embodiments, the photocatalytic material comprises a copper loaded oxide. Suitable copper loaded oxides are described in U.S. patent application Ser. No. 13/840,859 filed Mar. 15, 2013; and U.S. Provisional Application, 61/835,399, filed Jun. 14, 2013, which are incorporated by reference in their entireties. Copper loaded oxides can exhibit anti-bacterial effects.

Some photocatalysts can be activated only by light in the UV regime i.e. wavelength less than 380 nm. This is because of the wide bandgap (>3 eV) of most semiconductors. However, in recent years by appropriately selecting materials or modifying existing photocatalysts, visible light photocatalysts have been synthesized (Asahi et al., Science, 293: 269-271, 2001 and Abe et al., Journal of the American Chemical Society, 130(25): 7780-7781, 2008). A visible light photocatalyst Includes a photocatalyst which is activated by visible light, e.g. light that is normally visually detectable by the unaided human eye, such as at least about 380 nm in wavelength. In some embodiments, visible light photocatalysts can also be activated by UV light below 380 nm in wavelength in addition to visible wavelengths. Some visible light photocatalyst may have a band gap that corresponds to light in the visible range, such as a band gap greater than about 1.5 eV, less than about 3.5 eV, about 1.5 eV to about 3.5 eV, about 1.7 eV to about 3.3 eV, or 1.77 eV to 3.27 eV. Some photocatalysts may have a band gap of about 1.2 eV to about 6.2 eV, about 1.2 eV to about 1.5 eV, or about 3.5 eV to about 6.2 electron eV.

It is preferable that the photocatalyst contains a metallic compound (such as an oxide, a nitride oxide, an oxynitride carbide, or a halide), and more preferably contains a titanium compound, a tin compound, or a tungsten compound.

Some photocatalysts include oxide semiconductors such as $TiO_2$, ZnO, $WO_3$, $SnO_2$, etc., and modifications thereof. Contemplated modifications include doping and/or loading. Other materials like complex oxides ($SrTiO_3$, $BiVO_4$) and some sulfides (CdS, ZnS), nitrides (GaN) and some oxynitrides (e.g. ZnO:GaN) may also display photocatalytic properties. Photocatalysts can be synthesized by those skilled in the art by a variety of methods including solid state reaction, combustion, solvothermal synthesis, flame pyrolysis, plasma synthesis, chemical vapor deposition, physical vapor deposition, ball milling, and high energy grinding.

The average oxidation number or formal charge of titanium in the titanium compound is preferably +1 to +6, more preferably +2 to +4, further preferably +1 to +3. The average oxidation number or formal charge of tin in the tin compound is preferably +2 to +8, more preferably +1 to +6, further preferably +1 to +4. The average oxidation number or formal charge of tungsten in the tungsten compound is preferably +1 to +8, more preferably +1 to +6, further preferably +1 to +4.

More specifically, the photocatalyst preferably contains at least one selected from titanium(IV) oxide ($TiO_2$), tin(IV) oxide ($SnO_2$), tungsten(III) oxide ($W_2O_3$), tungsten(IV) oxide ($WO_2$), and tungsten(VI) oxide ($WO_3$). As the titanium(IV) oxide ($TiO_2$), an anatase-type titanium(IV) oxide ($TiO_2$) is preferred.

Incidentally, in the present specification, the phrase that "the photocatalyst contains (or comprises) tungsten(VI) oxide ($WO_3$)" Includes not only a case where the photocatalyst is a pure tungsten(VI) oxide ($WO_3$) but also a case where the photocatalyst contains a tungsten(VI) oxide ($WO_3$) doped with another element or compound. (The same applies to photocatalysts and co-catalysts other than tungsten oxide.)

Especially, it is preferable that the photocatalyst contains tungsten(VI) oxide ($WO_3$) because it makes it possible to form a photocatalyst layer that shows a sufficient photoactivity with visible light.

In some embodiments, the respective Ti or W compounds can be a respective oxide, oxycarbide, oxynitride, oxyhalide, halide, salt, doped or loaded compound. In some embodiments, the respective Ti or W compounds can be $TiO_2$, $WO_3$, or $Ti(O,C,N)_2$:Sn, such as $Ti(O,C,N)_2$:Sn wherein the molar ratio of Ti:Sn is about 90:10 to about 80:20, about 85:15 to about 90:10, or about 87:13. Suitable $Ti(O,C,N)_2$:Sn compounds are described in U.S. patent application Ser. No. 13/738,243, filed Jan. 10, 2013 (United States Patent Publication US2013/0180932, published Jul. 18, 2013), which is incorporated by reference in its entirety. In some embodiments, the respective Ti or W compounds can be nanopowders, nanoparticles, and or layers comprising the same. In some embodiments, examples of the photocatalyst may include metal oxides such as tungsten(III) oxide ($W_2O_3$), tungsten(IV) oxide ($WO_2$), tungsten(VI) oxide ($WO_3$), zinc oxide (ZnO), zirconium oxide ($ZrO_2$), tin(II) oxide (SnO), tin(IV) oxide ($SnO_2$), tin(VI) oxide ($SnO_3$), cerium(II) oxide (CeO), cerium(IV) oxide ($CeO_2$), strontium titanate ($SrTiO_3$), barium titanate ($BaTiO_3$), indium(III) oxide ($In_2O_3$), bismuth vanadate ($BiVO_4$), iron(III) oxide ($Fe_2O_3$), bismuth (III) oxide ($Bi_2O_3$), copper(I) oxide ($Cu_2O$), copper(II) oxide (CuO), $Cu_xO$, potassium tantalate ($KTaO_3$), and potassium niobate ($KNbO_3$); metal sulfides such as cadmium sulfide (CdS), zinc sulfide (ZnS), and indium sulfide (InS); metal selenides such as cadmium selenate ($CdSeO_4$), and zinc selenide (ZnSe); and metal nitrides such as gallium nitride (GaN). $Cu_xO$ is described in U.S. patent application Ser. No. 13/840,859 which is hereby incorporated in its entirety by reference. In some embodiments, the photocatalyst comprises $TiO_2$. In some embodiments, the photocatalyst comprises anatase and/or rutile titanium(IV) oxide ($TiO_2$). In some embodiments, the photocatalyst does not include $TiO_x$. In some embodiments, the photocatalyst does not include $TiO_2$. In some embodiments, the photocatalyst comprises $WO_3$.

Any useful amount of photocatalyst may be used. In some embodiments, the photocatalyst material is about 0.01 molar % to 100 molar %, or at least about 0.01 molar % and less than 100 molar % of the composition. In some embodiments, the photocatalyst material is about 20 molar % to about 80 molar %, about 30 molar % to about 70 molar %, about 40 molar % to about 60 molar %, or about 50 molar % of the composition.

Photocatalysts such as $TiO_2$ and $WO_3$ compounds, e.g., nanopowders, can be prepared by many different methods including plasma synthesis such as thermal plasma (direct current and including radio frequency inductively-coupled plasma (RF-ICP)), solvothermal, solid state reaction, pyrolysis (spray and flame), and combustion. Radio frequency inductively-coupled plasma (e.g. thermal) methods as described in U.S. Pat. No. 8,003,563, which is hereby incorporated in its entirety by reference, may be useful because of low contamination (no electrodes) and high production rates and facile application of precursors either in the gas, liquid or solid form. Hence, radio frequency inductively-coupled plasma processes are preferred. For example, when preparing $WO_3$ nanopowders, a liquid dispersion of ammonium metatungstate in water (5-20 wt % solid in water) can be sprayed into the plasma volume using a two-fluid atomizer. Preferably, the precursor can be present to about 20 wt % solid in water. The plasma can be operated at about 25 kW plate power with argon, nitrogen and/or oxygen gases. The particles formed from the condensed vapor from the plasma can then be collected on filters. In some embodiments, the particle surface areas range as measured using BET from about 1 $m^2/g$ to about 500 $m^2/g$, about 15 $m^2/g$ to 30 $m^2/g$, or about 20 $m^2/g$. In some embodiments, the obtained $WO_3$ may be heated from about 200° C. to about 700° C. or about 300° C. to about 500° C.

In some embodiments, a photocatalyst can be doped with at least one naturally occurring element e.g. non-noble gas elements, to improve the activity of the photocatalyst. Such an element may be called a "dopant". Doped elements (dopants) can be provided as precursors added generally during synthesis. Doped elements (dopants) can be elements that are incorporated into the crystal lattice of the Ti or W compound, for example as substituted within defined positions within the crystal lattice or otherwise interstitially included within the crystal. In some embodiments, the dopant can be selected from one of more elements including alkali metals such as lithium (Li), sodium (Na), potassium (K), and cesium (Cs); alkali earth metals such as magnesium (Mg), calcium (Ca), strontium (Sr), barium (Ba); noble metals such as gold (Au), platinum (Pt), rhodium (Rh), iridium (Ir), palladium (Pd), and ruthenium (Ru); transition metals such as iron (Fe), copper (Cu), zinc (Zn), vanadium (V), titanium (Ti) (for example for W-based compounds), tungsten (W) (for example for Ti-based compounds), manganese (Mn), Mo, zirconium (Zr), niobium (Nb), chromium (Cr), cobalt (Co), cerium (Ce) and nickel (Ni); lanthanide and actinide metals; halogens; Group III elements (from the Dmitri Mendeleev/Lothar Meyer style modern periodic table with elements arranged according to increasing atomic number) including B, Al, Ga, In and Ti, Group IV elements including Ca, Si, Ge, Sn; Group V elements like N, P, As, Bi; and Group VI elements like S and Se. In some embodiments, the photocatalyst can be doped with at least one element selected from C, N, S, F, Sn, Zn, Mn, Al, Se, Nb, Ni, Zr, Ce and Fe. In some embodiments, the photocatalyst may be self-doped, e.g., $Ti^{3+}$ in place of $Ti^{4+}$ in a $TiO_2$ matrix. Details of suitably doped photocatalytic materials are presented in the U.S. Provisional Patent Application No. 61/587,889, which is hereby incorporated by reference in its entirety. In this specification, a photocatalyst doped with a dopant may be referred to as "doped-type photocatalyst".

The term "doping" means adding an arbitrarily chosen element (dopant) to the host compound crystals within a range that essentially does not change the basic crystalline structure of the photocatalyst. Whether the photocatalyst is doped or not can be confirmed by, for example, a peak shift in XPS (X-ray photoelectron spectroscopy). Methods used for forming the doped-type photocatalyst are not particularly limited, and may be, for example, a sol-gel method, a solid-phase reaction method, and an ion implantation method.

When the photocatalyst is a doped-type photocatalyst, the molar ratio of the host compound (compound subjected to doping) and the dopant in the photocatalyst is not particularly limited, and is preferably 99.9:0.1 to 80:20, more preferably 99.9:0.1 to 85:15, further preferably 99.9:0.1 to 87:13.

Preferably, the doped-type photocatalyst is doped with at least one selected from carbon (C), nitrogen (N), sulfur (S), fluorine (F), tin (Sn), zinc (Zn), manganese (Mn), aluminum (Al), selenium (Se), niobium (Nb), nickel (Ni), zirconium (Zr), cerium (Ce), and iron (Fe).

The photocatalyst may be a p-type or an n-type. A p-type photocatalyst may be obtained, for example, by doping a photocatalyst with high valance elements (for example, such as arsenic (As)). An n-type photocatalyst may be obtained, for example, by doping a photocatalyst with low valence elements (for example, such as boron (B)).

In some embodiments, the photocatalytic material can comprise one or more of n-type UV photocatalytic material, n-type visible light photocatalytic material, p-type UV photocatalytic material and/or p-type visible photocatalytic material. In some embodiments, the n-type visible band gap semiconductors can optionally be $WO_3$, $Ti(O,C,N)_2$:Sn, or $CeO_2$. In some embodiments, the n-type UV photocatalytic material can optionally be $CeO_2$, $TiO_2$, $SnO_2$, $SrTiO_3$, $ATaO_3$, $ANbO_3$ etc.; A=alkali metal ion, wherein A can Ca, Ba, and/or Sr. In some embodiments, p-type visible band gap semiconductors can optionally be SiC, $CuMO_2$, M=Al, Cr. In some embodiments, the p-type UV photocatalytic material can optionally be $ZnIrO_2$, $ZnRhO_2$, CuO, NiO, $Mn_2O_3$, $Co_3O_4$, and/or $Fe_2O_3$.

In some embodiments, the photocatalyst can be loaded with at least one metal. Loaded elements can be provided by post synthesis methodologies like impregnation (Liu, M., Qiu, X., Miyauchi, M., and Hashimoto, K., *Cu(II) Oxide Amorphous Nanocausters Grafted $Ti^{3+}$ Self-Doped $TiO_2$: An Efficient Visible Light Photocatalyst*. Chemistry of Materials, published online 2011), photo-reduction (Abe et al., Journal of the American Chemical Society, 130(25): 7780-7781, 2008), and sputtering. Loading metals on photocatalysts may be carried out as described in US Patent Publication Number US2008/0241542 which is incorporated here in its entirety by reference. In some embodiments, the loaded element is selected from noble elements. In some embodiments, the loaded element can be selected from at least one noble element, oxide, and/or hydroxide. In some embodiments, the noble elements can be selected from Au, Ag, Pt, Pd, Ir, Ru, Rh or their oxides and/or hydroxides. In some embodiments, the loaded element is selected from transition metals, their oxides and/or hydroxides. In some embodiments, the loaded element is selected from Fe and Cu and Ni or their oxide and hydroxides. In some embodiments, the loaded elements may be chosen from different groups of elements including at least one transition metal and at least one noble metal or their respective oxides and hydroxides. In some embodiments, a suitable loaded metal oxide is described in U.S. patent application Ser. No. 13/840,859 filed Mar. 15, 2013; and U.S. Provisional Application, 61/835,399, filed Jun. 14, 2013, which are incorporated by reference in their entireties.

In some embodiment, the photocatalyst preferably has a refractive index (R1) of 1.0 to 4.0, more preferably 1.0 to 3.0, particularly preferably 1.5 to 2.5 at a wavelength of 589 nm. With the photocatalyst refractive index (R1) falling in the range of 1.0 to 4.0, it becomes easier to reduce the refractive index difference from the co-catalyst, and thus becomes easier to form a translucent photocatalyst layer. Note that the refractive index values of the photocatalyst are measured values obtained with an Abbe refractometer according to the "Solid Sample Measurement Method" specified by JIS K 0062.

The shape of the photocatalyst is not particularly limited, and the photocatalyst is preferably particulate in shape.

Many kinds of photocatalysts are poorly soluble in solvent. With the particulate shape, the photocatalyst can be dispersed in a dispersion medium to produce a dispersion liquid, which can then be used to easily form the photocatalyst layer by being coated and dried.

When the photocatalyst is particulate in shape, the average particle size of the photocatalyst is not particularly limited, and is preferably 5 nm to 1,000 nm, more preferably 5 nm to 100 nm, further preferably 5 nm to 30 nm. When the average particle size of the photocatalyst exceeds 1,000 nm, the overall surface area of the photocatalyst becomes smaller, and the photocatalyst layer may fail to sufficiently show photocatalytic activity. On the other hand, when the average particle size of the photocatalyst falls below 5 nm, particle aggregation tends to occur, and the translucency of the photocatalyst layer may suffer.

Note that the average particle size of the photocatalyst is a volume-based 50% cumulative distribution diameter (D50) of photocatalyst particles dispersed in an arbitrary dispersion liquid as determined by dynamic light scattering frequency analysis (FFT-heterodyne method).

Co-catalysts are a substance that accelerate the photocatalytic activity of the photocatalyst. The photocatalyst layer according to the present invention may further contain a co-catalyst, in addition to the photocatalyst, as desired. The co-catalyst may be one that shows or does not show photocatalytic activity by itself. In cooperation with the photocatalyst, the co-catalyst can increase the reaction rate of the photocatalyst by 1.2 fold or more, preferably 1.5 fold or more, further preferably 2.0 fold or more, particularly preferably 3.0 fold or more from that when the photocatalyst is used alone. The reaction rate of the photocatalyst may be based on, for example, the decomposition rate of acetaldehyde, a type of volatile organic compounds (VOCs). Co-catalysts may also be generically referred to as T-Binder throughout this document.

Specifically, the photocatalyst, either alone or with the co-catalyst mixed with or supported by the photocatalyst, is put in a closed space charged with certain quantities of compressed air and acetaldehyde (calibration gas), and irradiated with visible light (wavelength 455 nm, irradiation intensity 200 mW/cm$^2$) for 1 hour. The acetaldehyde concentrations in the dosed space before and after the irradiation are then compared to calculate the factor by which the reaction rate of the photocatalyst increased. For example, the acetaldehyde decomposition rate can be said to have increased 3 fold (a 3-fold increase of photocatalytic activity) when the acetaldehyde concentration in a closed space charged with the photocatalyst and the co-catalyst (either mixed with the photocatalyst or supported on the photocatalyst) becomes 20 ppm after the irradiation of the closed space containing 80 ppm of acetaldehyde (i.e., 60 ppm of acetaldehyde has decomposed) as compared to when the acetaldehyde concentration in a closed space charged with the photocatalyst alone becomes 60 ppm after the irradiation of the closed space containing 80 ppm of acetaldehyde (i.e., 20 ppm of acetaldehyde has decomposed).

Some co-catalyst may be compounds or semiconductors that are capable of being reduced by electron transfer from the conduction band of the photocatalyst. For example, a co-catalyst may have a conduction band having a lower energy than the conduction band of the photocatalyst, or a co-catalyst may have a lowest unoccupied molecular orbital having a lower energy than the conduction band of the photocatalyst. When a term such as "lower energy" and "higher energy" is used to compare a band of a semiconductor or a molecular orbital with another band or molecular orbital, it means that an electron loses energy when it is transferred to the band or molecular orbital of lower energy, and an electron gains energy when it is transferred to the band for molecular orbital of higher energy.

The co-catalyst may be simply mixed with the photocatalyst, or may be supported on the photocatalyst. In this specification, a photocatalyst supporting the co-catalyst is referred to as "supporting-type photocatalyst". As used herein, the term "supporting" refers to the state where a substance different from the photocatalyst is adhering to the photocatalyst surface. Such an adhering state can be observed, for example, by scanning electron microscopy. Methods used for forming the supporting-type photocatalyst are not particularly limited, and may be, for example, an impregnation method, a photoreduction method, or sputtering. The supporting-type photocatalyst may be formed by using the method described in, for example, US Patent Application 2008/0241542. The co-catalyst may be doped with a dopant. A co-catalyst doped with a dopant will be referred to as doped-type co-catalyst. The compounds and elements used to dope the co-catalyst are as exemplified above in conjunction with the photocatalyst.

It is believed that some metal oxides that are co-catalysts are capable of reducing $O_2$. For example, it is believed that $CeO_2$ can reduce $O_2$ gas by electron transfer. In doing so, it is believed that $Ce^{3+}$ transfers an electron to $O_2$ and is converted to $Ce^{4+}$ as a result. In a photocatalyst composition, a photocatalyst may transfer an electron to $CeO_2$, thus converting $Ce^{4+}$ to $Ce^{3+}$, and the $Ce^{3+}$ may then reduce $O_2$. $Ce^{3+}$ may also be present as a result of equilibrium processes involving $CeO_2$ and $O_2$, and superoxide radical ion ($O_2.^-$). $O_2$ and superoxide radical ion in such an equilibrium process may be adsorbed to the surface of solid $CeO_2$ or present in the atmosphere. $Ce^{3+}$ may also be present as a result of oxidation and reduction reactions with cerium species of different oxidation states that may be added intentionally or present as impurities.

Some co-catalysts may be capable of converting atmospheric $O_2$ to superoxide radical ion. For example, $CeO_2$ is capable of converting atmospheric oxygen to superoxide radical ion. It is believed that some of the equilibrium and/or electron transfer processes described above may contribute to this property of $CeO_2$. Such a conversion may occur under a variety of conditions, such as ambient conditions, including for example, normal atmospheric oxygen concentrations, such as molar concentrations of about 10% to about 30%, about 15% to about 25%, or about 20% oxygen; ambient temperature, such as about 0° C. to about 1000° C., about 0° C. to about 100° C., about 10° C. to about 50° C., or about 20° C. to about 30° C.; and pressure, such as about 0.5 to about 2 atm, about 0.8 atm to about 1.2 atm, or about 1 atm. Such a conversion may also occur under elevated or reduced temperature, pressure, or oxygen concentration. Other materials that may be capable of reducing $O_2$ or converting atmospheric $O_2$ to superoxide radical ion include various other materials such as $Ce_xZr_yO_2$ (where x/y=0.99-0.01), $BaYMn_2O_{5+\delta}$, and lanthanide-doped $CeO_2$ including $Ce_xZr_yLa_zO_2$, $Ce_xZr_yPr_zO_2$, and $Ce_xSm_yO_2$.

Some co-catalysts may have a valence band or a highest occupied molecular orbital at a higher energy than a valence band of the photocatalyst. This may allow a hole in a valence band of the photocatalyst to be transferred to a highest occupied molecular orbital or a valence band of the co-catalyst. The hole in the valence band or highest occupied molecular orbital of co-catalyst may then oxidize $H_2O$ or $OH^-$ to OH. For example, if $WO_3$ is chosen as a photocatalyst, examples of such a co-catalyst may include anatase $TiO_2$, $SrTiO_3$, $KTaO_3$, SiC or $KNbO_3$.

In some embodiments, the co-catalyst can be inorganic. In some embodiments, the inorganic co-catalyst can be a binder. In some embodiments, the co-catalyst can be an oxide, such as a metal dioxide, including $CeO_2$, $TiO_2$, or the like. Suitable co-catalysts are described in U.S. patent application Ser. No. 13/738,243, filed Jan. 10, 2013 (United States patent Publication, US2013/180932, published Jul. 18, 2013), which is incorporated by reference in its entirety.

In some embodiments, examples of the co-catalyst may include copper(I) oxide ($Cu_2O$), copper(II) oxide (CuO), molybdenum(VI) oxide ($MoO_3$), manganese(III) oxide ($Mn_2O_3$), yttrium(III) oxide ($Y_2O_3$), gadolinium(III) oxide ($Gd_2O_3$), anatase-type and/or rutile-type titanium(IV) oxide ($TiO_2$), strontium titanate ($SrTiO_3$), potassium tantalate ($KTaO_3$), silicon carbide (SiC), potassium niobate ($KNbO_3$), silicon oxide ($SiO_2$), tin(IV) oxide ($SnO_2$), aluminum(III) oxide ($Al_2O_3$), zirconium oxide ($ZrO_2$), iron(III) oxide ($Fe_2O_3$), iron(II, III) oxide ($Fe_3O_4$), nickel(II) oxide (NiO), niobium(V) oxide ($Nb_2O_5$), indium oxide ($In_2O_5$), tantalum oxide ($Ta_2O_5$), cerium(II) oxide (CeO), cerium(IV) oxide ($CeO_2$), $A_rX_tO_s$ (where A is a rare earth element, X is an element other than rare earth elements, or a combination of elements other than rare earth elements, r is 1 to 2, t is 0 to 3, and s is 2 to 3), ammonium phosphomolybdate trihydrate (($NH_4)_3[PMo_{12}O_{40}]$), 12-tungstophosphoric acid ($PW_{12}O_{40}$), tungsten silicide ($H_4[SiW_{12}O_{40}]$), phosphomolybdic acid ($12MoO_3 \cdot H_3PO_4$), and cerium-zirconium composite oxide ($Ce_xZr_yO_2$) (y/x=0.001 to 0.999). In some embodiments, the co-catalyst comprises $In_2O_5$, $Ta_2O_5$, anatase $TiO_2$, rutile $TiO_2$, a combination of anatase and rutile $TiO_2$, or $CeO_2$. In some embodiments, the co-catalyst comprises $TiO_2$. In some embodiments, the co-catalyst comprises anatase $TiO_2$. In some embodiments, the co-catalyst does not include $Cr_2O_3$, $CeO_2$, $Al_2O_3$, or $SiO_2$. In some embodiments, the co-catalyst does not include $Cr_2O_3$. In some embodiments, the co-catalyst does not include $CeO_2$. In some embodiments, the co-catalyst does not include $Al_2O_3$. In some embodiments, the co-catalyst does not include $SiO_2$.

In some embodiments, the co-catalyst can be $Re_rE_tO_s$, $Re_rE_tO$, or $Re_rE_tO_2$, wherein in Re is a rare earth element, E is an element or a combination of elements, and O is oxygen; and r is 1 to 2, such as about 1 to about 1.5 or about 1.5 to about 2; s is 2 to 3, such as about 2 or about 3; and t is 0 to 3, such as about 0.01 to about 1, about 1 to about 2, or about 2 to about 3. In some embodiments, the co-catalyst can be $Re_rO_s$ where Re can be a rare earth metal and r can be greater than or equal to 1 and less than or equal to 2, or can be between 1 and 2, and s can be greater than or equal to 2 and less than or equal to 3, or can be between 2 and 3. Examples of suitable rare earth elements include scandium, yttrium and the lanthanide and actinide series elements. Lanthanide elements include elements with atomic numbers 57 through 71. Actinide elements include elements with atomic numbers 89 through 103. In some embodiments, the co-catalyst can be $Ce_xZr_yO_2$ wherein the y/x ratio=0.001 to 0.999.

The co-catalyst preferably contains at least one selected from a cerium compound, a copper compound, a potassium compound, a strontium compound, a tantalum compound, a niobium compound, and a titanium compound. More preferably, the co-catalyst contains a cerium compound, or a copper compound. The average oxidation number or formal charge of the cerium compound is preferably +2 to +4. The average oxidation number or formal charge of the copper compound is preferably +1 to +2. In some embodiments, the co-catalyst can be $CeO_a$ (a≤2). In some embodiments, the co-catalyst can be CeO. In some embodiments, the co-catalyst can be cerium oxide ($CeO_2$).

In some embodiments, the co-catalyst contains cerium oxide, more preferably cerium(IV) oxide ($CeO_2$). This embodiment is suited for use in decomposition of volatile organic compounds (VOCs). When the co-catalyst contains cerium(IV) oxide ($CeO_2$), it is preferable to dope the cerium (IV) oxide, preferably with tin (Sn). In the tin (Sn)-doped cerium(IV) oxide ($CeO_2$:Sn), the tin (Sn) accounts for preferably 1 mol % to 50 mol %, more preferably 1.5 mol % to 10 mol %, further preferably 1.5 mol % to 10 mol %, particularly preferably 1.5 mol % to 4.5 mol % of the total co-catalyst ($CeO_2$:Sn).

In some embodiments, the photocatalyst can be $WO_3$ and the co-catalyst can be $CeO_a$ (a≤2).

In some embodiments, the co-catalyst maybe a Keggin unit e.g. ammonium phosphomolybdate (($NH_4)_3$ $[PMo_{12}O_{40}]$), 12-phosphotungstic acid, silicotungstic acid and phosphomolybdic acid. The overall stability of the Keggin unit allows the metals in the anion to be readily reduced. Depending on the solvent, acidity of the solution and the charge on the α-Keggin anion, it can be reversibly reduced in one- or multiple electron step.

In some embodiments, the photocatalytic layer can be formed of the materials described herein.

While not wanting to be limited by theory, the inventors believe that $CeO_2$ may be useful in conjunction with tungsten oxide because of the relative band positions of these materials. Furthermore, it is noteworthy that the index of refraction of $CeO_2$ is substantially the same as tungsten oxide, about 90% to about 110%. In another embodiment about 95% to about 105%. In some embodiments, the high transparency of the photocatalytic compositions can provide a composition/layer/element of transparency greater than about 50%, 60%, 65% and/or 70%. The low scattering losses due to matched refractive indices contributes directly to a transparent composition.

In some embodiments, the co-catalyst contains copper oxide, more preferably copper(I) oxide ($Cu_2O$) and/or copper(II) oxide (CuO). This embodiment is suited for antimicrobial applications. When the co-catalyst contains copper(I) oxide ($Cu_2O$) and/or copper(II) oxide (CuO), it is preferable that the copper(I) oxide ($Cu_2O$) and/or copper(II) oxide (CuO) are supported on the photocatalyst.

The shape of the co-catalyst is not particularly limited, and the co-catalyst is preferably particulate in shape for the same reasons described for the photocatalyst. When the co-catalyst is particulate in shape, the average particle size of the co-catalyst is not particularly limited, and is preferably 1 nm to 1,000 nm, more preferably 1 nm to 100 nm, further preferably 1 nm to 30 nm.

The co-catalyst has a refractive index (R2) of preferably 1.0 to 4.0, more preferably 1.0 to 3.0, particularly preferably 1.5 to 2.5 at 589 nm wavelength. With the co-catalyst refractive index (R2) falling in the range of 1.0 to 4.0, it becomes easier to reduce the refractive index difference from the photocatalyst, and form a desirably translucent photocatalyst layer.

Examples of the photocatalyst described above Include a UV responsive photocatalyst that shows photocatalytic activity only with ultraviolet rays of less than 380 nm wavelength, and a visible-light responsive photocatalyst that shows photocatalytic activity also with visible light of 380 nm to 780 nm wavelengths. In the present invention, the photocatalyst contained in the photocatalyst layer may be a UV responsive photocatalyst or a visible-light responsive photocatalyst, and is preferably a visible-light responsive photocatalyst. The visible-light responsive photocatalyst shows some photoactivity with visible light even without the co-catalyst. The visible-light responsive photocatalyst, in cooperation with the co-catalyst, can thus show even higher photoactivity with visible light. When the photocatalyst is a visible-light responsive photocatalyst, the band gap is, for example, 1.5 eV to 3.5 eV, preferably 1.7 eV to 3.3 eV, more preferably 1.77 eV to 3.27 eV. Note that the photocatalyst may show a visible-light responsiveness in certain photocatalyst and co-catalyst combinations even when the photocatalyst is a UV responsive photocatalyst.

In some embodiments, the photocatalyst is preferably one that shows a visible-light responsiveness. A visible-light responsive photocatalyst can show photocatalytic activity also with a visible-light emitting light source such as a fluorescence lamp and an LED, and enables avoiding use of ultraviolet light, which can be harmful to the human body. Because a visible-light responsive photocatalyst allows the use of a visible-light emitting light source, a filter element using such a photocatalyst can be used in a wider range of applications such as in air cleaners, building materials, and deodorants.

Photocatalysts may be used either alone or as a mixture of two or more. When two or more photocatalysts are used as a mixture, one of the photocatalysts may function as the co-catalyst of the other photocatalyst. Co-catalysts may also be used alone or as a mixture of two or more.

The photocatalyst layer may contain other compounds (for example, such as a binder resin), in addition to the photocatalyst, or in addition to the photocatalyst and the co-catalyst. As is apparent, such additional compounds in the photocatalyst layer may involve a large refractive index difference from the photocatalyst or the co-catalyst, and sufficient translucency may not be ensured for the photocatalyst layer.

It is accordingly preferable that the photocatalyst layer is configured substantially solely from the photocatalyst, or from the photocatalyst and the co-catalyst. Photocatalyst layer being configured substantially solely from the photocatalyst, or from the photocatalyst and the co-catalyst, means that the photocatalyst, or the photocatalyst and the co-catalyst accounts for at least 80 mass %, preferably at least 90 mass % of the total photocatalyst layer.

When the photocatalyst layer contains the photocatalyst and the co-catalyst, any useful ratio of photocatalyst to co-catalyst may be used. When the photocatalyst layer contains the photocatalyst and the co-catalyst, the ratio (molar ratio) of the total photocatalyst and the total co-catalyst is preferably 99.5:0.5 to 16.7:83.3, more preferably 99.5:0.5 to 20:80, further preferably 99.5:0.5 to 50:50.

When the photocatalyst content is less than the lower limit of the foregoing ranges, the co-catalyst will be in excess of the photocatalyst amount, and the photocatalyst layer may fail to show sufficient photocatalytic activity. On the other hand, when the photocatalyst content exceeds the upper limit of the foregoing ranges, the co-catalyst will be deficient relative to the photocatalyst amount, and the photocatalyst layer may fail to show sufficient photocatalytic activity.

When the photocatalyst layer contains the photocatalyst and the co-catalyst, the absolute value of the difference between the photocatalyst refractive index (R1) and the co-catalyst refractive index (R2) at 589 nm wavelength (|R1-R2|) is preferably 0 to 0.35, more preferably 0 to 0.30, further preferably 0 to 0.20, particularly preferably 0 to 0.16.

Note that |R1-R2|=0 means that the photocatalyst refractive index (R1) and the co-catalyst refractive index (R2) are the same.

With the refractive index difference of the photocatalyst and the co-catalyst falling in the foregoing ranges, light more easily passes through the photocatalyst layer than being refracted therein (the photocatalyst layer will have increased translucency). This makes it possible to form a photocatalyst layer having superior translucency.

In the present invention, when the photocatalyst layer contains the photocatalyst and the co-catalyst, the combination of the photocatalyst and the co-catalyst contained in the photocatalyst layer is not particularly limited.

In some embodiments, a photocatalytic composition can comprise tungsten oxide and a rare earth oxide at a molar ratio of about 0.5:1 to 2:1 or about 1:1 (tungsten oxide:rare earth oxide). In some embodiments, the rare earth oxide is cerium oxide ($CeO_2$). In some embodiments, the photocatalytic composition may include $WO_3$ and $CeO_2$, having a molar ratio ($WO_3$:$CeO_2$) of about 1:5 to about 5:1, about 1:3 to about 3:1, about 1:2 to about 2:1, or about 1:1.

In a preferred embodiment, the photocatalyst contains tungsten(VI) oxide ($WO_3$), and the co-catalyst contains cerium(IV) oxide ($CeO_2$). A photocatalyst layer that is excellent in visible-light responsiveness and photocatalytic activity, and is also particularly excellent in the ability to decompose volatile organic compounds (VOCs) can be formed by using tungsten(VI) oxide ($WO_3$) as the photocatalyst, and cerium(IV) oxide ($CeO_2$) as the co-catalyst.

In another preferred embodiment, the photocatalyst contains titanium(IV) oxide ($TiO_2$) or tin(IV) oxide ($SnO_2$), and the co-catalyst contains copper(I) oxide ($Cu_2O$) and/or copper(II) oxide (CuO). In this case, the co-catalyst containing copper(I) oxide ($Cu_2O$) and/or copper(II) oxide (CuO) is preferably supported on the photocatalyst containing titanium(IV) oxide ($TiO_2$) or tin(IV) oxide ($SnO_2$). A photocatalyst layer that is excellent in visible-light responsiveness and photocatalytic activity, and is also particularly excellent in anti-microbial properties can be formed by using titanium (IV) oxide ($TiO_2$) or tin(IV) oxide ($SnO_2$) as the photocatalyst, and copper(I) oxide ($Cu_2O$) and/or copper(II) oxide (CuO) as the co-catalyst. In this specification, a co-catalyst-supporting type photocatalyst supporting a co-catalyst $Cu_xO$ on a photocatalyst $TiO_2$ may be represented by $Cu_xO$—$TiO_2$. Similarly, a co-catalyst-supporting type photocatalyst supporting a co-catalyst $Cu_xO$ on a photocatalyst $SnO_2$ may be represented by $Cu_xO$—$SnO_2$. Here, "$Cu_xO$" is intended to mean a state where two types of copper oxides, CuO (X=1; copper(II) oxide) and $Cu_2O$ (X=2; copper(I) oxide) are present.

When the photocatalytic composition is provided as a photocatalyst layer, the thickness of the photocatalyst layer is not particularly limited. As is apparent, air permeability may suffer when the photocatalyst layer is too thick. On the other hand, the photocatalyst layer may fail to show sufficient photocatalytic activity when it is too thin. Considering these, the thickness of the photocatalyst layer is preferably 0.1 μm to 20 μm.

The visible light transmittance of the photocatalyst layer is preferably 70% or more, more preferably 80% or more, particularly preferably 90% or more. The transmittance of the photocatalyst layer for light having a wavelength of 589 nm is preferably 80% or more, more preferably 90% or more. Herein, the visible light transmittance value is a measured value according to JIS R 3106.

FIG. 1 is a schematic representation of the structure of some embodiments of elements described herein. A transparent photocatalytic composition 100 is formed of a photocatalyst material 102 and a co-catalyst 104. Light waves 106 are emitted from a source 108 external to transparent photocatalytic composition 100 in a direction through it. In some embodiments, a photocatalytic element is provided, the element comprising the aforementioned transparent photocatalytic composition 100. In some embodiments, the photocatalytic composition can be a layer. In some embodiments, the photocatalytic composition can be a coating disposed over a substrate.

In some embodiments, the source 108 may include at least one of photoluminescent (phosphorescent or fluorescent), incandescent, electro- or chemo- or sono- or mechano- or thermo-luminescent materials. Phosphorescent materials may include ZnS and aluminum silicate whereas fluorescent materials may include phosphors like YAG-Ce, $Y_2O_3$—Eu, various organic dyes etc. Incandescent materials may include carbon, tungsten while electroluminescent materials may include ZnS, InP, GaN, etc. It will be evident to one of ordinary skill in the art that any other kind of light generation mechanism would suffice for providing the energy to initiate photocatalysis e.g. sunlight, fluorescent lamp, Incandescent lamp, light-emitting diode (LED) based lighting, sodium vapor lamp, halogen lamp, mercury vapor lamp, noble gas discharges, and flames.

Figure 2:
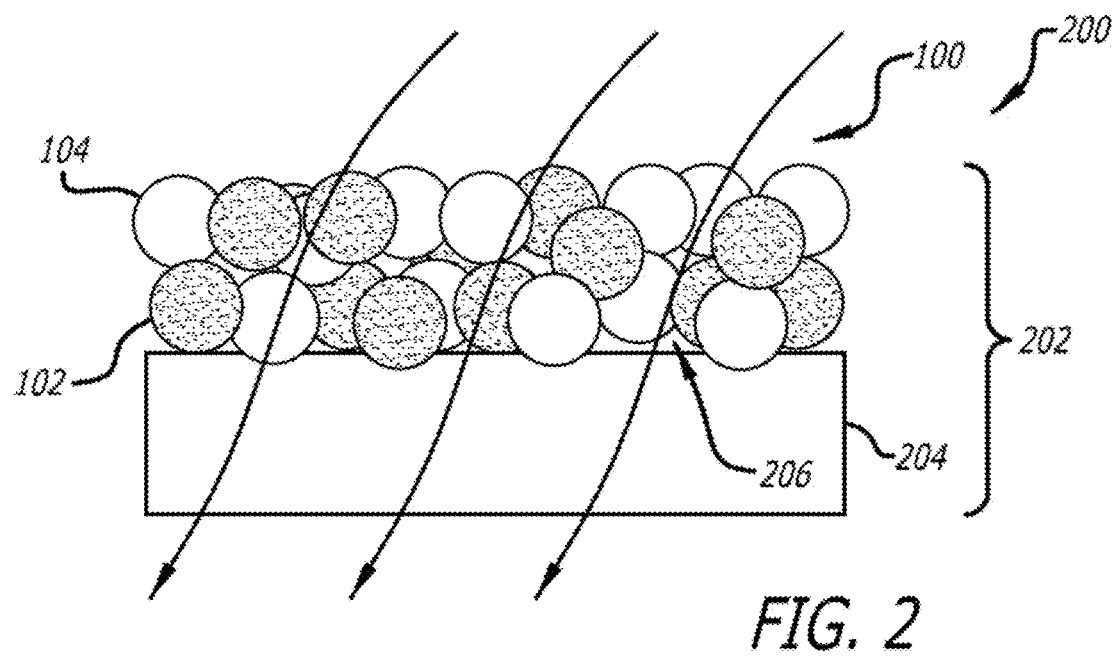
FIG. 2 is a schematic depiction of an embodiment of a photocatalytic coated surface.

FIG. 2 is a schematic representation of a system 200 of some embodiments of the elements described herein. In some embodiments, a transparent photocatalytic element 202 is provided including a substrate 204 and transparent photocatalytic composition 100, the composition including at least one photocatalyst material 102 and a co-catalyst 104 contacting, at least in part, substrate 204. In some embodiments, transparent photocatalytic composition 100 can be applied to or disposed upon substrate 204, at least a portion of transparent photocatalytic composition 100 contacting surface 206 of substrate 204 or a portion thereof. In some embodiments, photocatalyst material 102 and a co-catalyst 104 can have refractive indices within about 0.75, about 0.50, about 0.20, or about 0.05 of each other. For example, in one embodiment, where the at least one photocatalyst material 102 can be $WO_3$ and co-catalyst 104 can be $CeO_2$, the respective refractive indices are 2.20 and 2.36.

Figure 3A:
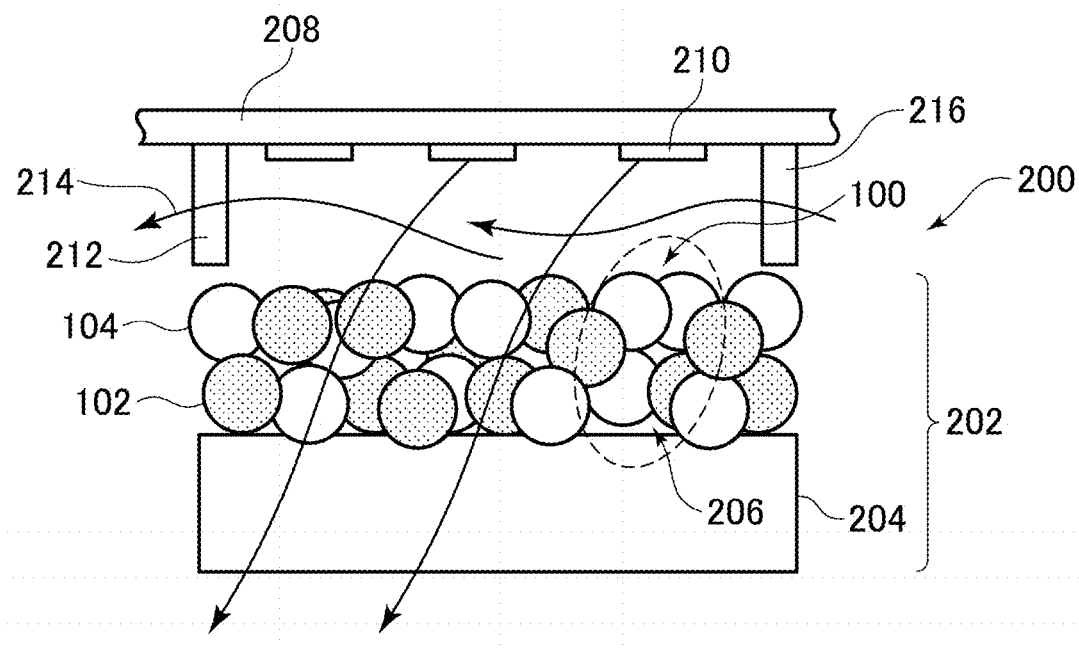
FIG. 3A is a schematic representation of a system comprising a photocatalytic coating described herein.

FIG. 3A is a schematic representation of a system 200 of some embodiments of the elements described herein. In some embodiments, a transparent photocatalytic element 202 is provided including a substrate 204 and transparent photocatalytic composition 100, the composition including at least one photocatalyst material 102 and a co-catalyst 104 contacting, at least in part, substrate 204. In some embodiments, transparent photocatalytic composition 100 can be applied to or disposed upon substrate 204, at least a portion of transparent photocatalytic composition 100 contacting surface 206 of substrate 204 or a portion thereof. In some embodiments, the system further comprises an enclosing element 208, wherein the substrate is disposed within the enclosing element. In some embodiments, the system further comprises a source of electromagnetic radiation 210 that is in optical communication with said photocatalytic composition 100. In some embodiments, the enclosing element 208 can comprise of substantially transparent material which enables the appropriate electromagnetic radiation, e.g., visible light generated by independent sources like sunlight, to interact with the photocatalytic composition. In some embodiments, the system further comprises an airflow element 212 for creating an airflow arrow 214, said airflow element being disposed within said enclosing element, or fixedly attached thereto. In some embodiments, the airflow element is positioned before the photocatalytic composition. In some embodiments, the system can further comprise at least one additional filter element 216. In some embodiments, the at least one additional filter element can be a prefilter, a HEPA/ULPA, a substrate sans the photocatalytic composition and/or an activated carbon filter, and/or combinations of the aforedescribed filter elements.

In some embodiments, the photocatalytic composition is coated to a substrate in such a way that the photocatalyst composition can come into contact with light and material to be decomposed, such as ethylene gas, a malodorous gas, or a microbe.

By being disposed upon the substrate, the photocatalytic composition can be a separately formed layer, formed prior to disposition upon the substrate. In another embodiment, the photocatalytic composition 100 can be formed upon the substrate surface, e.g., by vapor deposition like either chemical vapor deposition (CVD) or physical vapor deposition (PVD); laminating, pressing, rolling, soaking, melting, gluing, sol-gel deposition, spin coating; dip coating; bar coating; slot coating; brush coating; sputtering; thermal spraying including flame spray, plasma spray (DC or RF); high velocity oxy-fuel spray (HVOF) atomic layer deposition (ALD); cold spraying or aerosol deposition.

Figure 22:
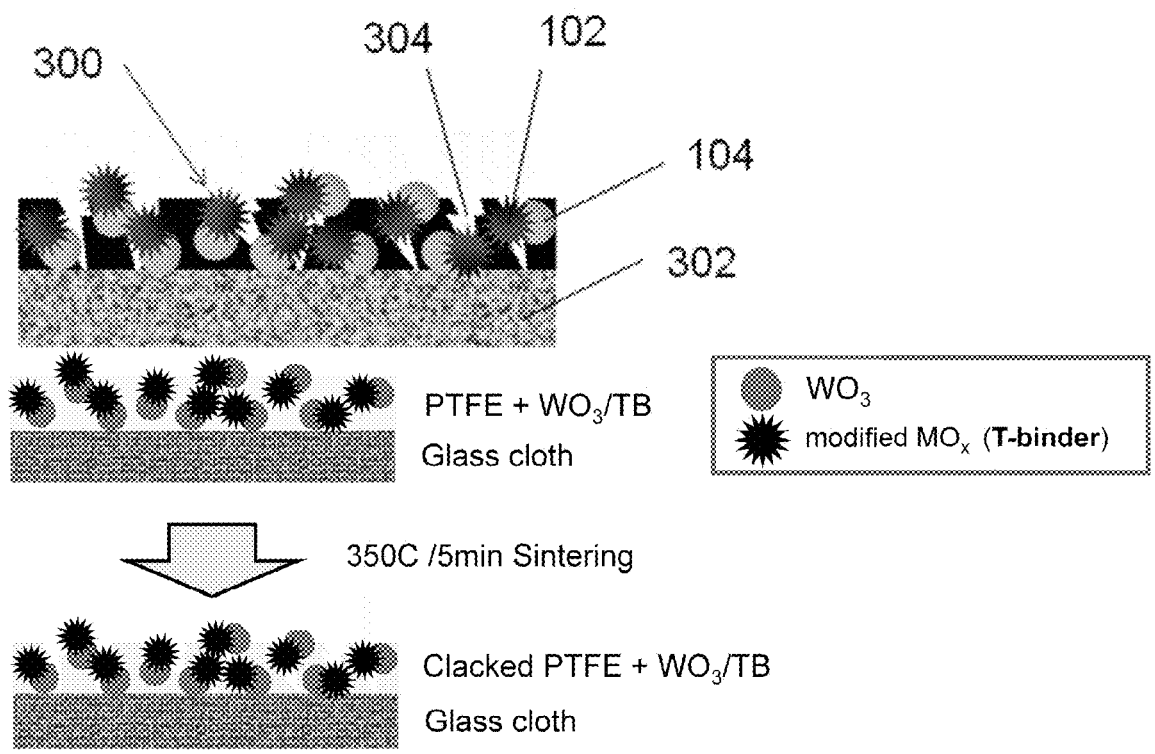
FIG. 22 is a schematic of an embodiment on a glass cloth substrate.

As shown in FIG. 22, in another embodiment, the photocatalytic composition 300 can be incorporated into the surface of the substrate 302, e.g., at least partially embedded within the surface. In some embodiments, as shown in FIG. 22, the substrate 302 can define a plurality of cracks 304 in the contact surface 306 of the substrate. In some embodiments, the substrate can be treated or made to increase the surface area of the substrate. In some embodiments, the substrate material can be heated at a sufficient temperature and sufficient period of time to define a plurality of cracks in the contact surface. In some embodiments, where the substrate is PTFE, the photocatalytic composition 30 or photocatalytic element can be sintered at about 350° C. for about 5 minutes to define a plurality of cracks in the surface, increasing the contact surface area and contact of the photocatalytic composition with the VOC to be removed or decomposed.

In some embodiments, the photocatalyst composition substantially covers the substrate 204. In some embodiment, the photocatalyst composition contacts or covers at least about 75%, at least about 85%, or at least about 95% of the substrate surface 206.

A larger surface area may translate into higher photocatalytic activity. In one embodiment, the Brunner Emmett Teller (BET) specific surface area of the photocatalyst is between 0.1-500 $m^2/g$. In another embodiment, the BET specific surface area of the photocatalyst is between 10-50 $m^2/g$. In some embodiments, the surface area of the substrate is increased at least 10%, at least 20%, at least 30% at least 40%. An exemplary method to determine the increase in surface area can be by Brunauer-Emmett-Teller (BET) methodology.

In another embodiment, a photocatalytic layer is provided including the aforementioned compositions of tungsten oxide to rare earth oxide.

In another embodiment, there is a method for making a photocatalytic composition including creating a dispersion comprising a photocatalyst, $CeO_2$, and a dispersing media, wherein the respective photocatalyst and $CeO_2$ refractive indices are within about 0.75 of each other, the molar ratio of the photocatalyst to $CeO_2$ being between 1-99 molar % photocatalyst and 99-1 molar % $CeO_2$; wherein the dispersion has about 2-50 wt % solid materials; applying the dispersion to a substrate; and heating the dispersion and the substrate at a sufficient temperature and length of time to evaporate substantially all the dispersing media from the dispersion. In some embodiments, the dispersion is applied to cover the substrate, either in whole or in part, or to a surface of the substrate to create a coating or surface layer.

In another embodiment, there is a method for making a photocatalytic composition including mixing an aqueous dispersion of a visible light photocatalyst and $CeO_2$, the ratio of the photocatalyst to $CeO_2$ being between 40-60 molar % photocatalyst and 60-40 molar % $CeO_2$; adding sufficient dispersing media, e.g. water, to attain a dispersion of about 10-30 wt % solid materials; applying the dispersion to a substrate; and heating the substrate at a sufficient temperature and length of time to evaporate substantially all the water from the dispersion and the substrate. In some embodiments the $CeO_2$ can be a sol. In some embodiments, the photocatalyst material is added to the $CeO_2$ sol. In some embodiments, the $CeO_2$ is added to a photocatalyst dispersion. In some embodiments, both the photocatalyst dispersion and $CeO_2$ sol or dispersion are prepared separately and then mixed together to create the dispersion.

In another embodiment, the ratio of the photocatalyst to $CeO_2$ may be about 2:3 to about 3:2, such as between 40-60 molar % photocatalyst and 60-40 molar % $CeO_2$. In another embodiment, the ratio of photocatalyst to $CeO_2$ is about 1:1 [50 molar % to 50 molar %]. In some embodiments, the $CeO_2$ is a sol.

In another embodiment, the amount of dispersing media, e.g. water, added is sufficient to attain a dispersion of about 2-50 wt/o, about 10-30 wt %, about 15-25 wt % solid materials. In another embodiment, the amount of dispersing media, e.g., water, added is sufficient to attain a dispersion of about 20 wt % solid materials In another embodiment, the mixture covered substrate is heated at a sufficient temperature and/or sufficient length of time to substantially remove the dispersing media. In some embodiments at least 90%, at least 95%, at least 99% of the dispersing media is removed.

In another embodiment, the dispersion covered substrate is heated at a temperature between about room temperature and 500° C. In another embodiment, the dispersion covered substrate is heated to a temperature between about 90° C. and about 150° C. In another embodiment, the dispersion covered substrate is heated to a temperature of about 120° C. While not wanting to be limited by theory, it is believed that keeping the temperature below 500° C. may reduce the possibility of thermal deactivation of the photocatalytic material, for example due to photocatalytic material phase change to a less active phase (highly-active anatase $TiO_2$ to less active rutile), dopant diffusion, dopant inactivation, loaded material decomposition or coagulation (reduction in total active surface area).

In another embodiment, the dispersion covered substrate is heated for a time between about 10 seconds and about 2 hours. In another embodiment, the mixture covered substrate is heated for a time of about 1 hour.

The photocatalytic composition may be effective in a range of temperatures. In some embodiments, the photocatalytic composition yields the best results in the temperature range between about 0° C. and about 200° C. In some embodiments, the photocatalytic composition yields the best results in the temperature range between about 10° C. and about 190° C. In some embodiments, the photocatalytic composition yields the best results in the temperature range between about 20° C. and about 180° C. In some embodiments, the photocatalytic composition yields the best results in the temperature range between about 30° C. and about 160° C. In some embodiments, the photocatalytic composition yields the best results in the temperature range between about 40° C. and about 150° C. In some embodiments, the photocatalytic composition yields the best results in the temperature range between about 50° C. and about 140° C. In some embodiments, the photocatalytic composition yields the best results in the temperature range between about 60° C. and about 130° C. In some embodiments, the photocatalytic composition yields the best results in the temperature range between about 70° C. and about 120° C. In some embodiments, the photocatalytic composition yields the best results in the temperature range between about 80° C. and about 110° C. In some embodiments, the photocatalytic composition yields the best results in the temperature range between about 90° C. and about 100° C. In some embodiments, the photocatalytic composition yields the best results in the temperature range between about 25° C. and about 150° C.

The dispersions described herein can be applied to virtually any substrate. Other methods of applying the dispersion to a substrate can include slot/dip/spin coating, brushing, rolling, soaking, melting, gluing, or spraying the dispersion on a substrate. A proper propellant can be used to spray a dispersion onto a substrate.

In some embodiments, the substrate is gas impermeable. In some embodiments the substrate is gas permeable. In some embodiments the substrate has porosity sufficient to allow a gaseous carrier, e.g., air, to flow through the substrate. The term "permeable" refers to a substrate through which gas can diffuse and/or pass through. In some embodiments, the substrate is permeable by any of the gaseous elements of atmospheric air, e.g., oxygen, nitrogen, carbon dioxide, etc. In some embodiments, the substrate is permeable by VOCs. In some embodiments, the substrate is permeable by ethylene. In some embodiments, the substrate is permeable by microbes. In some embodiments the substrate is permeable by some or all of the constituent gaseous elements of the air. In some embodiments, the substrate is gas impermeable, but the system comprising the substrate is gas permeable, e.g., glass wool, porous ceramic, etc.

As shown in FIG. 22, in some embodiments, the substrate can define a plurality of cracks in the contact surface of the substrate. In some embodiments, the substrate can be treated or made to increase the surface area of the substrate. In some embodiments, the substrate material can be heated at a sufficient temperature and sufficient period of time to define a plurality of cracks in the contact surface.

In some embodiments, the substrate need not be capable of transmitting light. For example, the substrate may be a common industrial or household surface on which a dispersion can be directly applied. Substrates can include, glass (e.g., windows, mirrors), walls (e.g., drywall), floors, joinery, stone (e.g., granite counter tops, flooring), masonry (e.g., brick walls), metals (e.g. stainless steel, metal alloys [handles, handrails, faucets]), natural fibers (e.g., cellulose, cotton), woods (e.g., furniture, fencing, shutters), resin materials (plastics) such as polypropylenes (PP), polyethylenes (e.g., polyethylene [PE], polyethylene terephthalates (PET), polytetrafluoroethylenes (PTFE), polyvinylidene fluorides, polyimides and polyamide-imides, perfluoroalkoxy polymer resins, fluorinated ethylene propylene (FEP), ethylene tetrafluoroethylene (ETFE)(e.g. plastic wrap for flowers, plastic handles, plastic keyboards elements), other polymeric surfaces, ceramics (e.g., porcelains [bathtubs, ceramic tiles, sinks, shower stalls, toilets]), other organic substrates (e.g., activated carbon), and the like.

Exemplary items having such substrate surfaces include, but are not limited to, textiles, filters, refrigerators, air conditioners (including the ducting), vacuum cleaners, dishwashers, lighting, humidifiers, dehumidifiers, mobile phones, plasma displays, liquid crystal displays, touch panels, touch screens, fluid storage containers, fuel tanks, motor vehicle interior surfaces, Dispersions in such embodiments can be formulated as paints, liquid adhesives, on tape, on wallpapers, on drapes, on lamp shades, on light covers, on table, floor or counter surface coverings, and the like.

Figure 21:
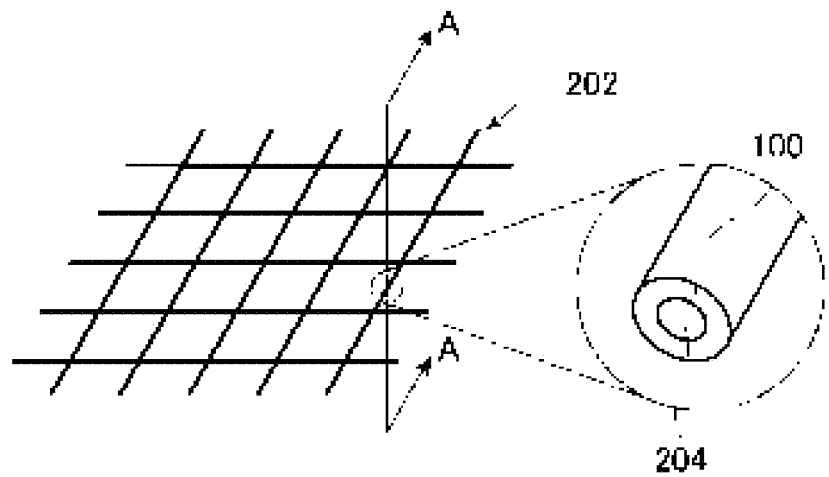
FIG. 21 is a schematic of a photocatalytic woven textile embodiment.
Figure 24:
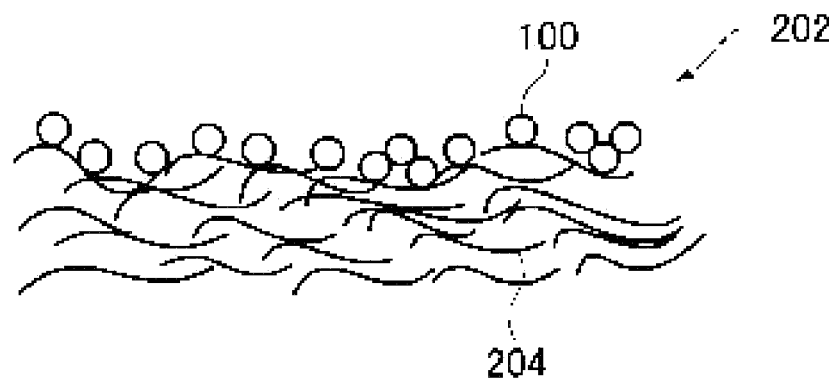
FIG. 24 is a schematic of a photocatalytic non woven textile embodiment.
Figure 25A:
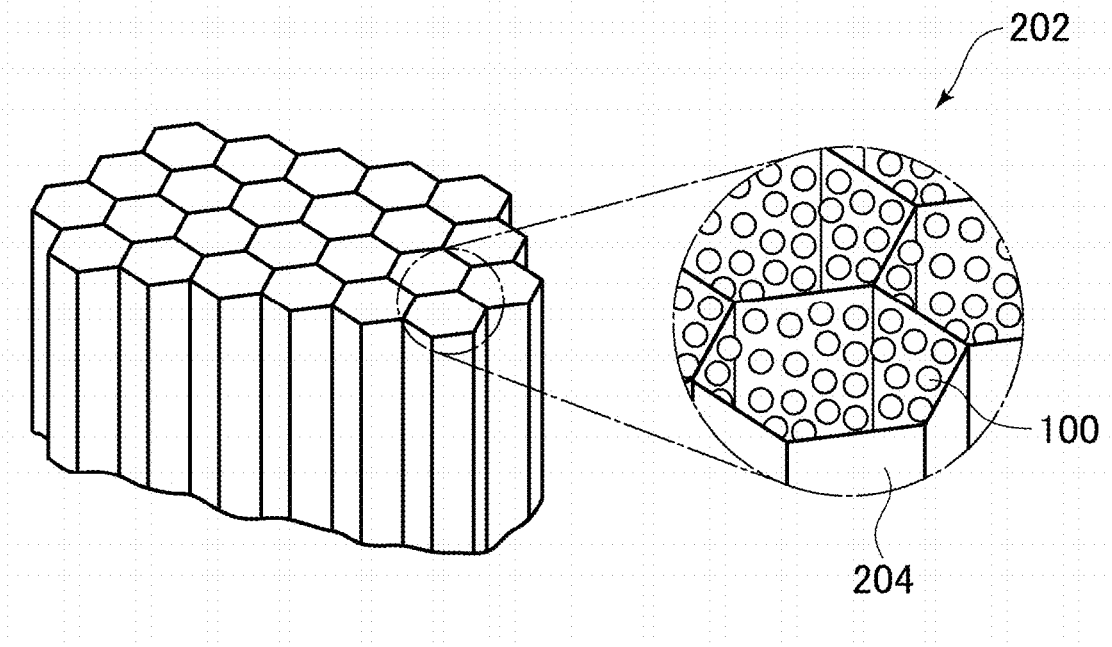
FIG. 25A is a perspective view of a photocatalytic honeycombed filter embodiment.
Figure 25B:
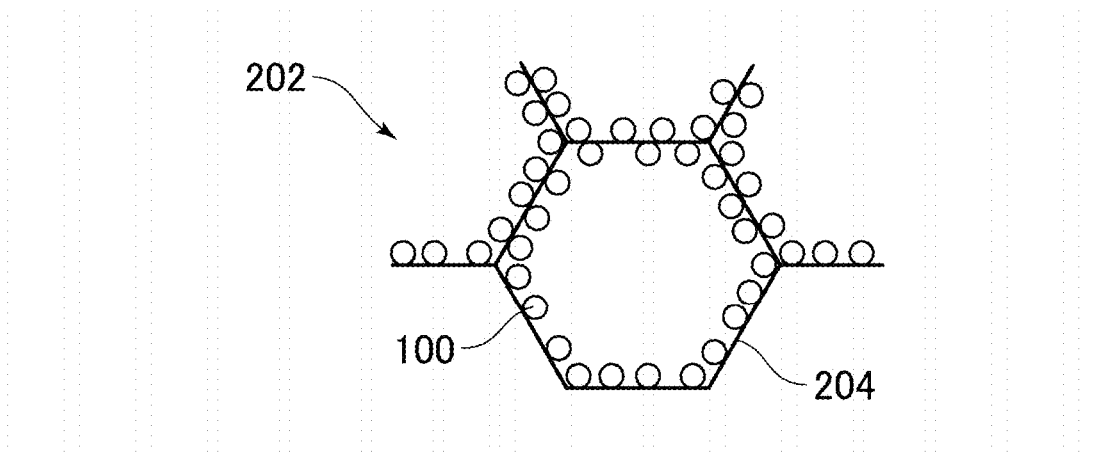
FIG. 25B is a plane view of a photocatalytic honeycombed filter embodiment.
Figure 26:
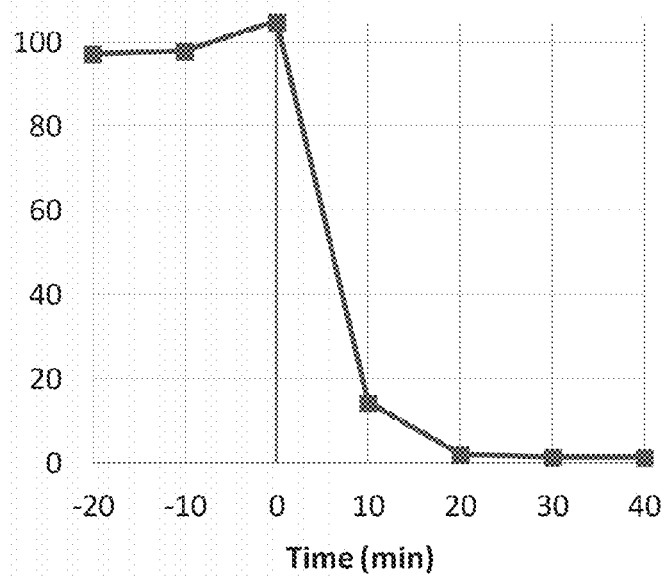
FIG. 26 is a graph of acetaldehyde degradation by a system embodiment of Example 52.

In some embodiments, the substrate can be porous PTFE (High-efficiency particulate absorption [HEPA]/ULPA Filter), other HEPA (e.g., those removing 99.97% of particles that have a size of 0.3 microns or larger) or HEPA like filters, non-woven (see FIG. 24) or woven textile (see FIG. 21), a folding filter (Textile, paper, porous plastic as such as Porous PTFE), Glass/quartz wool, fiber (cellulose, glass quartz, plastics, resins), honeycomb structured (see FIGS. 25A and 25B) cellulose, polymer, metal or ceramic, activated or porous carbon, zeolites (microporous aluminosilicates), or any existing filter materials. Incidentally, in the embodiment as depicted in FIGS. 25A and 25B, the honeycomb structured cellulose possesses hollow portions, and the particles of the photocatalytic composition 100 are adhered (loaded) on the surface of the inner wall of the honeycomb structured cellulose. In some embodiments, the substrate can have a minimum efficiency reporting value of 1-4 (American Society of Heating, Refrigeration & Air conditioning Engineers [ASHREAC]). In some embodiments, the substrate and the photocatalytic composition, e.g. a photocatalyst and a co-catalyst, can be in a vacuum cleaner. For example, the substrate could be vacuum cleaner filter, and could have the photocatalyst and co-catalyst coated on the filter. The vacuum cleaner can further comprise a light source, such as a UV light source, that can be used to expose the photocatalytic composition to the light.

In some embodiments, the substrate comprises ceramic. The ceramic substrate can comprise $Al_2O_3$, $ZrO_2$, $SiO_2$, Mullite ($3Al_2O_3 \cdot 2SiO_2$), Cordierite (($Mg,Fe)_2Al_4Si_5O_{18}$), or other known ceramic materials. In some embodiments the ceramic element comprises $Al_2O_3$. In some embodiments the ceramic element comprises $ZrO_2$. In some embodiments the ceramic element comprises $SiO_2$. In some embodiments the ceramic element comprises Mullite ($3Al_2O_3 \cdot 2SiO_2$). In some embodiments the ceramic element comprises Cordierite. In some embodiments, the ceramic comprises other ceramic materials known in the art.

In some embodiments, the substrate comprises porous ceramic. In some embodiments, the porous ceramic may have interconnected pores. This may ensure that the photocatalytic composition can cover the whole surface of the porous ceramic and air can flow through the photocatalytic-coated ceramic. In addition, the form of porous ceramics is not restricted to those prepared by porous template. Any other porous ceramic such as honeycomb etc. can also be used as a substrate.

In some embodiments, the ceramic substrate can have porosity in the range of about 1 pores per inch (ppi) to about 100 ppi. In some embodiments, the element has a porosity of about 1 ppi to about 100 ppi. In some embodiments, the element has a porosity of about 5 ppi to about 95 ppi. In some embodiments, the element has a porosity of about 10 ppi to about 90 ppi. In some embodiments, the element has a porosity of about 15 ppi to about 85 ppi. In some embodiments, the element has a porosity of about 20 ppi to about 80 ppi. In some embodiments, the element has a porosity of about 25 ppi to about 75 ppi. In some embodiments, the element has a porosity of about 30 ppi to about 70 ppi. In some embodiments, the element has a porosity of about 35 ppi to about 65 ppi. In some embodiments, the element has a porosity of about 40 ppi to about 60 ppi. In some embodiments, the element has a porosity of about 45 ppi to about 55 ppi. In some embodiments, the element has a porosity of about 50 ppi. In some embodiments the element has a porosity comprising any combination of the aforementioned ranges.

In some embodiments, the ceramic substrate can range in thickness from about 1 mm to about 50 mm. In some embodiments, the element is about 1 mm thick to about 5 mm thick. In some embodiments, the element is about 5 mm thick to about 10 mm thick. In some embodiments, the element is about 10 mm thick to about 15 mm thick. In some embodiments, the element is about 15 mm thick to about 20 mm thick. In some embodiments, the element is about 20 mm thick to about 25 mm thick. In some embodiments, the element is about 25 mm thick to about 30 mm thick. In some embodiments, the element is about 30 mm thick to about 35 mm thick. In some embodiments, the element is about 35 mm thick to about 40 mm thick. In some embodiments, the element is about 40 mm thick to about 45 mm thick. In some embodiments, the element is about 45 mm thick to about 50 mm thick.

In some embodiments, a commercially available porous ceramics may be used as the substrate. In some embodiments, the photocatalytic composition is loaded onto a porous ceramic substrate by dip coating.

In some embodiments, the photocatalytic composition may be formed into a suspension for loading onto a ceramic substrate. In some embodiments, the suspension can comprise a binder, an organic solvent and a photocatalytic material. In some embodiments, the binder can be a silicon polymer. Suitable, coatings and methods for performing the same are described in U.S. Provisional Application 61/899,423, filed Nov. 4, 2013, which Is incorporated by reference in its entirety. In some embodiments, tungsten trioxide powder may be mixed with colloidal $CeO_2$ and diluted with ultra-pure water to proper viscosity for loading on porous ceramics by impregnation. Commercially available tungsten trioxide powder with a median particle size below 1 micrometer may be used. Colloidal $CeO_2$ is available from commercial products which contain solid $CeO_2$ of about 20 wt %. Ultra-pure water for dilution has an electrical resistivity of 18.2 MΩ·cm, such as MilliQ water. The formulation of photocatalytic composition suspension may be adjusted so that the molar ratio of $WO_3$ to $CeO_2$ is about one to one (50 molar % to 50 molar %), and total solid content in the suspension was of 20 wt %. A homogeneous loading suspension may be obtained by dispensed the constituents in glass vial in sonication bath and then mixing with sonication horn probe.

Loading of photocatalytic composition on porous ceramics may be carried out by impregnating the porous ceramics carrier with the photocatalytic composition suspension. A thin layer of photocatalytic composition may be formed on the surface of pores in the ceramic by different ways, for example, by dip coating or spinning the suspension-impregnated porous ceramics to avoid formation of blocked pores by the suspension. The coated porous ceramics may be dried at 120° C. for 1 hr and then annealed at 400° C. in ambient atmosphere for 1 hr to increase the adhesion of the photocatalytic composition to the substrate.

In some embodiments, loading of the photocatalytic composition suspension can be done by applying the suspension with a pipette onto the porous ceramic and then spinning the loaded ceramic in a spin coater to remove extra suspension and achieve a uniform coating thickness of the photocatalytic composition.

In some embodiments, the substrate comprises a thin film, like those used for wrapping flower arrangements. The film may be, but need not be, gas (ethylene) permeable. Additionally, the film may be, but need not be, transparent. The film may be made of low density polyethylene (LDPE), high density polyethylene (HDPE), polypropylene (PP), polyvinyl chloride (PVC), polyethylene terephthalate (PET), polyethylene terephthalate glycol-modified (PETG), Nylon 6, ionomer, nitrile rubber modified acrylonitrile-methyl acrylate copolymer, or cellulose acetate. In some embodiments, the photocatalytic composition may be disposed on the thin film substrate, e.g., by vapor deposition like physical vapor deposition (PVD); laminating, pressing, rolling, soaking, gluing, sol-gel deposition, spin coating; dip coating; bar coating; slot coating; brush coating; sputtering; atomic layer deposition (ALD); cold spraying or aerosol deposition. In some embodiments, the photocatalytic composition can be incorporated into the surface of the substrate, e.g., at least partially embedded within the surface.

In some embodiments the thin film has a thickness between about 10 microns and 250 microns or thicker. In some embodiments the film has a thickness of between about 10 microns and about 30 microns. In some embodiments the film has a thickness of between about 30 microns and about 50 microns. In some embodiments the film has a thickness of between about 50 microns and about 70 microns. In some embodiments the film has a thickness of between about 70 microns and about 90 microns. In some embodiments the film has a thickness of between about 90 microns and about 110 microns. In some embodiments the film has a thickness of between about 110 microns and about 130 microns. In some embodiments the film has a thickness of between about 130 microns and about 150 microns. In some embodiments the film has a thickness of between about 150 microns and about 170 microns. In some embodiments the film has a thickness of between about 170 microns and about 190 microns. In some embodiments the film has a thickness of between about 190 microns and about 210 microns. In some embodiments the film has a thickness of between about 210 microns and about 230 microns. In some embodiments the film has a thickness of between about 230 microns and about 250 microns.

In some embodiments, the substrate comprises glass. The substrate may be a silicate or polycarbonate glass, or other glass typically used for glass fibers, windows and/or displays, for example, the sides and door of a reach-in case for a retail flower display. In some embodiments, the glass substrate comprises a vase for storing or displaying flowers. In some embodiments, the glass substrate comprises a plurality of glass fibers. In some embodiments, the glass substrate comprises a plurality of non-woven glass fibers. In some embodiments, the glass substrate comprises a glass felt material, e.g., "E-glass" glass felt (Fibre Glast Developments Corp., Brookville, Ohio, USA). The glass substrate may comprise other glass known in the art. The photocatalytic composition may be formed upon the glass substrate, e.g., by vapor deposition like either chemical vapor deposition (CVD) or physical vapor deposition (PVD); laminating, pressing, rolling, soaking, melting, gluing, sol-gel deposition, spin coating; dip coating; bar coating; slot coating; brush coating; sputtering; thermal spraying including flame spray, plasma spray (DC or RF); high velocity oxy-fuel spray (HVOF) atomic layer deposition (ALD); cold spraying or aerosol deposition. In another embodiment, the photocatalytic composition can be incorporated into the surface of the substrate, e.g., at least partially embedded within the surface.

In some embodiments, the system may further comprise at least one additional filter element, the additional filter element being without a photocatalytic compound. In some embodiments, the system may further comprise at least one additional filtering element. In some embodiments, the additional filtering element is a size excluding element. In some embodiments, the additional filtering element can exclude materials between 20 nm and 5 mm, between 50 nm and 10 microns, particles less than 2.5 microns in diameter. In some embodiments, the additional filtering element can be an ionic element, wherein the filtering can exclude or reduce the amount of ionically charged material passing therethrough.

In some embodiments the at least one additional filtering element can comprise a pre-filter element. In some embodiments, the at least one additional filtering element can comprise a HEPA/ULPA filter. In some embodiments, the at least one additional filtering element can comprise activated carbon. In some embodiments, the at least one additional filtering element can comprise a combination of any or all of the prefilter element, the HEPA/ULPA filter, the activated carbon filter and/or any other filtering material or substrate. In some embodiments, the additional filters can be in the order of prefilter, hepa filter, activated carbon filter and then photocatalytic filter.

In some embodiments, the at least one additional filter can comprise a prefilter element. In some embodiments, the prefilter filter element provides an initial size exclusion filtering function. The size exclusion can be, for example, between 20 nm and 5 mm, between 50 nm and 10 microns, particles less than 2.5 microns in diameter. In some embodiments, the prefilter element can comprise paper, non woven materials (metal strands, glass fibers, cellulose fibers, polymeric filters/foam materials).

In some embodiments the prefilter element is positioned before the photocatalytic filter element, to receive the air flow from the environment prior to the photocatalytic filter element. In some embodiments, the one additional filter element can be a substrate over which the photocatalytic composition is disposed.

In some embodiments, the at least one additional filter element can be a HEPA filter. In some embodiments, the HEPA filter provides additional size exclusion filtering function. The size exclusion can be, as previously described, as those removing 99.97% of particles that have a size of 0.3 microns or larger. In some embodiments, the HEPA filter can comprise PTFE.

In some embodiments, the at least one additional filter can comprise activated carbon. Active carbons (R1) are made in particulate form as powders or fine granules less than 1.0 mm in size with an average diameter between 0.15 and 0.25 mm. In some embodiments, the active carbons can provide a large surface to volume ratio with a small diffusion distance. In some embodiments, powdered activate carbon can be crushed or ground carbon particles, 95-100% of which will pass through a designated mesh sieve. Activated carbon can be an R1 activated carbon. In some embodiments the activated carbon particles can be sized to be retained on a 50-mesh sieve (0.297 mm) and/or smaller. In some embodiments, the activated carbon particle can be retained on an 80-mesh sieve (0.177 mm) and smaller.

In some embodiments, the activated carbon filter comprises granular activated carbon. In some embodiments, the activated carbon can be extruded activated carbon. In some embodiments, granular activated carbon can be sized selected from 8×20, 20×40, or 8×30. In some embodiments, the granular activated carbon can be at least sized 4×6, 4×8 and/or 4×10. A 20×40 carbon is made of particles that will pass through a U.S. Standard Mesh Size No. 20 sieve (0.84 mm) (generally specified as 85% passing) but be retained on a U.S. Standard Mesh Size No. 40 sieve (0.42 mm) (generally specified as 95% retained). AWWA (1992) B604 uses the 50-mesh sieve (0.297 mm) as the minimum GAC size.

In some embodiments, to effectively reduce the concentration of ethylene in air, the photocatalytic composition must contact the ethylene gas while illuminated. An appropriate combination of porosity and thickness may be chosen to optimize the airflow and light exposure in order to achieve and maintain the desired ethylene concentration. In some embodiments an airflow element is provided to generate air movement.

In some embodiments, the airflow element may generate an airflow between 0.01 liters per minute to 1100 liters per minute. In some embodiments, the airflow element may generate an airflow up to about 0.01 liters per minute, about 0.02 liters per minute, about 0.03 liters per minute, about 0.04 liters per minute, about 0.05 liters per minute, about 0.06 liters per minute, about 0.07 liters per minute, about 0.08 liters per minute, about 0.09 liters per minute. In some embodiments, the airflow element may generate an airflow up to about 0.1 liters per minute, about 0.2 liters per minute, about 0.3 liters per minute, about 0.4 liters per minute, about 0.5 liters per minute, about 0.6 liters per minute, about 0.7 liters per minute, about 0.8 liters per minute, about 0.9 liters per minute. In some embodiments, the airflow element may generate an airflow up to about 1.0 liters per minute, about 2.0 liters per minute, about 3.0 liters per minute, about 4.0 liters per minute, about 5.0 liters per minute, about 6.0 liters per minute, about 7.0 liters per minute, about 8.0 liters per minute, about 9.0 liters per minute. In some embodiments, the airflow element may generate an airflow up to about 10 liters per minute, about 20 liters per minute, about 30 liters per minute, about 40 liters per minute, about 50 liters per minute, about 60 liters per minute, about 70 liters per minute, about 80 liters per minute, about 90 liters per minute, about 100 liters per minute. In some embodiments, the airflow element may generate an airflow up to about 200 liters per minute, about 300 liters per minute, about 400 liters per minute, about 500 liters per minute, about 600 liters per minute, about 700 liters per minute, about 800 liters per minute, about 900 liters per minute, about 1000 liters per minute. In some embodiments, the airflow element may generate an airflow in any combination of the aforementioned rates, up to about 1100 liters per minute. In some embodiments, the airflow element may generate an airflow at about 1.0 liter per minute. In some embodiments, the airflow element may generate an airflow at about 378 liter per minute. In some embodiments, the airflow element may generate an airflow at about 915 liter per minute. In some embodiments, the airflow element may generate an airflow at about 1072 liter per minute. In some embodiments, the airflow element may generate an airflow at about 1000 liter per minute. Those skilled in the art will recognize that various airflow elements, including but not limited to fans, systems that generate pressure differentials can be used. In some embodiments, the airflow element may generate an airflow at about 1 cubic foot per minute to about 300 cubic feet per minute (CFM). Those skilled in the art will recognize that 1 liter per minute is about 0.03531466 cubic feet per minute.

In some embodiments, the airflow element can generate an airflow of about 0.1 m/sec to about 10 m/sec through, on or over the material in which the photocatalytic material is disposed. In some embodiments, the airflow element can generate an airflow of about 1 m/sec to about 7 m/sec through, on or over the material in which the photocatalytic material is disposed. In some embodiments, the airflow element can generate an airflow of about 3 m/sec to about 5 m/sec, e.g., about 4 m/sec, through, on or over the material in which the photocatalytic material is disposed.

In some embodiments, the airflow element can comprise a substrate on, over, or in which the photocatalytic composition is disposed.

The photocatalyst material, compositions, and dispersions described herein can be used as a disinfectant, an odor eliminator, a pollutant eliminator, a self-cleaner, an antimicrobial agent and the like. The materials, compositions, and dispersions can be used to interact with air, liquid, microbial and/or solid substances. In one embodiment, they can be used to clean air such as in confined environments such as in aircraft fuselages or in more contaminated environments such as auto garages. In other embodiments, they can be used for antimicrobial properties such as to coat surfaces in need of disinfection such as food service or production facilities or hospitals or clinics. In other embodiments, they can be used to extend the stock life of cut plants, including, but not limited to, fruits, vegetables, and flowers.

A photocatalyst composition may be capable of photocatalytically decomposing an organic compound, such as an aldehyde, including acetaldehyde formaldehyde, propionaldehyde, etc.; a hydrocarbon, such as an alkane, including methane, ethane, propane, butane, etc.; an aromatic hydrocarbon, such as benzene, naphthalene, anthracene, etc.; crude oil, or fraction thereof; dyes such as anthocyanins, methylene blue, basic blue 41; volatile organic compounds, such as methane, ethane, propane, butane, benzene, ethylene, toluene, acetone, diethyl ether, methanol, ethanol, isopropyl alcohol, formaldehyde, ethyl acetate, xylene, etc.; $NO_x$, such as NO, $NO_2$, $N_2O$, HONO; $SO_x$, such as $SO_2$, $SO_3$, etc.; CO, $O_3$; etc., small organic molecules such as caffeine, diclofenac, ibuprofen, geosmin, flumequine, etc., bacteria such as *Escherichia coli, Staphylococcus aureus, Acinetobactor, Pseudomonas aeruginosa* etc., virus such as MS2, influenza, norovirus, etc., bacterial spores such as *Clostridium difficile*, protozoa such as *Giardia*, etc., and fungi such as *Candida*, etc. Photocatalytic decomposition may occur in a solid, liquid, or a gas phase.

In some embodiments, methods are utilized wherein polluted air is exposed to light and a photocatalyst material, composition, or dispersion as described herein thereby removing pollutants from the air.

In some embodiments, light and a photocatalyst material, composition, or dispersion can remove about 50%, about 60%, about 70%, about 80%, about 90%, about 95%, about 99% or more of the pollution, including ethylene gas, from the air.

In other embodiments, methods are utilized wherein biological contaminants are exposed to light and a photocatalyst material, composition, or dispersion as described herein thereby disinfecting the biological material. In some embodiments, biological materials can include food products.

In some embodiments, methods are utilized to remove contaminants from adjacent plants by placing a system as described herein in atmospheric communication with an ethylene-sensitive plant; and reducing the amount of ethylene to a concentration below a threshold by recontacting ethylene with the photocatalytic composition while said photocatalytic composition is illuminated by electromagnetic radiation comprising a wavelength sufficient to activate the photocatalytic composition.

In some embodiments, the method further comprises removing the atmospheric environment proximate to the plant and placing an element comprising at least a photocatalyst and at least a co-catalyst proximate in atmospheric communication with the atmospheric environment. In some embodiments, the method further comprises replacing the cleansed or reduced contaminant concentration atmosphere proximate to the plant.

In some embodiments, light and a photocatalyst material, composition, or dispersion can remove about 50%, about 60%, about 70%, about 80%, about 90%, about 95% or more of the contamination from the biological material from the air.

In some embodiments, the substrate defines a volume. In some embodiments, the volume defined may be a conical volume, e.g., the volume defined by a thin film wrapped around flowers. In some embodiments, the volume may be a rectangular prism, e.g., a box. In some embodiments, the volume may be a cylindrical volume, e.g., a tube. In some embodiments, the volume may be any other volume defined by a substrate. Those skilled in the art will recognize that the substrate may define other volumes, including, but not limited to, spheres, pyramids, tetrahedrons, etc. Additionally, those skilled in the art will recognize that a volume may be defined by a surface that does not fully enclose the volume, e.g., the thin film wrapped around flowers.

In some embodiments, the contaminant decomposition system comprises an enclosing element. In some embodiments, the enclosing element may be a box, e.g., a fan box. In some embodiments, the enclosing element may be a cylinder, e.g., a tube. Those skilled in the art will recognize that the enclosing element may comprise other shapes. Additionally, those skilled in the art will recognize that the enclosing element may be made of many different materials, including, but not limited to, plastic, wood, glass, etc. In some embodiments, the enclosing element can comprise a substrate on, over or in which the photocatalytic composition is disposed. In some embodiments, the enclosing element can comprise an enclosure for a portable air cleaner, portable air purifier, duct, HVAC, vacuum, refrigerator, automobile (including for cabin air, engine air, vacuum system), train, elevator, hospital, museum, greenhouse, theater, art gallery, etc.

In some embodiments, the contaminant decomposition system comprises at least a source of electromagnetic radiation. In some embodiments, the source of electromagnetic radiation emits electromagnetic radiation comprising a wavelength in the visible spectrum, where the visible spectrum is between about 350 nm and about 800 nm. In some embodiments, the source of electromagnetic radiation comprises at least an LED. In some embodiments, the LED is a Blue-LED. In some embodiments, the Blue-LED emits electromagnetic radiation having a wavelength of about 440 nm. In some embodiments, the electromagnetic radiation comprises at least a wavelength sufficient to activate the photocatalytic composition. Those skilled in the art will recognize that to activate the photocatalytic composition, the electromagnetic radiation will comprise energy similar to the energy difference between the valence band and conduction band of the photocatalytic composition. In some embodiments, the source of electromagnetic radiation is in optical communication with the photocatalytic composition. This means that the radiation from the source of electromagnetic radiation illuminates the photocatalytic composition.

Figure 27:
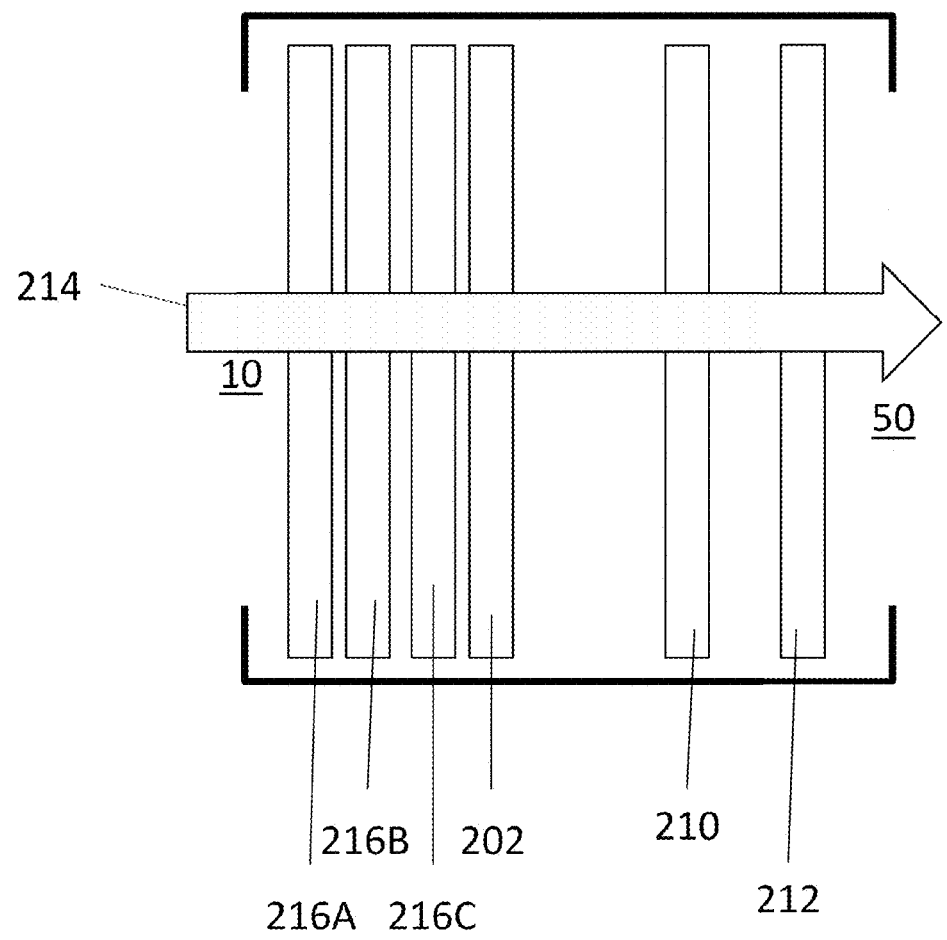
FIG. 27 is a schematic diagram of a system embodiment.

FIG. 27 depicts a contaminant decomposition system 200 comprising an enclosing element (not shown), and, in order in the direction of airflow, a pre-filter 216A, a HEPA/ULPA filter element 216B, an activated carbon filter element 216C, a photocatalytic coated filter element 202, a plurality of Blue-LED electromagnetic radiation sources 210 in optical communication with the photocatalytic coated filter element 202, and an airflow generating element 212, e.g., a fan.

Figure 28:
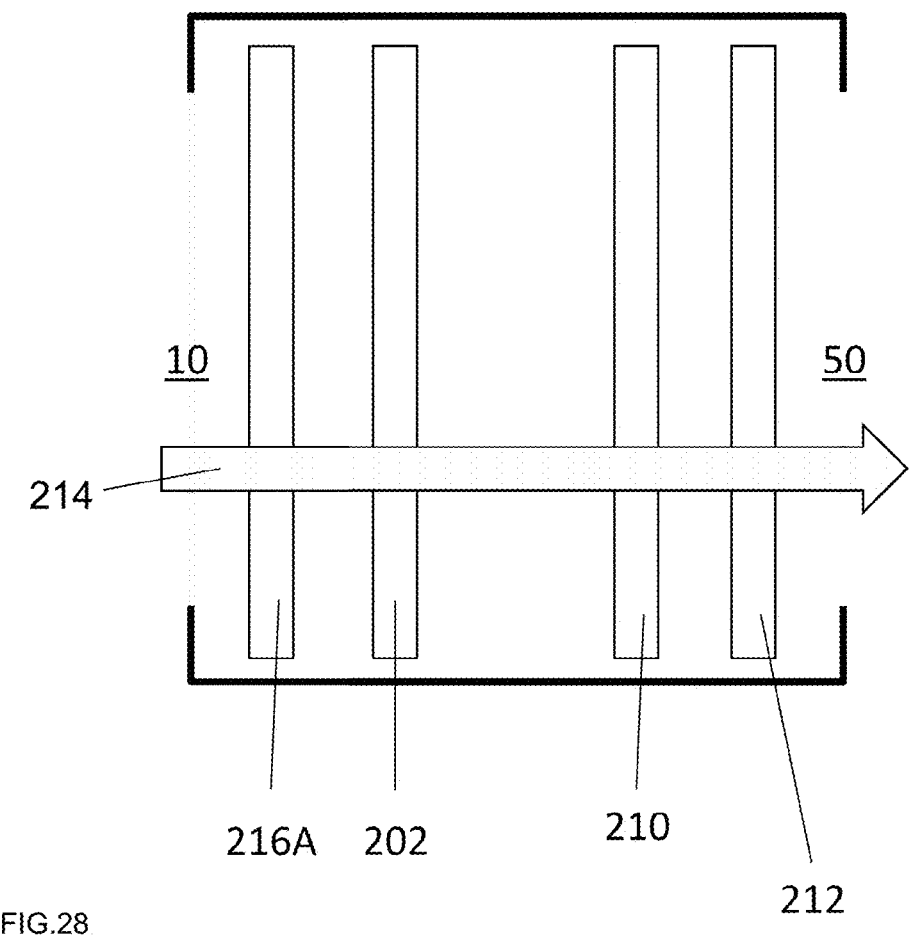
FIG. 28 is a schematic diagram of a system embodiment.

FIG. 28 depicts a contaminant decomposition system 200 comprising an enclosing element (not shown), and, in order in the direction of airflow, a pre-filter 216A, a photocatalytic coated filter element 202, a plurality of BLUE-LED electromagnetic radiation sources 210 in optical communication with the photocatalytic coated filter element 202, and an airflow generating element 212, e.g., a fan.

Figure 29:
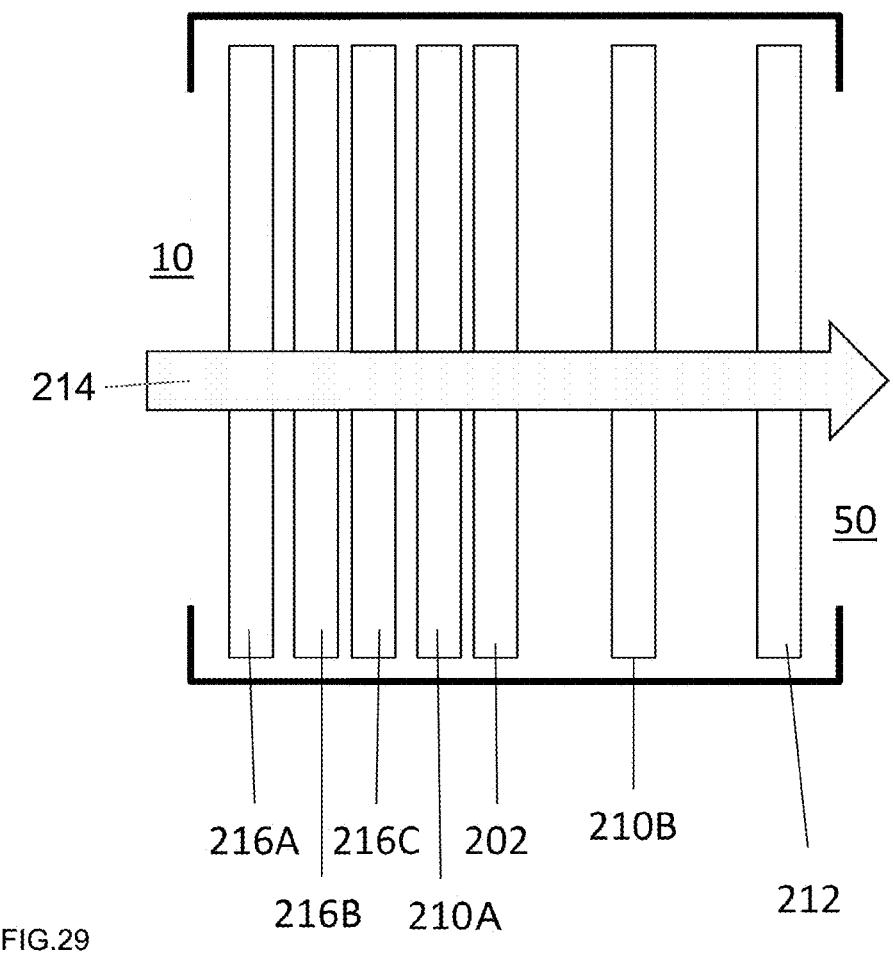
FIG. 29 is a schematic diagram of a system embodiment.

FIG. 29 depicts a contaminant decomposition system 200 comprising an enclosing element (not shown), and, in order in the direction of airflow, a pre-filter 216A, a HEPA/ULPA filter element 216B, an activated carbon filter element 216C, a first plurality of Blue-LED electromagnetic radiation sources 210A in optical communication with a photocatalytic coated filter element 202, the photocatalytic coated filter element 202, a second plurality of Blue-LED electromagnetic radiation sources 210B in optical communication with the photocatalytic coated filter element 202, and an airflow generating element 212, e.g., a fan.

Figure 30:
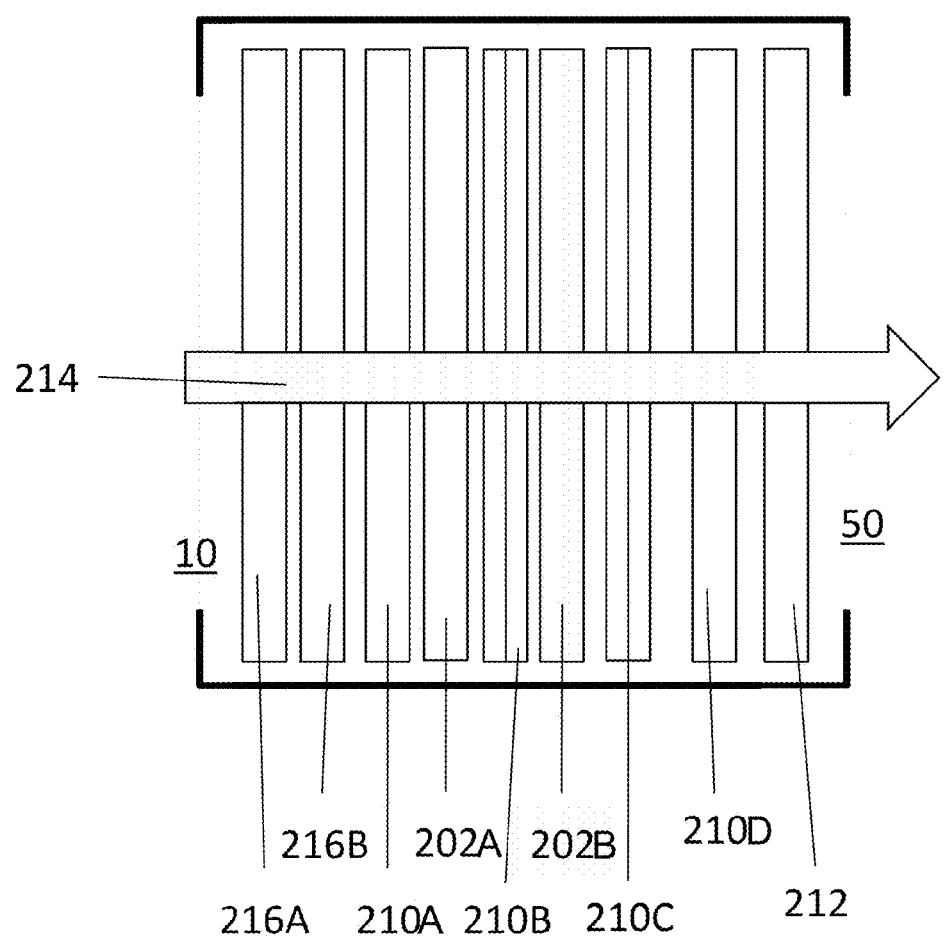
FIG. 30 is a schematic diagram of a system embodiment.

FIG. 30 depicts a contaminant decomposition system comprising an enclosing element (not shown), and, in order in the direction of airflow, a pre-filter 216A, a HEPA/ULPA filter element 216B, a first plurality of Blue-LED electromagnetic radiation sources 210A in optical communication with a first photocatalytic coated filter element 202A, a first photocatalytic coated filter element 202A, a second plurality of Blue-LED electromagnetic radiation sources 210B in optical communication with the first photocatalytic coated filter element 202A, a third plurality of Blue-LED electromagnetic radiation sources 210C in optical communication with a second photocatalytic coated filter element 202B, a second photocatalytic coated filter element 202B, a fourth plurality of Blue-LED electromagnetic radiation sources 210D in optical communication with the second photocatalytic coated filter element 202B, a fifth plurality of Blue-LED electromagnetic radiation sources 210E (not shown) in optical communication with a third photocatalytic coated filter element 202C (not shown), a third photocatalytic coated filter element 202C, and an airflow generating element 216, e.g., a fan.

Figure 31:
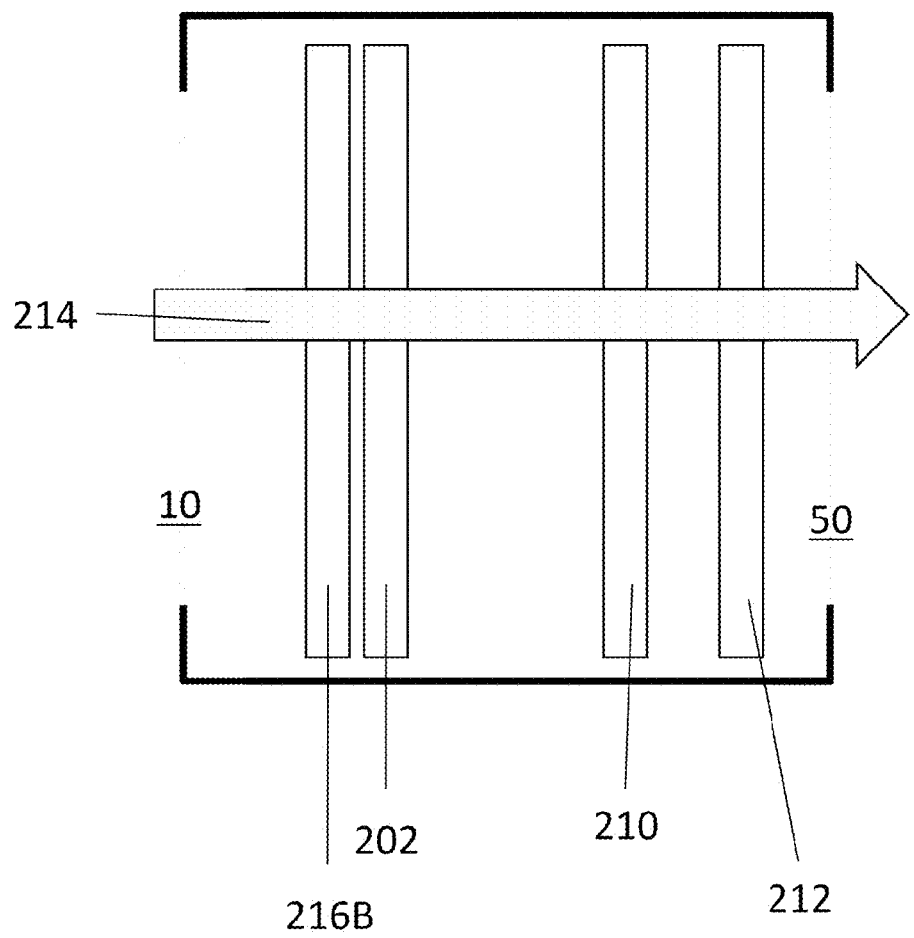
FIG. 31 is a schematic diagram of a system embodiment.

FIG. 31 depicts a contaminant decomposition system comprising an enclosing element (not shown), and, in order in the direction of airflow 214, a pre-filter 216A (not shown), a photocatalytic coated HEPA/ULPA filter element 216B, a plurality of Blue-LED electromagnetic radiation sources 210 in optical communication with a photocatalytic coated HEPA/ULPA filter element 202, and an airflow generating element 212, e.g., a fan.

In some embodiments, the photocatalytic composition is used to reduce the concentration of ethylene gas by placing an element comprising at least a photocatalyst and at least a co-catalyst proximate to a plant. The plant may include, but is not limited to, harvested plants. The plant may be a plant that is sensitive to ethylene gas, or the plant may be one that generates ethylene gas, or the plant may be both ethylene sensitive and generate ethylene gas. The plants may include, but are not limited to, cut flowers, harvested fruit, and harvested vegetables.

The term proximate may refer to a range of distances. In some embodiments, proximate means the photocatalytic element is within about less than one meter to about 100 meters of the plants. In some embodiments, proximate means the photocatalytic element is within about 0.1 meters, about 0.2 meters, about 0.3 meters, about 0.4 meters, about 0.5 meters, about 0.6 meters, about 0.7 meters, about 0.8 meters, about 0.9 meters, or about 1.0 meters of the plants. In some embodiments, proximate means the photocatalytic element is placed within about 1 meter to about 2 meters, about 2 meters to about 3 meters, about 3 meters to about 4 meters, about 4 meters to about 5 meters. In some embodiments, proximate means the photocatalytic element is placed within about 5 meters to about 10 meters, within about 10 meters to about 15 meters, within about 15 meters to about 20 meters, within about 20 meters to about 25 meters, within about 25 meters to about 30 meters, within about 30 meters to about 35 meters, within about 35 meters to about 40 meters, within about 40 meters to about 45 meters, within about 45 meters to about 40 meters, within about 40 meters to about 45 meters, within about 45 meters to about 50 meters, within about 50 meters to about 60 meters, within about 60 meters to about 70 meters, within about 70 meters to about 80 meters, within about 80 meters to about 90 meters, within about 90 meters to about 100 meters. In some embodiments, proximate means the photocatalytic element is placed within distance comprising any combination of the aforementioned ranges, up to 100 meters.

A plant that is ethylene sensitive is one that suffers adverse effects when exposed to ethylene gas. Such adverse effects may include wilting, discoloration including yellowing of leaves, signs of ripening including changes in sugar content and/or softening of fruit, flower buds opening or blooming, senescence.

In some embodiments, the photocatalytic element is located proximate to flowers, including, e.g., carnations, petunias, orchids, roses, etc. The flowers may be on display for decoration or sale, or may be in a storage area, or wrapped in a thin film for transportation, display, or after purchase. In some embodiments, the flowers are ethylene producing flowers. In some embodiments, the flowers are ethylene sensitive flowers. In some embodiments, the flowers are both ethylene sensitive and ethylene producing. The embodiments are used to reduce the concentration of ethylene gas around the flowers by oxidizing the ambient ethylene. The embodiments may be used in a system that reduces the ethylene below in the immediate environment about the flowers a threshold such that the flowers do not show blooming, discoloration, senescence, or other undesirable effects of ethylene exposure, and the embodiments maintain the ethylene below that threshold concentration to preserve the flowers.

In some embodiments, the threshold is about 50 ppm. In some embodiments, the threshold is about 45 ppm. In some embodiments, the threshold is about 40 ppm. In some embodiments, the threshold is about 35 ppm. In some embodiments, the threshold is about 30 ppm. In some embodiments, the threshold is about 25 ppm. In some embodiments, the threshold is about 20 ppm. In some embodiments, the threshold is about 15 ppm. In some embodiments, the threshold is about 10 ppm. In some embodiments, the threshold is about 5 ppm. In some embodiments, the threshold is about 1 ppm. In some embodiments, t the threshold is about 0.1 ppm. In some embodiments, the threshold is about 0.01 ppm. In some embodiments, the threshold is about 0.001 ppm.

In some embodiments, the photocatalytic element is located proximate to climacteric fruit. In some embodiments, the fruit is an ethylene producing fruit. In some embodiments, the fruit is an ethylene sensitive fruit. In some embodiments, the fruit is both ethylene sensitive and ethylene producing. In some embodiments, the climacteric fruit can include, but are not limited to, apple, apricot, banana, fig, melon, nectarine, peach, and tomato. In another embodiment, the ethylene decomposition element is located proximate to harvested fruit. The fruit may be on display for decoration or sale, or may be in the storage area, or wrapped in a thin film for transportation, display, or after purchase. The embodiments are used to reduce the concentration of ethylene gas around the fruit by oxidizing the ambient ethylene. The embodiments may be used in a system that reduces the ethylene below a threshold such that the fruit does not show ripening, discoloration, senescence, or other undesirable effects of ethylene exposure, and the embodiments maintain the ethylene below that threshold concentration to preserve the fruit. In some embodiments, the threshold is about 50 ppm. In some embodiments, the threshold is about 45 ppm. In some embodiments, the threshold is about 40 ppm. In some embodiments, the threshold is about 35 ppm. In some embodiments, the threshold is about 30 ppm. In some embodiments, the threshold is about 25 ppm. In some embodiments, the threshold is about 20 ppm. In some embodiments, the threshold is about 15 ppm. In some embodiments, the threshold is about 10 ppm. In some embodiments, the threshold is about 5 ppm. In some embodiments, the threshold is about 1 ppm. In some embodiments, t the threshold is about 0.1 ppm. In some embodiments, the threshold is about 0.01 ppm. In some embodiments, the threshold is about 0.001 ppm.

In some embodiments, the photocatalytic element is located proximate to vegetables. In some embodiments, the vegetable is an ethylene producing vegetable. In some embodiments, the vegetable is an ethylene sensitive vegetable. In some embodiments, the vegetable is both ethylene sensitive and ethylene producing. The vegetables may be on display for decoration or sale, or may be in the storage area, or wrapped in a thin film for transportation, display, or after purchase. The embodiments are used to reduce the concentration of ethylene gas around the vegetables by oxidizing the ambient ethylene. The embodiments may be used in a system that reduces the ethylene below a threshold such that the vegetables do not show ripening, discoloration, senescence, or other undesirable effects of ethylene exposure, and the embodiments maintain the ethylene below that threshold concentration to preserve the vegetables. In some embodiments, the threshold is about 50 ppm. In some embodiments, the threshold is about 45 ppm. In some embodiments, the threshold is about 40 ppm. In some embodiments, the threshold is about 35 ppm. In some embodiments, the threshold is about 30 ppm. In some embodiments, the threshold is about 25 ppm. In some embodiments, the threshold is about 20 ppm. In some embodiments, the threshold is about 15 ppm. In some embodiments, the threshold is about 10 ppm. In some embodiments, the threshold is about 5 ppm. In some embodiments, the threshold is about 1 ppm. In some embodiments, the threshold is about 0.1 ppm. In some embodiments, the threshold is about 0.01 ppm. In some embodiments, the threshold is about 0.001 ppm.

The followings describe some embodiments of the filter element that comprises a fluororesin porous layer laminated on at least one surface of the substrate, wherein the photocatalytic composition is disposed on the fluororesin porous layer. Note that the layer dimensions, including thickness and length, and other conditions such as lamination state depicted in the drawing do not necessarily reflect the actual layers.

Figure 39:
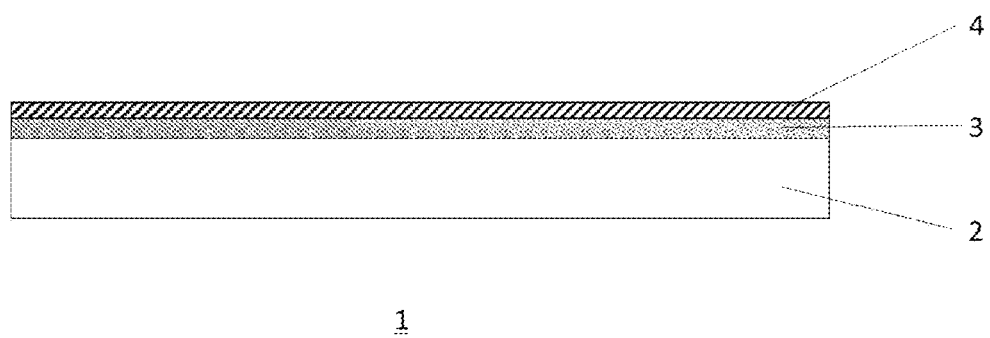
FIG. 39 is a cross sectional view of an embodiment of a filter element, that includes a fluororesin porous layer.

FIG. 39 is a cross sectional view of an embodiment of a filter element, that includes a fluororesin porous layer.

As shown in FIG. 39, an embodiment of a filter element 1 includes a fluororesin porous layer 3 laminated on a gas permeable support 2, and a photocatalyst layer 4 that contains at least a photocatalyst, and is formed on the fluororesin porous layer 3. Herein, the following embodiments are just non-limiting embodiments, and the substrate, photocatalytic composition and the like that constitute the filter element may be any one of those mentioned above. In addition, the followings may be applied to other embodiments of a filter element and a system.

A filter element of this embodiment includes a fluororesin porous layer between a gas permeable support and a photocatalyst layer. The fluororesin porous layer is highly durable against the photocatalysis (photooxidation effect) of the photocatalyst contained in the photocatalyst layer, and effectively prevents the corrosion, discoloration, or deterioration caused by the photooxidation effect in the gas permeable support of the filter element. The filter element of this embodiment can thus have high durability while maintaining the photocatalytic activity of the photocatalyst. The filter element of this embodiment also satisfies the trapping efficiency, the pressure loss, and other such properties generally desired of a filter element.

The gas permeable support 2 is not particularly limited, and any known support may be used according to the properties desired in different applications of the filter element. In some embodiments, the gas permeable support is an air permeable support.

Preferably, the gas permeable support 2 is one that has better gas permeability than the fluororesin porous film 3 (described later), and that can serve as a reinforcing material. The basis weight and the thickness of the gas permeable support 2 are not particularly limited, and may be selected according to the desired filter element performance. The basis weight is, for example, 5 g/m$^2$ to 400 g/m$^2$, preferably 5 g/m$^2$ to 80 g/m$^2$. Considering strength, the thickness of the gas permeable support 2 is, for example, preferably 0.05 mm to 1 mm, more preferably 0.05 mm to 0.8 mm.

The gas permeable support 2 is not limited to a particular shape, and may use various porous materials, for example, such as fabric, nonwoven fabric, a metal or plastic mesh (mesh sheet), a metal or plastic net, a plastic foam, and a felt. For example, considering properties such as strength, ease of trapping, flexibility, and ease of handling, it is preferable to use a nonwoven fabric or a mesh for the gas permeable support 2. Examples of the material of the gas permeable support 2 include polyolefins such as polyethylene, and polypropylene; polyesters such as polyamide, and polyethylene terephthalate; and polymers such as aromatic polyamide, acryl, polyimide, polysulfone, polyamideimide, polyphenylene sulfide, polyvinylidene fluoride, cellulose polymer, and viscose. When the gas permeable support 2 is formed of fiber material, the fiber used may be a synthetic fiber, such as the polymers exemplified above, or a composite material of such synthetic fibers. It is also possible to use a glass fiber. Examples of other usable materials include spunbonded nonwoven fabrics of a core-in-sheath structure, for example, such as a PE (polyethylene)/PET (polyethylene terephthalate) spunbonded nonwoven fabric, and a polyester/polyethylene spunbonded nonwoven fabric.

In this embodiment, the fluororesin porous layer (fluororesin porous film) 3 is laminated on the gas permeable support 2. The photocatalyst layer 4 (described later) is provided on the fluororesin porous layer 3. That is, in this embodiment, the fluororesin porous layer 3 exists between the gas permeable support 2 and the photocatalyst layer 4. The fluororesin porous layer 3 has excellent durability against the photocatalysis (photooxidation effect) of the photocatalyst contained in the photocatalyst layer 4. Therefore, in this embodiment, the gas permeable support 2 laminated on the side of the fluororesin porous layer 3 opposite the photocatalyst layer 4 can be effectively prevented from the corrosion, discoloration, or deterioration caused by the photocatalysis of the photocatalyst.

Examples of the fluororesin for constituting the fluororesin porous layer 3 in this embodiment include polyvinylidene fluoride, polytetrafluoroethylene (hereinafter, also referred to as "PTFE"), an ethylene-tetrafluoroethylene copolymer, a tetrafluoroethylene-hexafluoropropylene copolymer, and a tetrafluoroethylene-perfluoroalkyl vinyl ether copolymer. The fluororesin may be used alone or in a combination of two or more. Preferably, the fluororesin for constituting the fluororesin porous layer 3 contains PTFE, because such fluororesin is particularly excellent in properties such as versatility, particle trapping, and durability.

Preferred for use as the fluororesin porous layer 3 is a material with an average pore size of 0.1 μm to 10 μm, more preferably 0.1 μm to 2 μm. Trapping efficiency may suffer when the average pore size of the fluororesin porous layer 3 exceeds 10 μm. On the other hand, pressure loss may increase when the average pore size of the fluororesin porous layer 3 is less than 0.1 μm.

The thickness of the fluororesin porous layer 3 is preferably 1 μm to 50 μm, more preferably 1 μm to 20 μm. Pressure loss may increase when the thickness of the fluororesin porous layer 3 exceeds 50 μm. On the other hand, strength may suffer when the thickness of the fluororesin porous layer 3 is less than 1 μm.

The fluororesin porous layer 3 is available as a commercially available product, or may be produced according to a known method. As an example, a PTFE porous film using PTFE as the fluororesin may be produced by stretching a PTFE sheet obtained by paste extrusion of a raw material PTFE fine powder. The area stretch rate (the sum of the stretch rate in one axial direction and the stretch rate of the direction perpendicular to this direction) of the stretched PTFE sheet may be about 100 to 500 times.

In this embodiment, the photocatalytic composition is provided in a form of a photocatalyst layer 4 on the fluororesin porous layer 3 laminated on the gas permeable support 2. In FIG. 39, the photocatalyst layer 4 completely covers the surface of the fluororesin porous layer 3 opposite the surface in contact with the gas permeable support 2. However, the present invention is not limited to this embodiment, and the photocatalyst layer 4 may be formed so as to cover only a part of the surface of the fluororesin porous layer 3 opposite the surface in contact with the gas permeable support 2.

In this embodiment, the photocatalyst layer 4 contains at least a photocatalyst. In some embodiments, in addition to the photocatalyst, the photocatalyst layer 4 may contain a co-catalyst, as desired. The photocatalyst contained in the photocatalyst layer 4 and the co-catalyst contained as desired in the photocatalyst layer 4 may be those described above.

Production processes of this embodiment of a filter element are described below.

Methods of laminating the gas permeable support and the fluororesin porous layer are described first. Methods used to laminate the gas permeable support and the fluororesin porous layer are not particularly limited, and, for example, these may be simply layered together, or may be bonded to each other. The bonding methods are not particularly limited, and may be, for example, a method including laminating the layers with a thermofusion net or mesh placed in between, a method including bonding the layers after applying an adhesive to at least one of the layers in a form of fine dots or lines, or a method including bonding the layers with a hot-melt adhesive. The adhesive may be, for example, a two-part adhesive, or a heat self-crosslinking adhesive. Preferable examples of the two-part adhesive include an epoxy resin. Preferred examples of the heat self-crosslinking adhesive include a vinyl acetate-ethylene copolymer, and an ethylene-vinyl chloride copolymer.

In addition, the gas permeable support, when made of material such as nonwoven fabric, may be partially melted, and laminated to the fluororesin porous layer under heat. For example, when the gas permeable support is entirely or partially made of thermoplastic resin such as polyethylene (for example, a gas permeable support made of nonwoven fabric), some of the fibers in the gas permeable support melt and bond to the fluororesin porous layer upon laminating the gas permeable support on the fluororesin porous layer under appropriate conditions (for example, under heat and pressure). When using, for example, a nonwoven fabric, the bonding occurs only on the fibers of the nonwoven fabric, and air permeability is ensured in regions where the fiber is absent.

Methods of forming the photocatalyst layer on the fluororesin porous layer are described below.

The methods used to form the photocatalyst layer are not particularly limited, and the photocatalyst layer may be formed by using, for example, dry deposition methods such as aerosol deposition methods (also referred to as AD method, or gas deposition method), high velocity oxygen fuel (HVOF) spraying, cold spraying, atomic layer deposition (ALD), chemical vapor deposition (CVD), and physical vapor deposition (PVD), and wet deposition methods such as spin coating, and dip coating. The aerosol deposition method is particularly preferred for its ability to provide excellent photocatalytic activity for the photocatalyst layer, and excellent adhesion for the fluororesin porous layer.

The filter element in this embodiment can be produced by laminating the gas permeable support and the fluororesin porous layer as above, and forming the photocatalyst layer on the fluororesin porous layer. In producing the filter element of this embodiment, the photocatalyst layer may be formed on the fluororesin porous layer after laminating the gas permeable support and the fluororesin porous layer. Alternatively, the filter element may be produced by first forming the photocatalyst layer on the fluororesin porous layer, and then laminating the gas permeable support and the fluororesin porous layer supporting the photocatalyst layer. In forming the photocatalyst layer on the fluororesin porous layer, the photocatalyst is supported on the fluororesin porous layer in amounts of preferably about 0.1 to 5 $g/m^2$.

One or more layers in the filter element of this embodiment may be subjected to various treatments such as a deodorant treatment, an anti-microbial treatment, and a color treatment as may be decided according to the properties desired in different applications of the filter element. For the deodorant treatment of the gas permeable support, for example, a deodorant compound may be attached to or may impregnate the surface of the gas permeable support via a polymer, or a deodorant compound may be mixed with the raw material of the gas permeable support, and this mixture may be used to produce the gas permeable support. The gas permeable support can retain the deodorant compound after these procedures. The gas permeable support also can retain an anti-microbial agent after an anti-microbial treatment performed by using the same technique. The gas permeable support also may be subjected to a color treatment intended to, for example, obscure any discoloration of the filter element caused by the trapped particles. These and other treatments also may be performed for layers (for example, the fluororesin porous layer) other than the gas permeable support by using the same technique.

In the filter element of this embodiment, layers other than the gas permeable support, the fluororesin porous layer, and the photocatalyst layer also may be laminated as required, provided that such additional layers do not interfere with the intended object thereof (such additional layers will also be referred to as "other layers"). For example, the gas permeable support and the fluororesin porous layer may be laminated either directly or via other layers. Similarly, the fluororesin porous layer and the photocatalyst layer may be laminated either directly or via other layers.

In the filter element 1 according to this embodiment represented in FIG. 1, the fluororesin porous layer 3 is laminated only on one surface of the gas permeable support 2, and the photocatalyst layer 4 is formed on the fluororesin porous layer 3. However, this embodiment is not a limiting one, and, for example, the fluororesin porous layer may be laminated on the both surfaces of the gas permeable support, and the photocatalyst layer may be formed on one of or both of those fluororesin porous layers in some embodiments.

The filter element of some embodiments may include a plurality of gas permeable supports, a plurality of fluororesin porous layers, and/or a plurality of photocatalyst layers, provided that it does not interfere with the intended object thereof. In those embodiments, at least one of the outermost layers of the filter element is preferably the photocatalyst layer so that the photocatalyst layer can more effectively exhibit photocatalytic activity under light. In those embodiments, the gas permeable support and the photocatalyst layer may not be in contact with each other, in order to effectively prevent any corrosion, discoloration, or deterioration of the gas permeable support caused by the photooxidation reaction catalyzed by the photocatalyst.

The filter element of some embodiments may be subjected to a pleating process, as required. The pleat shape is not particularly limited. The pleating process may be a continuous process whereby the filter element is continuously processed as it is sent out in the shape of a flat plate, or may be a process that pleats the filter element (unit plate) cut into appropriate dimensions. Known pleating machines (for example, such as a rotary pleating machine, a reciprocating pleating machine, and a creasing pleating machine) may be used for the pleating of the plate-shaped filter element. It is preferable to use a reciprocating pleating machine from the standpoint of suppressing damage to the filter element during the pleating process.

The total thickness of the filter element of some embodiments is not particularly limited, and is, for example, 0.05 mm to 1 mm. Preferably, the total thickness ranges from, for example, 0.05 mm to 0.8 mm, particularly when the pleating process is performed as above.

At a flow rate of 5.3 cm/s, the filter element of some embodiments has a trapping efficiency of preferably 99.97% or more, more preferably 99.99% or more for particles having a particle size of 0.1 to 0.3 µm. The pressure loss at a flow rate of 5.3 cm/s is preferably 245 Pa or less, more preferably 100 Pa or less, and the lower limit is not particularly limited. The trapping efficiency and the pressure loss may be measured by using the methods below.

Pressure loss may be measured as follows, for example. Specifically, a sample is set on a circular holder having an effective area of 100 cm$^2$, and a pressure difference is created between the inlet and outlet sides while supplying lithometeor from the inlet side. The lithometeor is passed at the air permeation flow rate of 5.3 cm/sec adjusted with a flowmeter, and the pressure loss (unit Pa) is measured with a pressure gauge (manometer). Preferably, the measurement is performed at multiple points (for example, 5 points) per sample, and the average of the measured values is determined as the pressure loss of the sample. Note that the lithometeor is dust falling through the atmosphere.

Trapping efficiency may be measured as follows, for example. Specifically, by using the same device used for the pressure loss measurement, polydisperse dioctyl phthalate (DOP) particles having a particle size of 0.1 µm to 0.15 µm are supplied to the upstream side of a sample at the adjusted air permeation flow rate of 5.3 cm/sec. Here, the particles are supplied to provide $10^7$ particles per liter. The particle concentration on the upstream side, and the downstream particle concentration after the passage through the sample can then be measured with a particle counter (KC-80; Rion Co., Ltd.) to determine trapping efficiency (%) according to the following equation.

Trapping efficiency (%)=[1−(downstream concentration/upstream concentration)]×100

(Unit of downstream particle concentration: particles/liter)

(Unit of upstream particle concentration: particles/liter)

A filter unit of some embodiments includes the filter element of some embodiments. The other configuration and structure of the filter unit are not particularly limited, as long as the filter unit includes the filter element of some embodiments. The filter element of some embodiments may be used as a replacement of the filter element of conventionally known filter units.

The filter element of some embodiments is potentially useful, for example, as a filter element in applications such as air filter units for clean rooms, and filter units for home electric appliances. The filter element of some embodiments is particularly preferred for use as an air filter element.

SAMPLE PREPARATION

All materials were used without further purification unless otherwise indicated. All materials were purchased from Sigma Aldrich (St. Louis, Mo., USA) unless otherwise indicated.

Example 1

$WO_3$ photocatalyst (200 mg), as prepared according to the method described earlier in this disclosure, was added to water. The resulting dispersion was then added to 740 mg of $CeO_2$ sol (Nissan Chemical America, Houston, Tex., USA, NanoUse CE-20B). The mole ratio of $CeO_2$ and $WO_3$ was chosen to be 1:1 (50 molar % to 50 molar %). Then a sufficient amount of RO (reverse osmosis treated) water (800 mg) was added to the resulting dispersion in order to make a coating solution which is about 20 wt % solid materials in water. The resulting dispersion was homogenized using an ultrasonic homogenizer. A glass substrate (50 mm×75 mm) was coated with the prepared resultant by using a spin coater (1200 rpm/40 sec). The coated substrate was heated for about 2 minutes at about 120° C. The resulting coated substrate was transparent (about 86% at about 555 nm). Photocatalytic activity was determined by monitoring the acetaldehyde degradation ratio to about 81% after 1 hour of blue light-emitting diode (LED) (450 nm, 200 mW/cm$^2$) irradiation.

Example 2

Coated substrate 2 was made in a similar manner to Example 1, except that $SiO_2$ sol (Nissan Chemical SNOWTEX O, 258 mg) was added instead of $CeO_2$ sol. The resulting coated substrate was transparent (90% at about 555 nm). Photocatalytic activity as determined by the acetaldehyde degradation ratio was about 50% after irradiation under conditions similar to Example 1.

Example 3

Coated substrate 3 was made in a similar manner to Example 1, except that $SiO_2$ sol (Nissan-Chemical SNOWTEX 20L, 258 mg) was added instead of $CeO_2$ sol. The resulting obtained substrate was transparent (91% at 555 nm). Photocatalytic activity as determined by the acetaldehyde degradation ratio was about 67% after irradiation under conditions similar to Example 1.

Example A

Example A was prepared in a manner similar to Example 1, except that silicone resin (Shin-Etsu Chemical, SCR-1012) was used instead of $CeO_2$ sol. The ratio of $WO_3$ was about 20 wt % in silicone resin. Glass substrate (50 mm×75 mm) was coated with the prepared solution by doctor blade. After 120° C. heating for curing, the obtained substrate was translucent. The resulting obtained substrate exhibited a transparency of about 75% at 555 nm. Photocatalytic activity as determined by the acetaldehyde degradation ratio was about 1% after irradiation under conditions similar to Example 1.

Example B

Example B was prepared in a manner similar to Example 1, except that poly(methyl methacrylate) (PMMA) was dispersed in acetone. The ratio of $WO_3$ was about 20 wt % in PMMA and no water was added. Glass substrate (50 mm×75 mm) was coated with the prepared solution by doctor blade. After 120° C. heating for curing, the obtained substrate was translucent. The resulting obtained substrate exhibited a transparency of about 78% at 555 nm. The acetaldehyde degradation ratio was 0.5% after irradiation under conditions similar to Example 1.

Example 4

30 mL of 5 mM Tungstic acid ($WO_3.H_2O$) and 30 mL of HF2% solution (e.g., $WO_3$ precursor), were added to 40 ml of boric acid ($H_3BO_3$). Two 75 mm×25 mm silicon wafers were immersed in the resulting solution and stirred for about 6 hours at about 30° C. The layered substrate was removed from the solution and annealed at about 400° C. for about 1 hour resulting in a coated glass slide (Example 4). A coating solution was prepared with sufficient $CeO_2$ sol (Nissan Chemical NanoUse CE-20B) to attain a mole ratio of $CeO_2$ and $WO_3$ of about 1:1 (50 molar % to 50 molar %). Example 4a was then made by spin coating the substrate of Example 4, as discussed above, with the $CeO_2$ coating solution in a manner similar to that described in Example 1.

Figure 3B:
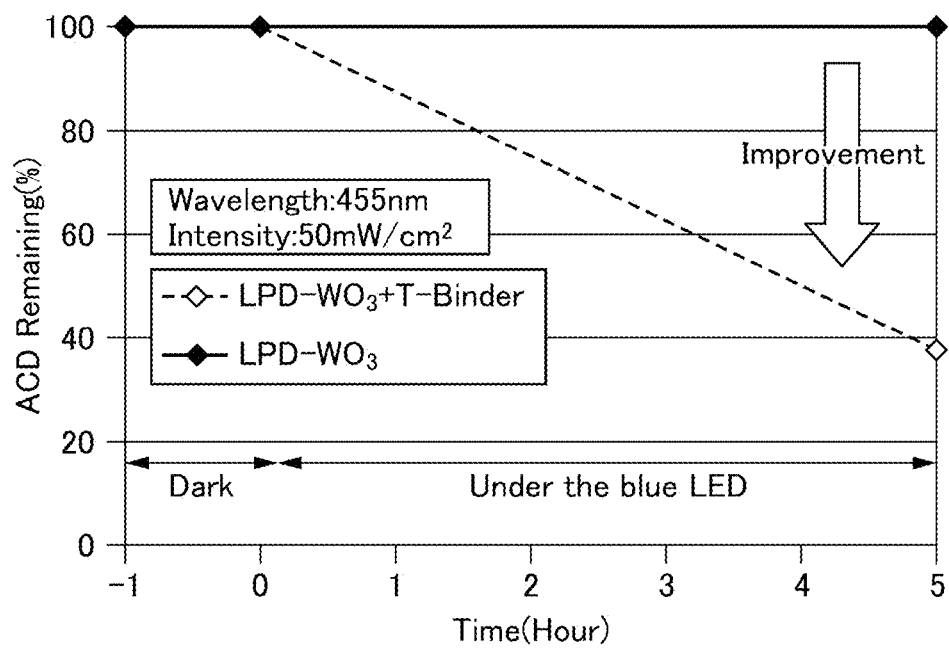
FIG. 3B is a graph illustrating T-binder performance data.

The spin coated glass slides, prepared in accordance with Example 4 and 4a above, were heated at about 120° C. on a hot plate under full spectrum irradiation by a Xe lamp (lamp power output about 300 W) for about 1 hour. Each slide was then sealed in a separate 5 L Tedlar bag under vacuum, followed by Injecting about 3 L of ambient air and about 80 mL of 3500 ppm acetaldehyde. Each bag was lightly massaged for about 2 minutes by hand then placed in the dark for about 15 min. The acetaldehyde concentration was estimated by Gas Chromatography-Flame Ionization Detector (GC-FID) (GC-2010 Plus gas chromatograph, Shimadzu Scientific Instruments, Inc, Carlsbad, Calif., USA; and Restek Rt-Q Bond (fused silica BOND column) (Restek Corp., Bellefonte, Pa., USA) to be at 80±2 ppm. Each Tedlar bag containing a sample was placed back in the dark for about 1 hour. The slide/Tedlar bag was exposed to array blue LED of 455 nm with light intensity of 50 $mW/cm^2$. A sample was collected every 30 minutes by an automated injection port of GC-FID and the amount of remaining acetaldehyde was estimated at subsequent 30 minute Intervals. FIG. 3B is a graph illustrating T-binder performance data. The graph shows that generally when a T-binder is combined with $WO_3$, performance is improved when compared to bare $WO_3$.

Examples 5-7

5 g of $WO_3$ (Global Tungsten & Powder, Towanda, Pa., USA [GTP]) was added to high purity alumina ball mill jars containing about 50 g of $ZrO_2$ balls of about 3 mm in diameter and was ground by ball mill (SFM-1 model Desktop Planetary Ball Miller (MTI Corp. location) in 25 mL methanol for about 4 hours to obtain ground $WO_3$ (GTP) with a smaller particle size. Plasma-$WO_3$ was made in a manner similar to that described in U.S. Pat. No. 8,003,563, which is hereby incorporated by reference in its entirety.

Additional glass slides were made and placed in a Tedlar bag in a similar manner to that described in Example 4, except that 200 mg each of $WO_3$ (GTP) (Example 5 w/, Example 5a w/out), Ground $WO_3$ (GTP) (Example 6 w/, Example 6a w/out) and plasma-$WO_3$ (Example 7 w/, Example 7a w/out) each with and without $CeO_2$ were spin-coated on glass substrate instead of LPD-$WO_3$. When $CeO_2$ was used, the molar ratio of each type of $WO_3$ to $CeO_2$ was 1:1.

Figure 4:
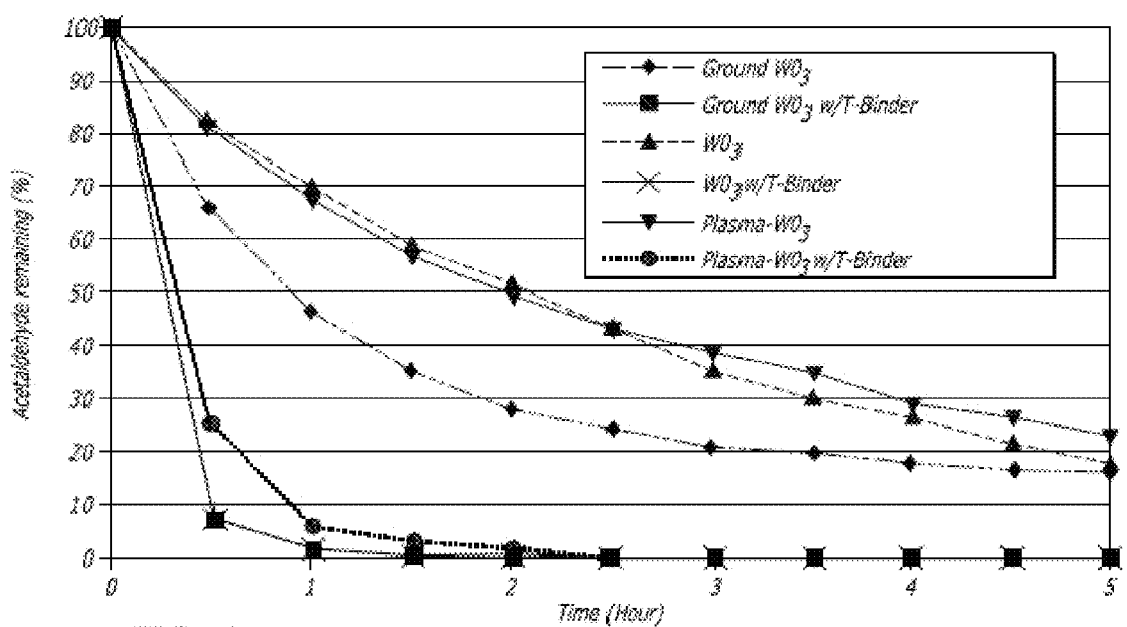
FIG. 4 is a plot of acetaldehyde decomposition for the photocatalyst compositions of Examples 5-7.

The spin-coated slides $WO_3$, Ground $WO_3$, find and plasma-$WO_3$ each with and without $CeO_2$ were prepared and were tested for acetylaldehyde degradation as described in Example 4. The results are shown in FIG. 4.

Examples 8A-8J

Figure 5:
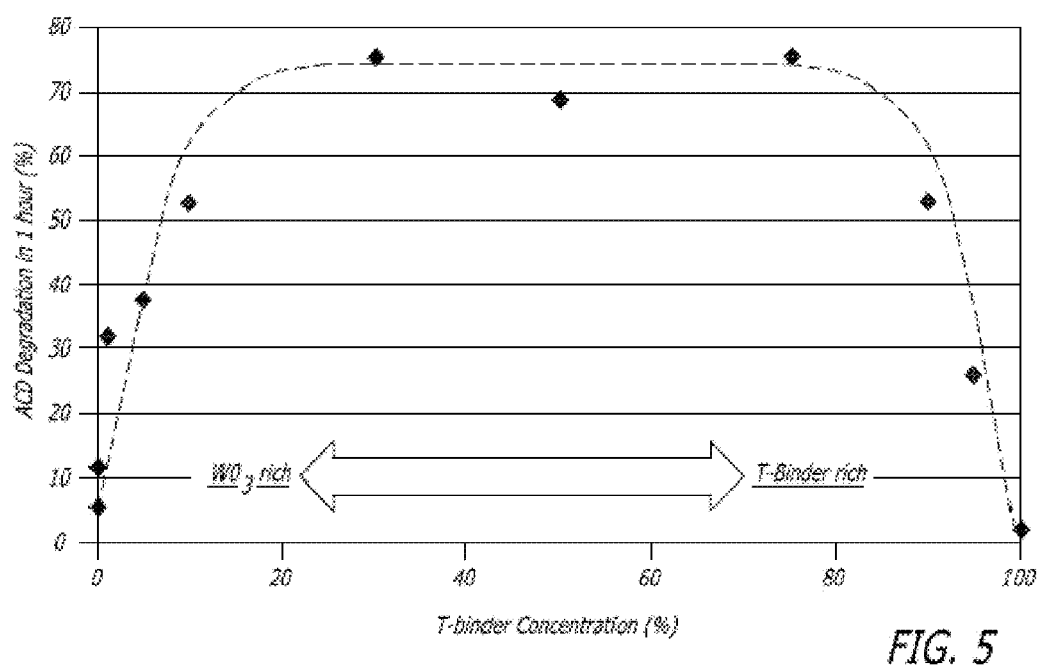
FIG. 5 is a plot of acetaldehyde decomposition at one hour for a photocatalyst composition comprising $WO_3$ and T-binder at various ratios.

In another example (Example 8), additional slides were made in a manner similar to that of Example 1, except that the amount of $CeO_2$ sol added was varied to attain different molar ratios of $WO_3$:$CeO_2$ (e.g., 0%, 0.1%, 5%, 10%, 30%, 50%, 75%, 90%, 95%, 100%) ((100–x) $WO_3$+(x) T-binder). FIG. 5 shows the acetaldehyde degradation estimated after 1 hour of exposure to 270 $mW/cm^2$ blue LED array light.

Examples 9-15

In another example (Example 9), an additional slide was made in the following manner: plasma $WO_3$ powder (130 mg) and $CeO_2$ powder (96.5 mg) (about a 1:1 mole ratio) were dispersed first in RO water (20 wt % of solid) and bath sonicated (VWR B3500A-MT) for about 10 minutes and then probe sonicated (Sonic dismembrator Model 100, continuous mode) for about 5 minutes. Then, the mixture/composite/blend was spin coated on a 75 mm×50 mm glass slide and annealed as described in Example 4.

Additional slides were made in a similar manner, except that various other materials were used instead of $CeO_2$, as set forth in Table 1:

TABLE 1

| Example | Plasma $WO_3$ | T binder Material |
|---|---|---|
| 9 | 130 mg | Aldrich $CeO_2$ = 96.5 mg |
| 10 | 130 mg | Anatase $TiO_2$ = 44.78 mg |
| 11 | 130 mg | $KTaO_3$ = 150.3 mg |
| 12 | 130 mg | $KNbO_3$ = 100.93 mg |
| 13 | 130 mg | $SrTiO_3$ = 102.89 mg |
| 14 | 130 mg | SiC = 22.5 mg |
| 15 | 130 mg | $TiO_2$ = 44.78 mg and $CeO_2$ = 96.5 mg |

Figure 6:
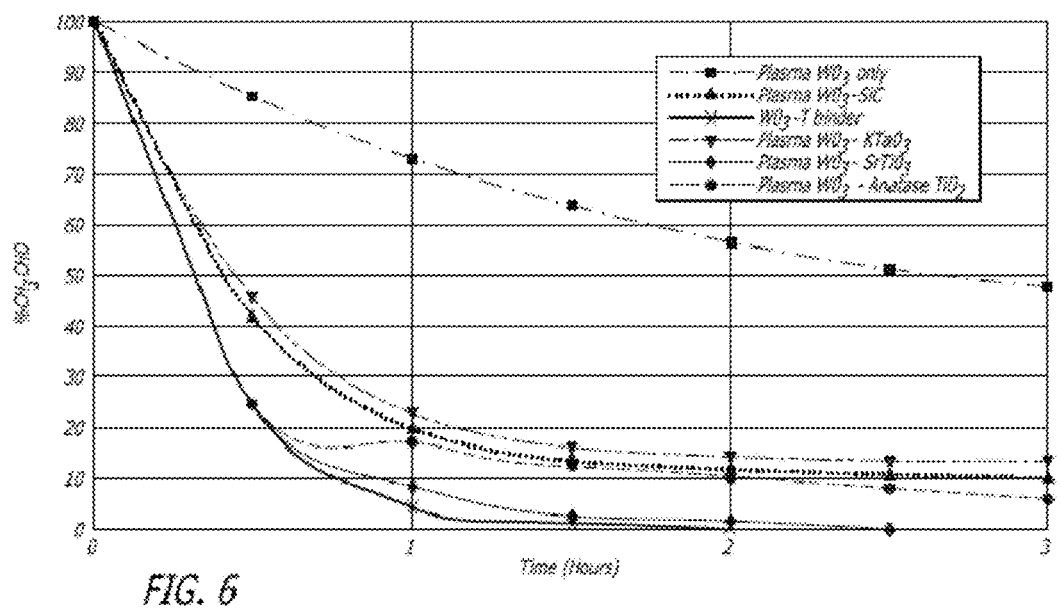
FIG. 6 is a plot of acetaldehyde decomposition for the photocatalyst compositions of Examples 9-15.

Each glass slide was tested for acetylaldehyde degradation in a manner similar to that described in Example 4, except that the applied light intensity was about 270 $mW/cm^2$. The results are shown in FIG. 6.

Figure 7:
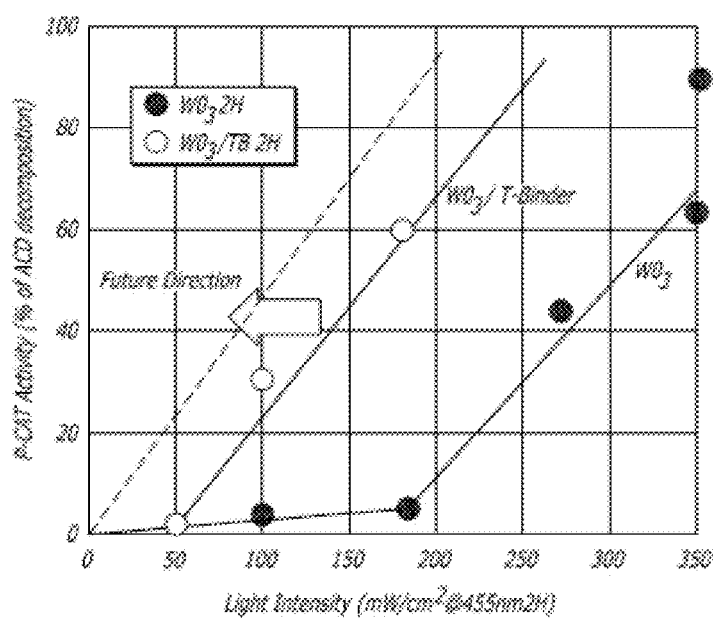
FIG. 7 is a plot of acetaldehyde decomposition for $WO_3$ and $WO_3$/T-Binder at varying light intensity at 455 nm.

In another example, each glass slide made above was tested in a manner similar to that described immediately above, except that each slide was exposed to varied light intensity (from about 50 $mW/cm^2$ to about 350 $mW/cm^2$). The results are shown in FIG. 7.

Examples 16-30

In addition, in another example, about 130 mg of powdered sample from various compounds (see Table 2) were each separately dissolved in a minimal amount of RO water and homogenized for about 5 minutes. The compounds were then combined with $WO_3$ in a 1:1 molar ratio according to the process described in Example 1.

TABLE 2

| | Example | | | | | | | |
|---|---|---|---|---|---|---|---|---|
| | 16 | 17 | 18 | 19 | 20 | 21 | 22 | 23 |
| compound | CuO | $MoO_3$ | $MnO_3$ | $Y_2O_3$ | $Gd_2O_3$ | $CeO_2$-combustion | Plasma $WO_3$ | $Nb_2O_5$ |

| | Example | | | | | | |
|---|---|---|---|---|---|---|---|
| | 24 | 25 | 26 | 27 | 28 | 29 | 30 |
| compound | $In_2O_3$ | $Ta_2O_5$ | Rutile + Anatase $TiO_2$ | $CeO_2$ (Nissan Chemicals America) | $CeO_2$ (Aldrich) | Plasma $CeO_2$ | Anatase $TiO_2$ anatase |

Figure 8:
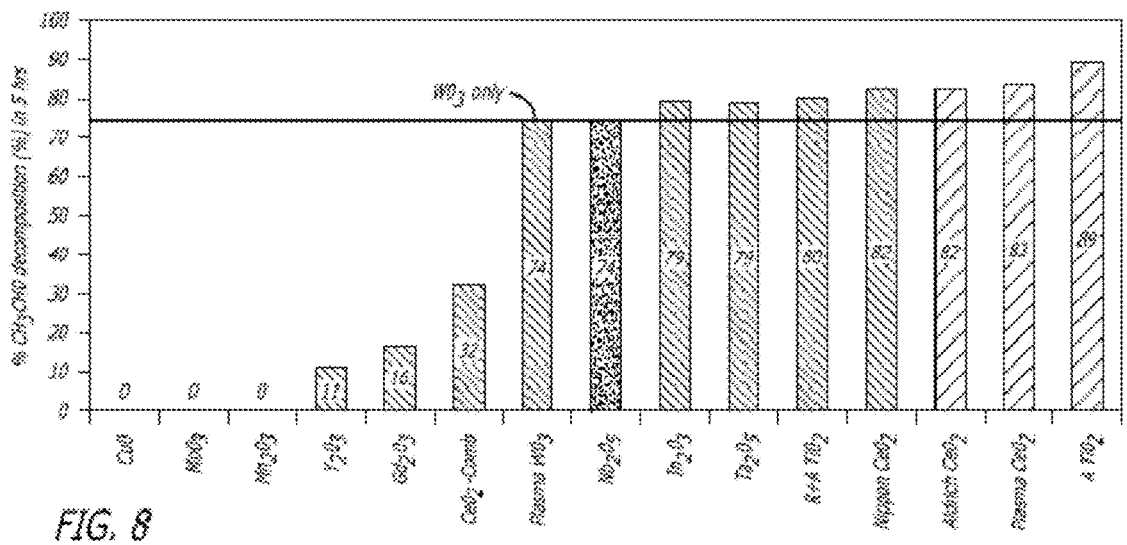
FIG. 8 is a graph of acetaldehyde decomposition after 5 hours for $WO_3$ with co-catalysts of Examples 16-30 at a 1:1 molar ratio.

A clean petri dish was wiped with ethanol and the inside surface of the dish was ionized with a corona device for about 1 to 2 minutes. The homogeneous sample of each compound was poured into the treated petri dish and then heated at about 120° C. while swirling to achieve uniform distribution of the sample as it dried. After the sample had dried, the petri dish was placed under a UV lamp (300 W) for about 1 hour. The petri dish was then inserted into a Tedlar bag and tested in a manner similar to that described for Example 4. The results are shown in FIG. 8.

Example 31-35

In another example, 3.78 g of Tin (II) 2-ethylhexanoate [also known as tin (II) octoate and/or stannous octoate] (Spectrum Chemicals, Gardena, Calif., USA), 5 g of $Ce(NO_3)_3 \cdot 6H_2O$ (Sigma Aldrich, St. Louis, Mo., USA), and 3.0 g of ammonium nitrate ($NH_4NO_3$) (Sigma Aldrich, St. Louis, Mo., USA) were dissolved in about 25 mL of RO treated water. 1.129 g maleic hydrazide was then added just before the mixture was heated to about 150° C. and stirred for about 20 minutes.

The resultant precursor mixture was then heated at about 450° C. for about 40 minutes in a preheated muffle furnace under ambient atmosphere and pressure conditions. The resultant powder was annealed at about 500° C. for about 20 minutes. The resultant powder was mixed with $WO_3$ in a 1:1 molar ratio used in a manner similar to that described in Example 1 to make a coated glass slide and then was tested on its ability to degrade acetylaldehyde following the procedure described in Example 4.

Other powders were made in a similar manner, except that the amounts, of materials and/or other parameters were used as set forth in Table 3:

TABLE 3

Combustion synthesis of Tin doped and undoped $CeO_2$

| Nominal Composition | Precursors amount | Combustion temperature | Annealing temperature |
|---|---|---|---|
| Example 31 [7.5 mol % Sn in $CeO_2$] | $Ce(NO_3)_3 \cdot 6H_2O$ = 5 g<br>Sn octoate = 0.378 g<br>$NH_4NO_3$ = 3 g<br>Maleic Hydrazide = 1.129 g | 450° C. | 500° C./ 20 min |
| Example 32 [5 mol % Sn in $CeO_2$] | $Ce(NO_3)_3 \cdot 6H_2O$ = 5 g<br>Sn octoate = 0.245 g<br>$NH_4NO_3$ = 3 g<br>Maleic Hydrazide = 1.127 g | 450° C. | 500° C./ 20 min |
| Example 33 [2.5 mol % Sn in $CeO_2$] | $Ce(NO_3)_3 \cdot 6H_2O$ = 5 g<br>Sn octoate = 0.1196 g<br>$NH_4NO_3$ = 3 g<br>Maleic Hydrazide = 1.129 g | 450° C. | 500° C./ 20 min |
| Example 34 [0 mol % Sn in $CeO_2$] | $Ce(NO_3)_3 \cdot 6H_2O$ = 5 g<br>Maleic Hydrazide = 1.129 g | 450° C. | 500° C./ 20 min |
| Example 35 [0 mol % Sn in $CeO_2$] | $Ce(NO_3)_3 \cdot 6H_2O$ = 5 g<br>Maleic Hydrazide = 1.129 g | 300° C. | — |

Figure 9:
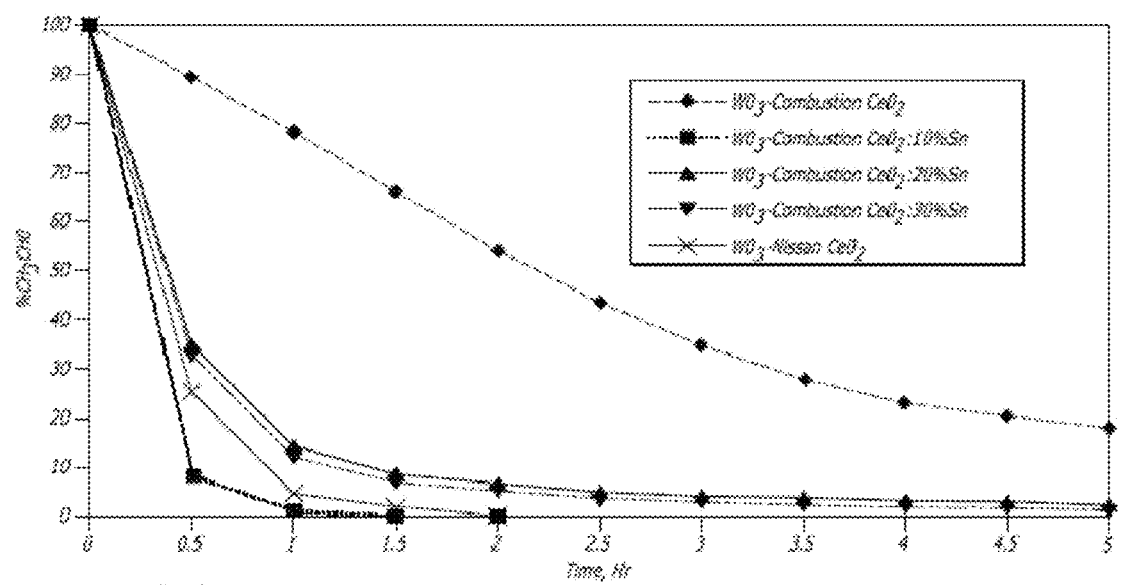
FIG. 9 is a plot of acetaldehyde decomposition for the photocatalyst compositions of Examples 31-35.

The combustion synthesized powders were incorporated in a similar manner onto a glass slide as described in Example 3 and was tested as described in Example 4. The results are shown in FIG. 9. As seen in FIG. 9, $WO_3$ combined with Sn doped $CeO_2$ showed enhanced acetaldehyde degradation as compared with $WO_3$ combined with undoped $CeO_2$.

Example 36

Combination of Combustion $Ti(O,C,N)_2$:Sn and Plasma $CeO_2$ Towards Acetaldehyde Degradation In another example, $Ti(O,C,N)_2$:Sn was combined with plasma $CeO_2$ powder (1:1 mole ratio) in a similar manner to that described in Example 1, except that $Ti(O,C,N)_2$:Sn powder was used instead of $WO_3$ powder, and was spin coated on a glass micro slide as described in Example 1. The $Ti(O,C,N)_2$:Sn was synthesized as described in co-pending U.S. Patent Provisional Application Ser. No. 61/608,754, filed Mar. 8, 2012, which is hereby incorporated by reference in its entirety, by an aqueous combustion method employing glycine (1.4 g) as a completely decomposable fuel in addition to titanium (IV) bis ammonium lactate dihydroxide (7 mL of 50 wt % aqueous solution), tin octoate (0.883 g) and ammonium nitrate (3.5 g) at 300° C. followed by annealing at 400° C. for 30 min in the box furnace. A glass slide made in a manner similar to that of the previous examples was tested for acetaldehyde degradation as also earlier described in Example 4 (at 270 mW/cm² light intensity). 7% Acetaldehyde degradation was observed after 5 hours of exposure for the $Ti(O,C,N)_2$:Sn photocatalyst coated glass slide in a Tedlar bag. When, a glass slide with both $Ti(O,C,N)_2$:Sn and $CeO_2$ (1:1 mole ratio) was tested in a Tedlar bag in a similar manner, the acetaldehyde degradation increased to 22% after 5 hours of exposure.

Example 37

Decomposition Element 1500 mg of tungsten trioxide powder (Nanostructured and Amorphous Materials Inc. [Nanoamorphous Materials], Houston Tex., USA) with average particle size of 120 nm was added into a 20 ml glass vial together with 5565 mg colloidal $CeO_2$ (Ce20B, Nissan Chemicals America, Houston, Tex., USA) and about 800 mg of ultrapurified water (passed through 50 μm pore filter [Millipore Corp., Billerica, Mass., USA]). The solid content of colloidal $CeO_2$ was about 20 wt %. The mixture was first dispersed by placing in a sonication bath for 5 min. A uniform coating of the photocatalytic composition suspension was obtained by mixing the suspension with sonication probe for 10 min. The photocatalytic composition suspension was loaded onto the porous $Al_2O_3$ ceramic by dipping porous the ceramic into a petri dish containing the suspension and leaving it submerged for 5 minutes to allow the suspension to penetrate the porous ceramics. In some case, degassing was conducted to promote the penetration of suspension by removing the trapped air in the pores. The 100 mm×50 mm×5 mm porous $Al_2O_3$ ceramic impregnated with photocatalytic composition suspension was pulled from petri dish, and the extra suspension was drawn off by gravity. The photocatalytic composition loaded porous $Al_2O_3$ was first dried at ambient atmosphere at 120° C. for 1 hr in a dryer to remove the water in the coating and then annealed in a box furnace in ambient atmosphere at about 400° C. for 1 hr.

Example 38

Ethylene Decomposition System

Figure 10:
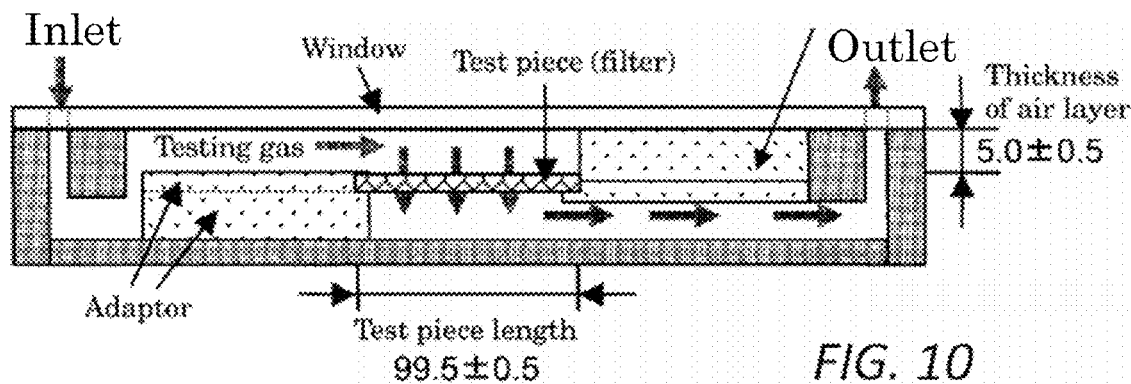
FIG. 10 is a schematic view of the testing chamber used to evaluate the rate of ethylene decomposition by photocatalytic filter elements in Example 37 and Comparative Example 39.
Figure 11:
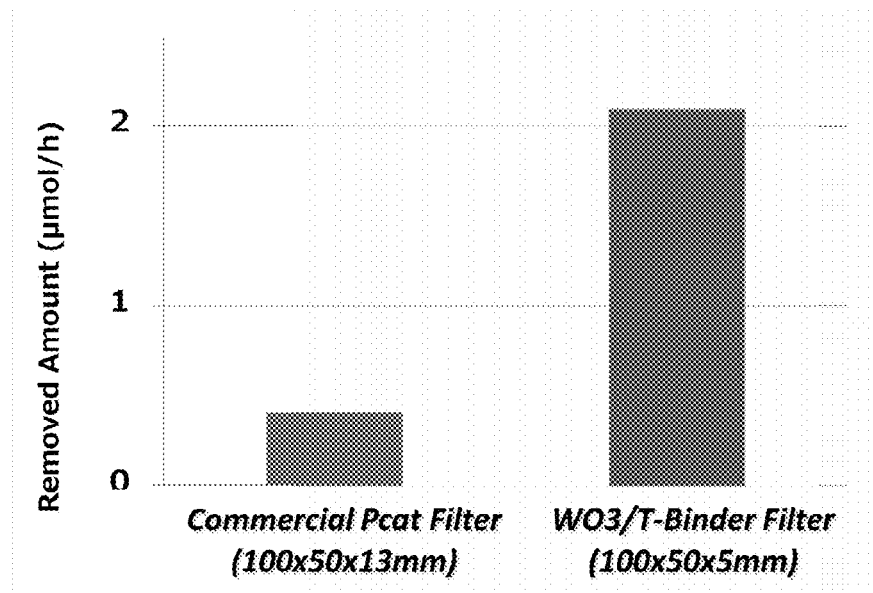
FIG. 11 is a graph of the results of the ethylene decomposition test of Example 37 and Comparative Example 39.

The prepared 100 mm×50 mm×5 mm ceramic of Example 37 was placed in a flat reaction chamber, and evaluated in a manner similar to the industrial standard evaluation JIS R1701/ISO22197-1, except as described herein, e.g., that ethylene was tested instead of acetylaldehyde. See FIG. 10. The inlet of the testing chamber supplied a continuous 1 Liter per minute flow of 5 ppm ethylene-containing purified air mixture. The mixture had a relative humidity of about 50%. The light source to activate visible photocatalyst was a blue LED array (445 nm), with a power intensity set to provide about 20 mW/cm$^2$ at the surface of the sample filter. The concentration of ethylene in the gas was measured at the outlet by a gas chromatography-flame ionization detector (GC-FID). The difference in ethylene concentration between the inlet and outlet shows the photocatalyst activity. The WO$_3$/T-binder combination filter described above removed ethylene at about 2.1 micromoles per hour. See FIG. 11.

Comparative Example 39

Ethylene Reduction Using Commercially Available Alternative

In another example, a similar setup to Example 38, except a commercially available Raymac R-15 filter (Takemura Seisakusho, Tokyo, JP) was placed in the flat reaction chamber instead of the prepared ceramic of Example 37. The filter element was cut into 100 mm×50 mm×13 mm, and evaluated by same method described in Example 38. The Raymac R15 filter removed ethylene at about 0.4 micromoles per hour. See FIG. 11.

Example 40

Flower Preservation Using Ethylene Reduction System

The decomposition element as manufactured in Example 37 was incorporated in an ethylene reduction system. The enclosing element of the ethylene reduction system was constructed from 3.5 mm thick polycarbonate sheets, and was about 155 mm wide, 155 mm high, and 85 mm between the first end and second end. In the experimental ethylene reduction system, a computer fan (Corsair Components, Inc., Fremont, Calif., USA, SP 120 High Static Pressure Case Fan, model no. CO-9050005-WW) was used as the airflow element for creating airflow. After the fan, the ethylene reduction system included a source of electromagnetic radiation comprising an array of four Blue-LEDs, specifically four Philips Lumileds LXML-PR01-0425 LEDs, located about 10 mm after the fan and about 15 mm before the ethylene reduction element. In this arrangement, the light intensity on the surface of the ethylene reduction element was about 20 mW per cm$^2$. After the Blue-LED array, and before the second end of the enclosing element, the experimental embodiment included an ethylene reduction element comprised of three Al$_2$O$_3$ ceramics, each about 100 mm wide, 50 mm high, and 5 mm think, having porosity of about 10 ppi. The resulting ethylene reduction element was effectively 100 mm×50 mm×15 mm.

In the experiment, the fan generated a flow of about 14 CFM through the 100 mm×50 mm×15 mm ethylene reduction element which was illuminated by visible light having a wavelength of about 445 nm and about 20 mW per cm$^2$. This embodiment was placed in a sealed 40 cm×40 cm×101.6 cm enclosure, along with 9 osiana roses. The osiana roses were selected because they are known to be ethylene sensitive, but not produce ethylene gas. The roses used were organically grown and did not have any ethylene related pre-treatments. Additionally, the flowers in the experimental set-up and the control were from the same source, cut on the same day, and shipped at the same time. During the experimental period, the amount of water added to the roses was controlled.

The ethylene reduction system was allowed to run for the duration of the experiment, and periodic ethylene concentration measurements were taken. The initial ethylene concentration in the enclosure was about 2.36 ppm. After about three hours, the concentration of ethylene in the enclosure had reduced to about 2.0 ppm. A second reading, taken after about 16 hours, showed the enclosure had an ethylene concentration of about 1.2 ppm. A final reading, taken after about 24 hours, showed a concentration in the enclosure of about 0.8 ppm.

After four days, the roses in the control case (Experimental Example 41 below) showed signs of deterioration, including a plurality of pedals that had fallen from the flowers and substantial yellowing of the veins in the osiana rose's leaves. The flowers in the experimental case had not lost any pedals and their leaves showed no noticeable yellowing.

Comparative Example 41

A group of 9 osiana roses in a sealed 40 cm×40 cm×101.6 cm enclosure, as in Example 40, except without the ethylene reduction system. The roses were sourced from the same grower, cut and shipped at the same time, and also not treated with any ethylene related pre-treatments. The preparation of the setup was the same as in Example 40. The Comparative Example had an initial ethylene concentration of 2.36 ppm. After 24 hours, the Comparative Example had an ethylene concentration of 1.7 ppm.

After four days, the osiana roses in the Comparative Example showed signs of ethylene exposure, including a plurality of pedals that had fallen from the flowers, and substantial yellowing of the veins in the osiana roses' leaves.

Example 42-43

Figures 12, 13:
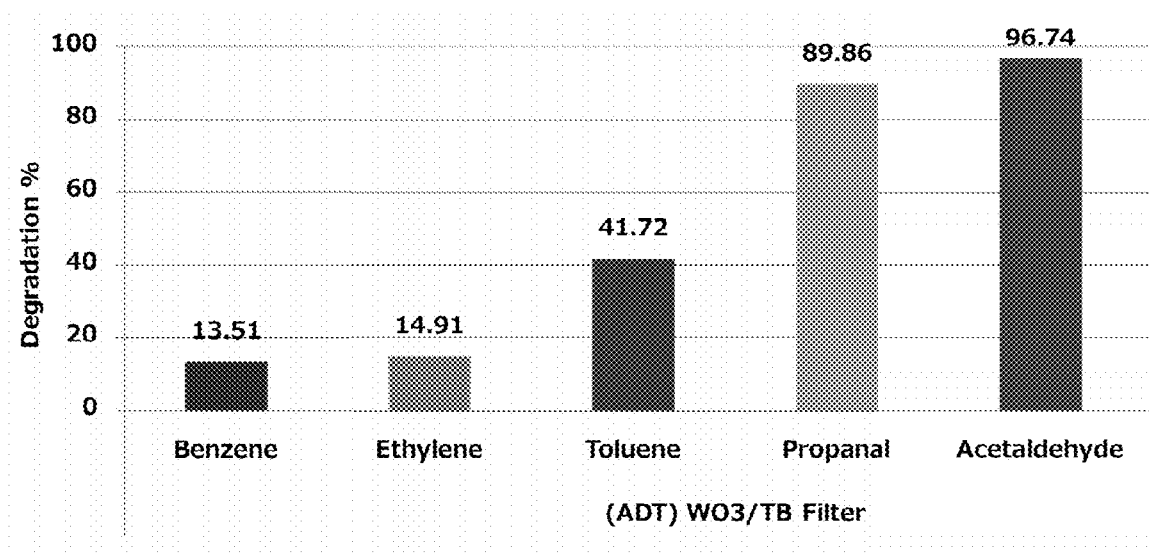
FIG. 12 is a table of the results of the acetaldehyde decomposition test of Examples 42 and 43.
FIG. 13 is a graph of the results of the benzene, ethylene, toluene, propanal, and acetaldehyde decomposition of Examples 44.

In order to optimize the ethylene reduction element, a comparison was performed between an ethylene reduction element that is 100 mm×50 mm×15 mm having porosity of 10 ppi, and an ethylene reduction element that is 100 mm×50 mm×15 mm having porosity of 30 ppi. The smaller pore size gave the 30 ppi ethylene reduction element a higher surface area and a higher airflow resistance. The 10 ppi and 30 ppi ethylene reduction elements were each coated with WO$_3$ and CeO$_2$ as in Example 37. Each ethylene reduction element was then tested using the JIS testing, as in Example 38. FIG. 12 shows the results for each embodiment's effectiveness removing acetaldehyde from the air.

Example 44

Figure 14:
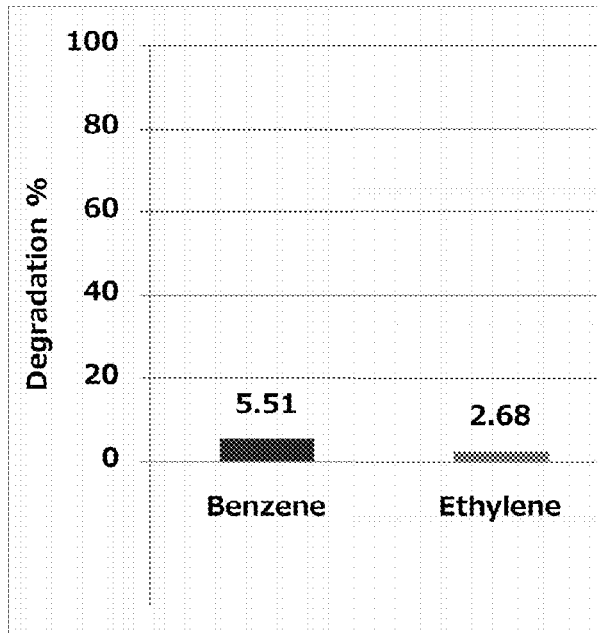
FIG. 14 is a graph of the results of the benzene and ethylene decomposition test of Comparative Example 44.

The decomposition element as described; constructed in Examples 37 and evaluated in Example 38, was also used to evaluate benzene, ethylene, toluene, propanal and acetaldehyde decomposition in a similar manner as described therein, except that the initial gas concentration was about 5 ppm for ethylene, propanal and acetaldehyde; or 2.5 ppm for benzene and toluene in artificial air, respectively. FIG. 13 shows the results for the embodiments' effectiveness removing each, from air, of benzene, ethylene, toluene, propanal and acetaldehyde. As a comparative example, commercial photo catalytic material (RENECAT WO$_3$ based material [10% dispersion in water], Toshiba Materials Co., Ltd, Tokyo, JP) was coated on to the same ceramic filter instead of using WO$_3$ and CeO$_2$ composition in a similar manner as described in Example 37. Total coated solid material of RENECAT on ceramic filter was about 2610 mg. FIG. 14 shows the results for the comparative embodiments' effectiveness for removing each of benzene and ethylene.

Comparative Example 45

A commercial activated carbon filter (TTI Floor Care North America [Hoover], Glenwillow, Ohio, USA (Hoover), AH60015) was cut into 50 mm×100 mm (t=10 mm).

Example 46

Figure 15:
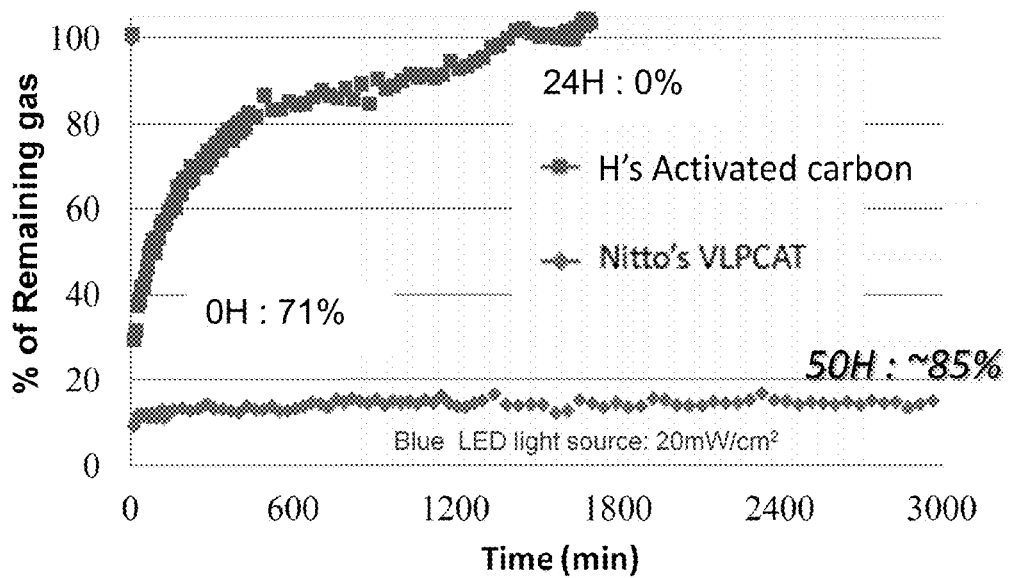
FIG. 15 is a graph of the continued removal of acetaldehyde by a filter comprising activated carbon and a photocatalytic filter embodiments of Example 46.

The decomposition elements described and constructed in Example 38 and Comparative Example 45, were also evaluated for acetaldehyde removal continued time performance in a manner similar to that described in Example 44 above, except that continuous sampling at 15 minute intervals for about 50 hr (3000 min) was performed. FIG. 15 shows the results, illustrating that the embodiments of the present disclosure continued removing acetaldehyde while the comparative filter comprising activated charcoal decreased in removal effectiveness over time.

Example 47

Figure 16:
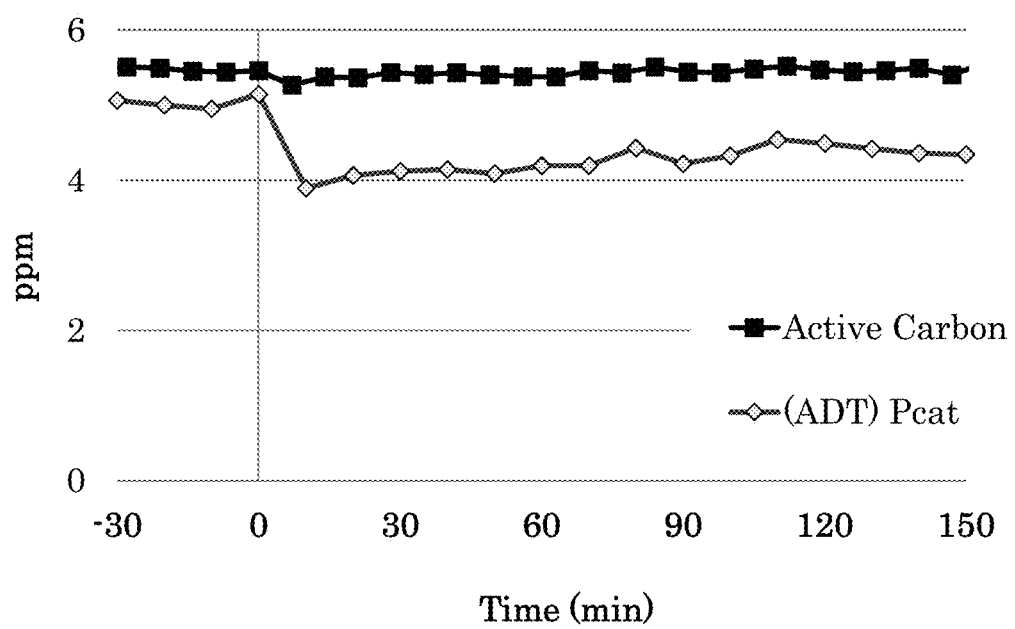
FIG. 16 is a graph of the removal of ethylene by photocatalytic filter embodiments of Example 47 as compared to a filter of activated carbon.

The decomposition elements described and constructed in Example 37 and Comparative Example 45, were also evaluated for ethylene removal continued time performance in a manner similar to that described in Example 39 above, except that continuous sampling at 15 minute intervals to about 3 hr (180 min) was performed. FIG. 16 shows the results, illustrating that the embodiments of the present disclosure continued removing ethylene while the comparative filter comprising activated charcoal decreased in removal effectiveness over time.

Example 48

A commercial UV-Pcat filter (TiO$_2$ coated on aluminum honeycomb, Hoover 440001063, TI Floor Care North America [Hoover], Glenwillow, Ohio, USA) was cut to 100 mm×50 mm×5 mm. The sample was evaluated as described in Example 47 except that a UV lamp (TTI Floor Care North America [Hoover], Glenwillow, Ohio, USA, Model #440001064) was used as a light/irradiation source. Acetaldehyde and Ethylene were chosen as Target VOC gasses. The decomposition rate of Acetaldehyde was 33%, Ethylene was 0%. (FIGS. 17A, 17B, and 18.)

Example 49

Several additional embodiments were constructed in a manner similar to that described in Example 37, except that the thickness of the filter was additionally made at about 10 mm thick instead of the previously described 5 mm thick by using a stack of two 5 mm thick filters, and the light intensity was varied between 5 to 30 mW/cm$^2$. The results and variations are shown in Table 4 below.

TABLE 4

| Subst. | Size (mm) | Gas | Light | RA (%) | QA (umol/H) |
|---|---|---|---|---|---|
| ADT-ANN x1 | 50 × 100 × 5 | Ethylene | BLED 20 mW/cm$^2$ | 14.91 | 2.09 |
|  |  |  | BLED 30 mW/cm$^2$ | 17.47 | 2.45 |
| ADT-ANN x2 | 50 × 100 × 10 | Ethylene | BLED 20 mW/cm$^2$ | 13.86 | 2.11 |
|  |  |  | BLED 30 mW/cm$^2$ | 17.02 | 2.59 |
| Commercial | 50 × 100 × 13 | Ethylene | BLED 20 mW/cm$^2$ | 2.68 | 0.41 |
|  |  |  | BLED 30 mW/cm$^2$ | 6.32 | 0.96 |
| ADT-ANN x1 | 50 × 100 × 5 | Acetaldehyde | BLED 5 mW/cm$^2$ | 81.19 | 9.60 |
|  |  |  | BLED 10 mW/cm$^2$ | 90.57 | 10.70 |
|  |  |  | BLED 20 mW/cm$^2$ | 96.74 | 11.43 |
| Commercial | 50 × 100 × 13 | Acetaldehyde | BLED 5 mW/cm$^2$ | 93.38 | 10.66 |
|  |  |  | BLED 10 mW/cm$^2$ | 96.61 | 11.02 |
|  |  |  | BLED 20 mW/cm$^2$ | 97.02 | 11.06 |

Example 50

Photocatalyst Coated Woven Textile 5 g of WO$_3$ (Global Tungsten & Powder, Towanda, Pa., USA [GTP]), and 3.7 g of CeO$_2$ (Aldrich) was added to high purity alumina ball mill jars containing about 50 g of ZrO$_2$ balls of about 3 mm in diameter and was ground by ball mill (SFM-1 model Desktop Planetary Ball Miller (MTI Corp., Richmond, Calif., USA)) in 25 mL methanol for about 1 hours then dried at about 110° C. by using box dryer 4.5 g of processed WO$_3$/CeO$_2$ powder was added into 5 g of 10% PTFE dispersion in water. (Aldrich 60% PTFE water dispersion was diluted to 10% by adding water). The mixture was first dispersed by placing in a sonication bath for about 5 min. A uniform coating of the photocatalytic composition suspension was obtained by mixing the suspension with sonication probe for about 10 min. The photocatalytic composition suspension was loaded onto the glass fiber textile by dipping glass fiber textile into a glass beaker containing the suspension and leaving it submerged for about 30 seconds to allow the suspension to penetrate the glass fiber textile. In some case, degassing was conducted to promote the penetration of suspension by removing the trapped air in the pores. Glass fiber textile impregnated with photocatalytic composition suspension and PTFE binder suspension was removed from beaker, and the extra suspension was drawn off by gravity. The photocatalytic composition and PTFE binder loaded glass fiber textile was first dried at about 150° C. and then heated at about 350° C. for 5 min. (FIG. 22.)

1.5 g of processed WO$_3$/CeO$_2$ powder was added into 10 g of 10% PTFE dispersion in water. (Aldrich 60% PTFE water dispersion was diluted to 10% by adding water). The photocatalytic composition and PTFE binder loaded glass fiber textile was prepared same method.

Figure 23:
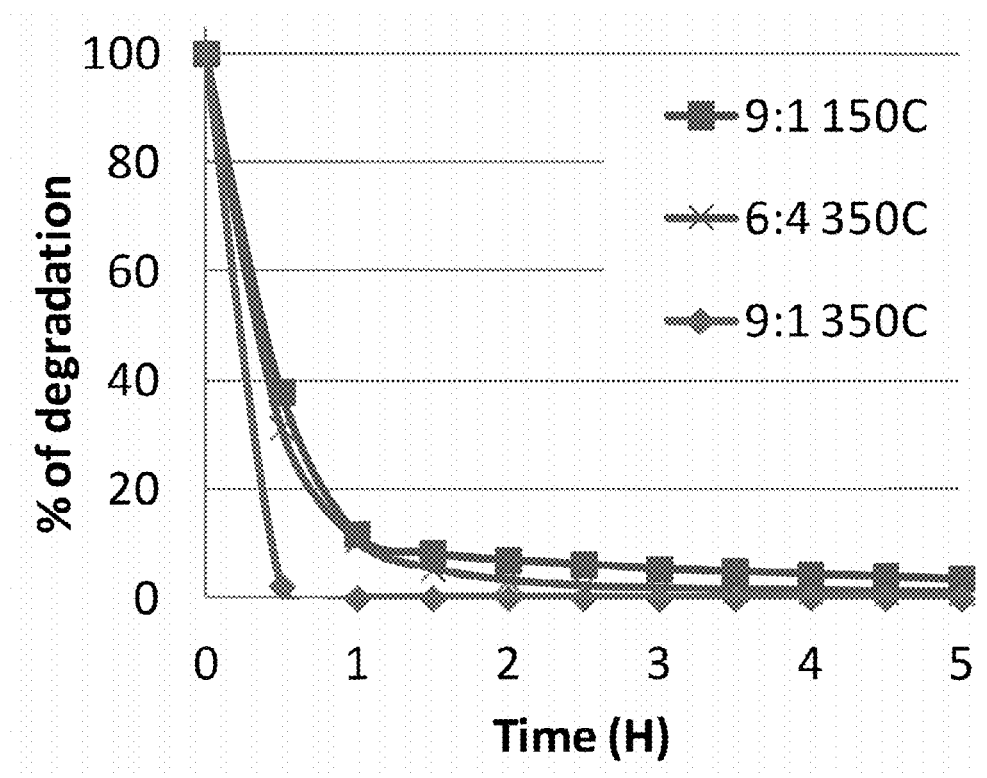
FIG. 23 is a graph of acetaldehyde degradation of a photocatalytic polymer embodiment as described in Example 50.

Coated glass fiber textile was evaluated by similar manner to Example 1. The coated glass fiber textile was placed in 5 L Tedlar bag and the bag was sealed by vacuum heat sealer. About 3 L of ambient air (with about 70 ppm acetylaldehyde) was injected into the bag. Each bag was lightly massaged for about 2 minutes by hand then placed in the dark for about 15 min. The bag was then irradiated with a blue LED at 100 mW/cm$^2$. The acetaldehyde concentration was estimated by Gas Chromatography-Flame Ionization Detector (GC-FID). All filter samples decomposed Acetaldehyde gas more than 80% in 2 hour. The results as shown in FIG. 23.

Example 51

Figure 20:
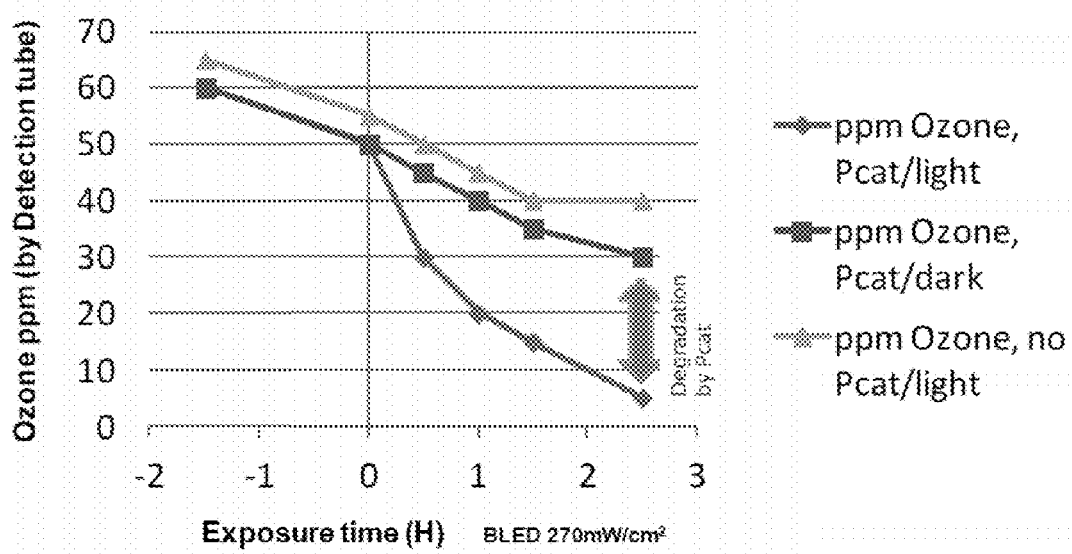
FIG. 20 is a graph of ozone degradation by coated glass slides of Example 51.

A glass slide was prepared in a manner similar to that of Example 1, and evaluated in Example 4, except that 3 L of about 60 ppm ozone in Air where used instead of acetaldehyde. Samples were taken at about 30 minute intervals from the bag interior. FIG. 20 shows the results of exposing the glass slide in light (100 mW/cm$^2$ blue LED) and no light.

Example 52

Pre-treatment of Photocatalyst Powders

Route 1

100 gram of $WO_3$ powder (NanoAmorphous Materials, 60-120 nm, 99%) was added in a 300 ml ball milling jar made of $ZrO_2$. After adding 150 gram of $ZrO_2$ ball of 5 mm in diameter and 130 ml of methanol, the powder was ball-milled for about 19 hrs by planetary ball milling machine at frequency of 15 Hz. The $WO_3$ powder slurry was dried at 110° C. for about 5 hrs to evaporate the methanol. The obtained $WO_3$ powder was placed in a quartz crucible and annealed at about 400° C. in ambient atmosphere for about 5 hrs.

Route 2

25 gram of $WO_3$ powder (NanoAmorphous Materials, 60-120 nm, 99%) and 19 gram of $CeO_2$ powder (NanoAmorphous Materials) were added to a 300 ml $ZrO_2$ ball milling jar. After adding 150 gram of $ZrO_2$ ball of 5 mm in diameter and 220 ml of methanol, the powder was ball-milled for about 19 hrs by a planetary ball milling machine at frequency of 15 Hz. The $WO_3$ powder slurry was dried at 110° C. for about 5 hrs to evaporate the methanol and then annealed in ambient atmosphere at 400° C. for about 5 hrs to get a pre-mixed photocatalyst powder.

Example 53

Figure 32:
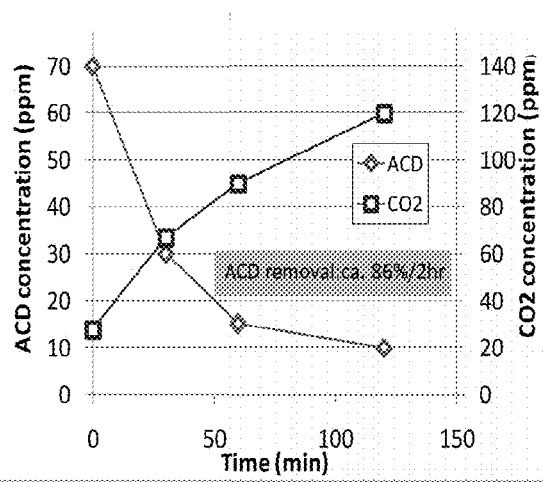
FIG. 32 is a graph of acetaldehyde degradation of a photocatalytic polymer embodiment as described in Example 52.

Photocatalyst coating suspension was prepared by mixing 0.5 gram of pre-mixed $WO_3$ and $CeO_2$ as mentioned above with 2 gram of peroxotitanium acid (PTA-85, Green Millennium, USA) and 1 gram of methanol. The ingredients were mixed with planetary mixer (THINKY A350, THINKY USA, Laguna Hills, Calif., USA) for about 2 min to get a photocatalyst coating suspension. Glass fiber fabric (US Composites, Inc., Palm Beach, Fla., USA, E-glass, 4 oz plain weave) was coated by placing it in the suspension and then draining the surplus suspension off the fabric; followed by drying on a hot plate at about 110° C. for about 30 min and then at about 250° C. for about 1 hr. The coated fabric was assessed for VOC (Acetaldehyde) decomposition as described in Example 50 above, the performance is shown in FIG. 32.

Example 54

Figure 33:
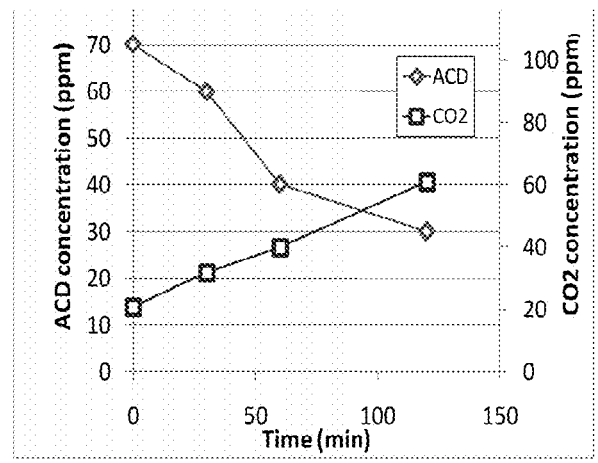
FIG. 33 is a graph of acetaldehyde degradation of a photocatalytic polymer embodiment as described in Example 53.

0.5 gram of pre-mixed $WO_3$ and $CeO_2$ powder as described in EXAMPLE 52 was mixed with 2.0 gram of $CeO_2$ sol (Nyacol Nanotechnologies, Ashland, Mass., USA, pH=2.0) and 1.0 gram of methanol with planetary mixer (THINKY A350) for about 2 min. Glass fiber fabric (US Composites, E-glass, 4 oz plain weave) was coated by following the procedures in EXAMPLE 52. The resulting coated fabric was assessed for VOC (Acetaldehyde) decomposition as described in Example 50 above, the performance is shown in FIG. 33.

Example 55

Figure 34:
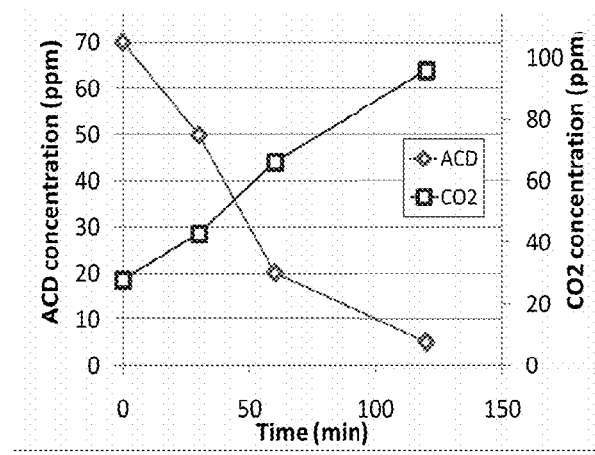
FIG. 34 is a graph of acetaldehyde degradation of a photocatalytic polymer embodiment as described in Example 54.

0.5 gram of pre-mixed $WO_3$ and $CeO_2$ powder as described in EXAMPLE 52 was mixed with 2.0 gram of $CeO_2$ sol (Nyacol Nanotechnologies, D6225 $NH_4$, pH=8.0) and 1.0 gram of methanol with planetary mixer (THINKY A350) for about 2 min. Glass fiber fabric (US composite, E-glass, 4 oz plain weave) was coated by following the procedures in EXAMPLE 52. The resulting coated glass fabric was assessed for VOC (Acetaldehyde) decomposition as described in Example 50 above, the performance is shown in FIG. 34.

Example 56

Figure 35:
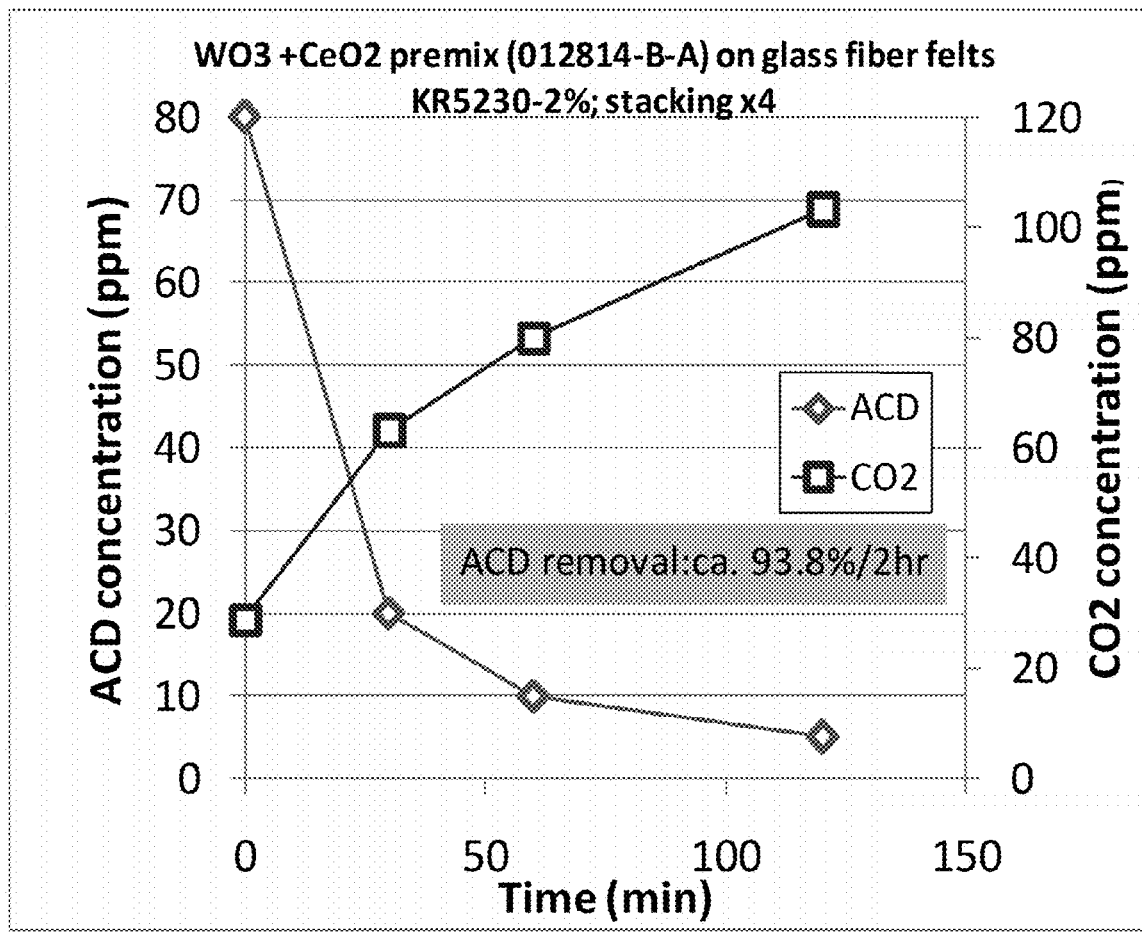
FIG. 35 is a graph of acetaldehyde degradation of a photocatalytic polymer embodiment as described in Example 55.

An undercoating solution containing 2 wt % of organic resin was prepared by mixing 0.4 gram of silicone-modified resin (ShinEtsu Chemical Co. Ltd, Tokyo, Japan, KR-5230) with 19.6 gram of PGMEA (Propylene glycol monomethyl ether acetate, Sigma-Aldrich, 99%) and then mixed with planetary mixer (THINKY A350). The resulting undercoating solution was applied to glass fiber felt (Fibre Glast Developments Corp., Brookville, Ohio, USA, E-glass) by soaking the felt in the undercoating solution for about 5 min; then draining the surplus solution from the felt and then drying the drained felt at about 150° C. for about 30 min. Photocatalyst coating suspension was prepared by mixing the 0.5 gram of pre-mixed photocatalyst powder described in Example 52, route 2, with 2.0 gram of methanol with planetary mixer (THINKY A350). The Photocatalyst coating suspension was applied onto the glass fiber felt with organic resin undercoating by soaking the organic resin coated felt in the photocatalyst coating suspension for about 1 min; then draining the surplus suspension; followed by curing at 230° C. in ambient atmosphere for about 1 hr. The annealed coated felt was assessed for Acetaldehyde decomposition in a manner similar to that described in Example 50, the performance is shown in FIG. 35.

Example 57

Figure 36:
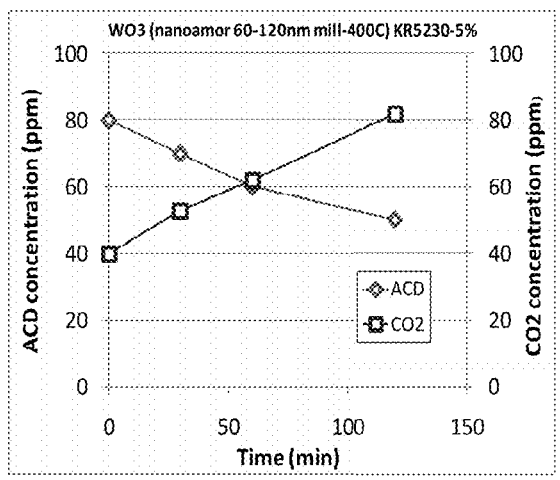
FIG. 36 is a graph of acetaldehyde degradation of a photocatalytic polymer embodiment as described in Example 56.

0.5 wt % of undercoating solution was prepared by following the procedures in EXAMPLE 56 and then applied onto the glass fiber fabric (US Composites, E-glass, 4 oz plain weave) as in EXAMPLE 56. Photocatalyst coating suspension was prepared by mixing 0.5 gram of $WO_3$ as described in route 1 in EXAMPLE 52 and methanol with a Sonic Dismebrator (Fischer Scientific) at power of about 12 W (RMS) for about 30 min. Photocatalyst was loaded onto the glass fiber fabric with undercoating by soaking the undercoated fabric in suspension for about 1 min and then dried at about 230° C. for about 1 hr. The coated glass fiber fabric was assessed for Acetaldehyde decomposition in a manner similar to that described in Example 50, the performance is shown in FIG. 36.

Example 58

Figure 37:
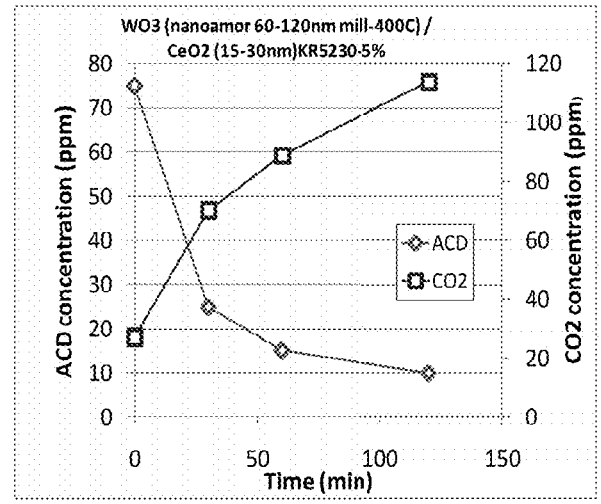
FIG. 37 is a graph of acetaldehyde degradation of a photocatalytic polymer embodiment as described in Example 57.

0.286 gram of $WO_3$ powder as described in route 1 of EXAMPLE 52 was mixed with 0.214 gram of CeO2 powder (NanoAmorphous Materials, 15-30 nm, 99.9%) and 2.0 gram of methanol by Sonic Dismembrator (Fischer Scientific) at 12 W (RMS) for about 30 min. Glass fiber fabric with 0.5 wt % of organic resin undercoating prepared as described in EXAMPLE 57 was soaked in the mixed powder suspension for about 1 min and then dried at about 230° C. for about 1 hr. The coated glass fiber was assessed for Acetaldehyde decomposition in a manner similar to that described in Example 50, the performance is shown in FIG. 37.

Example 59

Figure 38:
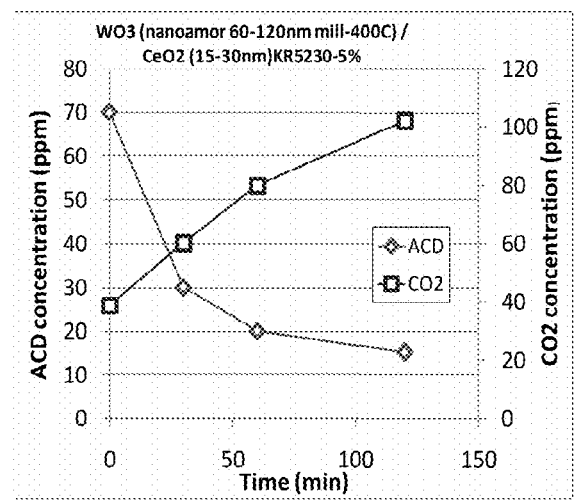
FIG. 38 is a graph of acetaldehyde degradation of a photocatalytic polymer embodiment as described in Example 58.

0.5 gram of mixture of $WO_3$ and $CeO_2$ powder as described in route 2 of EXAMPLE 52 was mixed with 2.0 gram of methanol by Sonic Dismembrator (Fischer Scientific) at 12 W (RMS) for about 30 min. Glass fiber fabric with 0.5 wt % of organic resin undercoating prepared as described in EXAMPLE 57 was soaked in the mixed powder suspension for about 1 min; drained of surplus suspension and then dried at about 230° C. for about 1 hr. The coated glass fiber fabric was assessed for Acetaldehyde decomposition in a manner similar to that described in Example 50, the performance is shown in FIG. 38.

Example 60

A mixture was prepared that contained 45 mg of a $WO_3$ powder (photocatalyst; average particle size 0.25 μm; Kojundo Chemical Laboratory Co., Ltd.), 45 mg of a $CeO_2$ powder (co-catalyst; average particle size 0.025 μm; Sigma Aldrich (JAPAN)), and 10 mg of a PTFE powder (average particle size 0.3 μm; Daikin Industries, Ltd.) ($WO_3$ powder:$CeO_2$ powder:PTFE powder=45 weight %:45 weight %:10 weight %). The mixture was dispersed in water to produce a 20 weight % solid content aqueous dispersion.

Separately, a PTFE porous film (length 5 cm×width 5 cm×thickness 10 μm; Nitto Denko Corporation) was heat fused to a stainless-steel support at 150° C. The aqueous dispersion prepared as above was then spin coated (1,000 rpm for 10 seconds) on the PTFE porous film on the surface not heat fused to the stainless-steel support, and dried at 350° C. for 5 minutes to melt the PTFE powder. As a result, a photocatalyst layer containing the $WO_3$ powder and the $CeO_2$ powder was formed on the surface of the PTFE porous film. The aqueous dispersion was applied in an appropriately adjusted amount that makes the total amount of the photocatalyst and the co-catalyst 10 mg after drying.

The PTFE porous film with the photocatalyst layer formed thereon was then detached from the stainless-steel support. Thereafter, a PET nonwoven fabric (air permeable support; length 5 cm×width 5 cm×thickness 150 μm; basis weight 20 g/m²; Toyobo Co., Ltd.) was laminated on the PTFE porous film on the surface not provided with the photocatalyst layer, and heat fused at 150° C. to produce a filter element of Example 60.

Example 61

A PET nonwoven fabric (length 5 cm×width 5 cm×thickness 150 μm; basis weight 20 g/m²; Toyobo Co., Ltd.) was prepared as an air permeable support. A PTFE porous film (length 5 cm×width 5 cm×thickness 10 μm; Nitto Denko Corporation) was then heat fused (150° C.) and laminated on the PET nonwoven fabric.

Inside the deposition chamber (22° C.) of an aerosol deposition device (carrier gas: oxygen gas) prepared in advance, the laminate of the PET nonwoven fabric and the PTFE porous film obtained as above was installed on the seat of a substrate holder with the PTFE porous film facing upward.

Here, the gap between the jet orifice of the deposition nozzle and the surface of the PTFE porous film was adjusted to 20 mm.

A mixture of the $WO_3$ powder (10 g) and the $CeO_2$ powder (10 g) used in Example 60 was charged into a 500-mL glass aerosol chamber.

With the gas pipe on-off valve closed, and the on-off valve of the connecting tube open, a mechanical booster pump and a rotary pump were operated to create a reduced pressure of 50 Pa inside the deposition chamber and the aerosol chamber.

After adjusting the oxygen gas flow rate to 7 L/min with a gas flowmeter, the gas pipe on-off valve was opened while vibrating the aerosol chamber with a shaker. This aerosolizes $WO_3$ powder and $CeO_2$ powder inside the aerosol chamber, and the aerosol thus obtained was expelled through the deposition nozzle.

Here, the pressure inside the aerosol chamber was about 50,000 Pa, and the pressure inside the deposition chamber was about 280 Pa. The temperature inside the deposition chamber was 25° C.

The seat fixing the laminate of the PET nonwoven fabric and the PTFE porous film was then moved in x-y directions on the stage of the substrate holder at a rate (relative velocity) of 4 mm/second, and the aerosol jetted out of the deposition nozzle was blown onto the surface of the PTFE porous film.

After appropriately repeating the foregoing jetting procedures, a photocatalyst layer was formed on the surface of the PTFE porous film so that the total amount of the photocatalyst and the co-catalyst became 10 mg. Accordingly, the filter element of Example 61 was prepared.

Example 62

In Example 62, firstly, 25 g of $TiO_2$ powder (photocatalyst, average particle diameter: 0.031 m, Nippon Aerosil Co., Ltd.) and 250 ml of ion exchange water were put in a 500-ml eggplant flask, stirred at room temperature to uniformly disperse the particles, thereby preparing an aqueous dispersion of $TiO_2$ powder.

Then, 0.68 g of copper(II) chloride dihydrate (Wako Pure Chemical Industries, Ltd.) was dissolved in 5 ml of ion exchange water, and the aqueous solution of copper(II) chloride dehydrate was added to the aqueous dispersion of $TiO_2$ powder. Subsequently, it was stirred for 1 hour while heated at 90° C., thereby preparing liquid A.

Then, an aqueous solution of sodium hydrate prepared by dissolving 1.255 g of sodium hydrate in 25 ml of ion exchange water was added to the liquid A, and then the pH of the solution was increased from 3 to 11, thereby preparing liquid B.

Then an aqueous solution of glucose prepared by dissolving 6.275 g of glucose (Wako Pure Chemical Industries, Ltd.) in 37.5 ml of ion exchange water was added to the liquid B. It was further stirred for 1 hour while heated at 90°

C., whereby particles of copper(I) oxide and copper(II) oxide were precipitated on the surfaces of the particles of titanium oxide.

Next, the particles after the reaction were filtrated, then subjected to sufficient water washing, and the particles were then dried at 100° C. Consequently, a $Cu_xO$-supporting $TiO_2$ powder (co-catalyst-supporting type photocatalyst) was produced. According to the result of ICP analysis, it was confirmed that 1.0 part by weight of particles of copper oxide were supported with respect to 100 parts by weight of particles of titanium oxide.

A photocatalyst layer was formed on the surface of the PTFE porous film in the same manner as in Example 61, except that the $Cu_xO$-supporting $TiO_2$ powder (10 g) produced as above was charged into the aerosol chamber instead of the $WO_3$ powder and the $CeO_2$ powder used in Example 61, and that the photocatalyst layer was formed on the surface of the PTFE porous film in a manner that makes the amount of the $Cu_xO$-supporting $TiO_2$ powder (co-catalyst-supporting photocatalyst) 10 mg. Accordingly, the filter element of Example 62 was prepared. Scanning electron microscopy confirmed that the co-catalyst $Cu_xO$ particles were supported on the photocatalyst $TiO_2$ particles in the photocatalyst layer of the filter element of Example 62.

Example 63

In Example 63, firstly, a $Cu_xO$-supporting $SnO_2$ powder was produced in the same manner as in Example 62, except that $SnO_2$ powder (photocatalyst; average particle size 0.015 μm; Kanto Chemical Co., Inc.) was used instead of $TiO_2$ powder. According to the result of ICP analysis, it was confirmed that 1.0 part by weight of particles of copper oxide were supported with respect to 100 parts by weight of particles of tin oxide. The same procedures used in Example 62 were used except that the $Cu_xO$-supporting $SnO_2$ powder was used instead of the $Cu_xO$-supporting $TiO_2$ powder, whereby a photocatalyst layer was formed on the surface of the PTFE porous film in a manner that makes the amount of the $Cu_xO$-supporting $SnO_2$ powder (co-catalyst-supporting photocatalyst) 10 mg. Accordingly, the filter element of Example 63 was prepared. Scanning electron microscopy confirmed that the co-catalyst $Cu_xO$ particles were supported on the photocatalyst $SnO_2$ particles in the photocatalyst layer of the filter element of Example 63.

Example 64

In Example 64, a photocatalyst layer was laminated on the surface of the PET nonwoven fabric to make the total amount of the photocatalyst and the co-catalyst 10 mg, using the same procedures used in Example 61, except that the PTFE porous film was not laminated on the PET nonwoven fabric. Accordingly, the filter element of Example 64 was prepared.

Example 65

In Example 65, a photocatalyst layer was laminated on the surface of the PET nonwoven fabric to make the amount of the $Cu_xO$-supporting $SnO_2$ powder (co-catalyst-supporting photocatalyst) 10 mg, using the same procedures used in Example 63, except that the PTFE porous film was not laminated on the PET nonwoven fabric. Accordingly, the filter element of Example 65 was prepared.

The filter elements of Examples were each measured for VOC decomposition, and evaluated for photocatalytic activity, as follows.

The filter element of interest for the measurement of photocatalytic activity was put in a 5-L Tedlar bag. The bag was sealed, and the air inside the bag was released to create a vacuum. The same Tedlar bag was then charged with 3 L of compressed air and calibration acetaldehyde, and the acetaldehyde concentration was adjusted to 100 ppm. The acetaldehyde concentration was measured with a calibration gas chromatograph equipped with a flame ionization detector (GC-FID; GC-2010 plus available from Shimadzu Corporation).

After being allowed to stand in the dark for 1 hour to stabilize the acetaldehyde concentration (equilibrium state), the Tedlar bag was irradiated with light of a diode array that emits monochromatic blue light (wavelength 455 nm, irradiation intensity 10 mW/cm$^2$). After 1-hour irradiation, the gas inside the Tedlar bag was collected, and the residual acetaldehyde concentration was analyzed by GC-FID.

The acetaldehyde decomposition rate (%) was calculated according to the following equation A.

$$\text{Acetaldehyde decomposition rate (\%)} = (X-Y)/X \times 100. \quad \text{Equation A}$$

In the equation, X is the acetaldehyde concentration before the irradiation (100 ppm), and Y is the acetaldehyde concentration after the Irradiation.

It can be said that, the higher the acetaldehyde decomposition rate is, the higher the VOC decomposition ability is, i.e., the higher the photocatalytic activity is, and conversely, the lower the acetaldehyde decomposition rate is, the lower the VOC decomposition ability is, i.e., the lower the photocatalytic activity is.

The filter elements of Examples were each evaluated for filter element durability.

The filter element was irradiated with light in such a manner that the photocatalyst layer of the filter element was irradiated at an irradiation intensity of 60 W/m$^2$ (sunshine carbon arc), using a sunshine weather meter (Suga Test Instruments Co., Ltd.).

After 30 days, the filter element (Examples 60 to 63: PTFE porous film and PET nonwoven fabric; Examples 64 and 65: PET nonwoven fabric) was visually examined for the presence or absence of deterioration.

Table 5 shows the percentage acetaldehyde decomposition, and the presence or absence of deterioration of each filter element of Examples.

TABLE 5

| | Acetaldehyde concentration before irradiation (ppm) | Acetaldehyde concentration after 1-hour irradiation (ppm) | Percentage acetaldehyde decomposition (%) | Presence or absence of filter element deterioration |
|---|---|---|---|---|
| Ex. 60 | 100 | 20 | 80 | Absent |
| Ex. 61 | 100 | 20 | 80 | Absent |
| Ex. 62 | 100 | 40 | 60 | Absent |
| Ex. 63 | 100 | 40 | 60 | Absent |
| Ex. 64 | 100 | 20 | 80 | Present |
| Ex. 65 | 100 | 40 | 60 | Present |

The filter elements of Examples 60 to 63 showed photocatalytic activity, and deterioration was not confirmed in the PET nonwoven fabric. There was also no deterioration in the PTFE porous film supporting the photocatalyst layer. The filter elements of Examples 60 to 63 were thus found to have both photocatalytic activity and filter element durability. The photocatalysts used for the filter elements of Examples 60 and 61 in particular showed excellent VOC decomposition under visible light.

Photocatalytic activity was also observed in the filter elements of Examples 64 and 65. However, because the photocatalyst layer was directly supported on the PET nonwoven fabric, the photocatalysis of the photocatalyst caused deterioration in the PET nonwoven fabric. The filter elements of Examples 64 and 65 were thus inferior in terms of filter element durability as compared to Examples 60 to Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise Indicated herein or clearly contradicted by context. All methods described herein can be performed in any suitable order unless otherwise Indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as Indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

The present application is based on a U.S. provisional application No. 61/843,264 filed Jul. 5, 2013, a U.S. provisional application No. 61/843,267 filed Jul. 5, 2013, a U.S. provisional application No. 61/899,799 filed Nov. 4, 2013, a U.S. provisional application No. 61/899,804 filed Nov. 4, 2013, a U.S. provisional application No. 61/944,879 filed Feb. 26, 2014, and a Japanese patent application No. 2014-113001 filed May 30, 2014, the contents of which are incorporated herein by reference.

The invention claimed is:

1. A filter element for decomposing contaminants comprising:
   a substrate; and
   a photocatalytic composition comprising at least a photocatalyst and a co-catalyst;
   wherein the photocatalyst contains $WO_3$ and the co-catalyst contains $CeO_2$, and
   wherein the molar ratio of $WO_3$ to $CeO_2$ is 1:5 to 5:1: and
   wherein the filter element comprises a fluororesin porous layer laminated on at least one surface of the substrate, wherein the photocatalytic composition is disposed on the fluororesin porous layer.

2. The filter element as claimed in claim 1, wherein the substrate is a gas permeable support.

3. The filter element as claimed in claim 1, wherein the photocatalyst shows visible light responsiveness.

4. The filter element as claimed in claim 1, wherein said photocatalyst further comprises $TiO_2$ or $Ti(O,C,N)_2$:Sn.

5. The filter element as claimed in claim 1, wherein said co-catalyst further comprises anatase $TiO_2$, $SrTiO_3$, $KTaO_3$, or $KNbO_3$.

6. The filter element as claimed in claim 1, wherein said co-catalyst further comprises $In_2O_5$, $Ta_2O_5$, anatase $TiO_2$, rutile $TiO_2$, or a combination of anatase and rutile $TiO_2$.

7. The filter element as claimed in claim 1, wherein a fluororesin constituting the fluororesin porous layer contains polytetrafluoroethylene.

8. The filter element as claimed in claim 1, wherein the photocatalytic composition is formed on the fluororesin porous layer through an aerosol deposition method.

9. A system for decomposing contaminants comprising:
   the filter element of claim 1 and
   a source of electromagnetic radiation that is in optical communication with said photocatalytic composition.

10. The system as claimed in claim 9, wherein said substrate defines a volume.

11. The system as claimed in claim 9, further comprising an enclosing element, wherein said substrate is disposed within said enclosing element.

12. The system as claimed in claim 9, further comprising an airflow element for creating an airflow, said airflow element being disposed within said enclosing element.

13. The system as claimed in claim 9, wherein the photocatalyst shows visible light responsiveness.

14. The system as claimed in claim 9, wherein said photocatalyst further comprises $TiO_2$ or $Ti(O,C,N)_2$:Sn.

15. The system as claimed in claim 9, wherein said co-catalyst further comprises anatase $TiO_2$, $SrTiO_3$, $KTaO_3$, or $KNbO_3$.

16. The system as claimed in claim 9, wherein said co-catalyst further comprises $In_2O_5$, $Ta_2O_5$, anatase $TiO_2$, rutile $TiO_2$, or a combination of anatase and rutile $TiO_2$.

17. A method comprising the steps of:
placing a system as claimed in claim 9 in atmospheric communication with an ethylene-sensitive plant; and
reducing the amount of ethylene to a concentration below a threshold by contacting ethylene with the photocatalytic composition while said photocatalytic composition is illuminated by electromagnetic radiation comprising a wavelength sufficient to activate the photocatalytic composition.

18. The method as claimed in claim 17, further comprising the step of:
maintaining the concentration of ethylene below said threshold.

19. The filter element as claimed in claim 1, wherein the photocatalytic composition further comprises a dopant.

20. The filter element as claimed in claim 19, wherein the molar ratio of co-catalyst to dopant is 99.9:0.1 to 80:20.

21. The filter element as claimed in claim 20, wherein the dopant is at least one of carbon, nitrogen, sulfur, fluorine, tin, zinc, manganese, aluminum, selenium, niobium, nickel, zirconium, cerium, or iron.

22. The filter element as claimed in claim 1, wherein the molar ratio of $WO_3$ to $CeO_2$ is 1:4 to 4:1.

23. The filter element as claimed in claim 1, wherein the substrate is a porous substrate.

* * * * *